US011111520B2

(12) United States Patent
Blauwkamp et al.

(10) Patent No.: US 11,111,520 B2
(45) Date of Patent: Sep. 7, 2021

(54) COMPOSITIONS AND METHODS FOR ENRICHING POPULATIONS OF NUCLEIC ACIDS

(71) Applicant: Karius, Inc., Menlo Park, CA (US)

(72) Inventors: Timothy A. Blauwkamp, Palo Alto, CA (US); Fred Christians, Los Altos Hills, CA (US); Igor D. Vilfan, East Palo Alto, CA (US); Scott Smith, San Francisco, CA (US); Michael Kertesz, Menlo Park, CA (US)

(73) Assignee: Karius, Inc., Redwood City, CA (US)

( * ) Notice: Subject to any disclaimer, the term of this patent is extended or adjusted under 35 U.S.C. 154(b) by 294 days.

(21) Appl. No.: 15/157,374

(22) Filed: May 17, 2016

(65) Prior Publication Data

US 2017/0016048 A1 Jan. 19, 2017

Related U.S. Application Data

(60) Provisional application No. 62/163,273, filed on May 18, 2015, provisional application No. 62/334,348, filed on May 10, 2016.

(51) Int. Cl.
C12Q 1/68 (2018.01)
C12Q 1/6806 (2018.01)
C12Q 1/6888 (2018.01)
C12Q 1/6809 (2018.01)
C12Q 1/6804 (2018.01)

(52) U.S. Cl.
CPC ......... C12Q 1/6806 (2013.01); C12Q 1/6888 (2013.01); C12Q 1/6804 (2013.01); C12Q 1/6809 (2013.01)

(58) Field of Classification Search
CPC .. C12Q 1/6806; C12Q 1/6888; C12Q 1/6809; C12Q 2525/161
See application file for complete search history.

(56) References Cited

U.S. PATENT DOCUMENTS

| | | | |
|---|---|---|---|
| 6,753,137 B2 | 6/2004 | Lo et al. | |
| 6,759,217 B2 | 7/2004 | Kopreski | |
| RE39,920 E | 11/2007 | Umansky et al. | |
| 7,803,929 B2 | 9/2010 | Melkonyan et al. | |
| 7,914,982 B2 | 3/2011 | Melkonyan et al. | |
| 7,973,154 B2 | 7/2011 | Melkonyan et al. | |
| 8,318,434 B2 | 11/2012 | Cuppens | |
| 8,486,626 B2 | 7/2013 | Umansky et al. | |
| 8,682,592 B2 | 3/2014 | Rabinowitz et al. | |
| 8,703,652 B2 | 4/2014 | Quake et al. | |
| 2004/0209299 A1 | 10/2004 | Pinter et al. | |
| 2005/0202414 A1 | 9/2005 | Jia et al. | |
| 2006/0073506 A1 | 4/2006 | Christians et al. | |
| 2006/0183107 A1* | 8/2006 | Melkonyan | 435/5 |
| 2006/0292585 A1* | 12/2006 | Nautiyal | C12Q 1/6827 435/6.12 |
| 2010/0068711 A1* | 3/2010 | Umansky | C12Q 1/6806 435/6.16 |
| 2010/0297710 A1* | 11/2010 | Hoyal-Wrightson | C12N 15/1003 435/91.52 |
| 2011/0257031 A1 | 10/2011 | Bodeau et al. | |
| 2012/0021412 A1 | 1/2012 | Melkonyan et al. | |
| 2012/0077185 A1 | 3/2012 | Oliphant et al. | |
| 2012/0100549 A1* | 4/2012 | Eshoo | C12Q 1/686 435/6.12 |
| 2012/0190663 A1 | 7/2012 | Gornik et al. | |
| 2012/0295810 A1 | 11/2012 | Quake et al. | |
| 2013/0024127 A1 | 1/2013 | Stuelpnagel et al. | |
| 2013/0178544 A1 | 7/2013 | Melkonyan et al. | |
| 2013/0224740 A1 | 8/2013 | Thierry et al. | |
| 2013/0237431 A1 | 9/2013 | Lo et al. | |
| 2013/0245961 A1 | 9/2013 | Lo et al. | |
| 2013/0252835 A1 | 9/2013 | Koh et al. | |
| 2013/0253844 A1* | 9/2013 | Lo | G16B 40/00 702/19 |
| 2013/0303461 A1 | 11/2013 | Iafrate et al. | |
| 2013/0310260 A1 | 11/2013 | Kim et al. | |
| 2014/0064669 A1 | 3/2014 | Kachmar | |
| 2014/0066317 A1 | 3/2014 | Talasaz | |
| 2014/0147851 A1 | 5/2014 | Qian | |
| 2014/0180594 A1 | 6/2014 | Kim et al. | |

(Continued)

FOREIGN PATENT DOCUMENTS

EP 1856295 A2 11/2007
EP 1885877 A2 2/2008

(Continued)

OTHER PUBLICATIONS

Nishida et al.( PloS One5.3 (2010): e9916; p. 1-8). (Year: 2010).*
Deligezer et al. (Clinical chemistry 54.7 (2008): 1125-1131.). (Year: 2008).*
Zhou et al. ("A novel method of selective removal of human DNA improves PCR sensitivity for detection of *Salmonella typhi* in blood samples." BMC infectious diseases 12.1 (2012): 164.) (Year: 2012).*
Song et al. ("Nuclease-assisted suppression of human DNA background in sepsis." PLoS One 9.7 (2014): e103610; 5 pages) (Year: 2014).*
Anisimova, et al. Thermolabile duplex-specific nuclease. Biotechnology Letters, Feb. 2009, vol. 31, Issue 2, pp. 251-257.

(Continued)

Primary Examiner — Sahana S Kaup
(74) Attorney, Agent, or Firm — Wilson Sonsini Goodrich & Rosati

(57) ABSTRACT

This disclosure provides methods and compositions that are useful for enriching a particular population of nucleic acids (a "population of interest") within a complex mixture of nucleic acids. The population of interest may make up a minor portion of a complex mixture of nucleic acids. The methods and compositions provided herein are useful for detecting, predicting, diagnosing, or monitoring a disease or disorder, particularly a disease or disorder caused by a foreign microbe or pathogen.

49 Claims, 12 Drawing Sheets

(56) References Cited

U.S. PATENT DOCUMENTS

| | | |
|---|---|---|
| 2014/0227691 A1 | 8/2014 | May et al. |
| 2014/0242582 A1 | 8/2014 | Oliphant et al. |
| 2014/0274740 A1 | 9/2014 | Srinivasan et al. |
| 2014/0363812 A1 | 12/2014 | Micalef |
| 2016/0017420 A1 | 1/2016 | Koh et al. |
| 2016/0304953 A1 | 10/2016 | Chen et al. |
| 2017/0145507 A1 | 5/2017 | Koh et al. |
| 2017/0145508 A1 | 5/2017 | Koh et al. |
| 2017/0145509 A1 | 5/2017 | Koh et al. |

FOREIGN PATENT DOCUMENTS

| | | | |
|---|---|---|---|
| EP | 2351857 A1 | 8/2011 | |
| EP | 2612926 A1 | 7/2013 | |
| EP | 2728014 A1 | 5/2014 | |
| JP | 2008536481 A | 9/2008 | |
| JP | 2010537650 A | 12/2010 | |
| WO | WO-9408239 A1 | 4/1994 | |
| WO | WO-2009102470 A2 | 8/2009 | |
| WO | WO-2011057061 A1 | 5/2011 | |
| WO | WO-2011143659 A2 | 11/2011 | |
| WO | WO-2012088348 A2 | 6/2012 | |
| WO | WO-2012135815 A2 | 10/2012 | |
| WO | WO-2012159023 A2 | 11/2012 | |
| WO | WO-2012168815 A2 | 12/2012 | |
| WO | WO-2013043922 A1 | 3/2013 | |
| WO | WO-2013052907 A2 | 4/2013 | |
| WO | WO-2013109981 A1 | 7/2013 | |
| WO | WO-2013113012 A2 | 8/2013 | |
| WO | WO-2013132305 A1 | 9/2013 | |
| WO | WO-2013134261 A1 * | 9/2013 | ........... C12Q 1/6869 |
| WO | WO-2013156627 A1 | 10/2013 | |
| WO | WO-2013159035 A2 | 10/2013 | |
| WO | WO-2013188846 A1 | 12/2013 | |
| WO | WO-2014019275 A1 | 2/2014 | |
| WO | WO-2014029792 A1 | 2/2014 | |
| WO | WO-2014039556 A1 | 3/2014 | |
| WO | WO-2014068075 A1 | 5/2014 | |
| WO | WO-2014128453 A1 | 8/2014 | |
| WO | WO-2014149134 A2 | 9/2014 | |
| WO | WO-2014151117 A1 | 9/2014 | |
| WO | WO-2014179805 A1 | 11/2014 | |
| WO | WO-2015048535 A1 * | 4/2015 | ........... C12Q 1/6806 |
| WO | WO-2015058079 A1 | 4/2015 | |
| WO | WO-2015070086 A1 * | 5/2015 | ............ C12Q 1/701 |
| WO | WO-2015085105 A1 | 6/2015 | |
| WO | WO-2016187234 A1 | 11/2016 | |

OTHER PUBLICATIONS

Arroyo, J.D. et al. Argonaute2 complexes carry a population of circulating microRNAs independent of vesicles in human plasma, 2011. Proc. Natl. Acad. Sci. USA vol. 108, pp. 5003-5008.

Calvo, et al. A novel secreted endonuclease from Culex quinquefasciatus salivary glands. J Exp Biol. Jul. 2006;209(Pt 14):2651-9.

De Vlaminck, et al. Temporal response of the human virome to immunosuppression and antiviral therapy. Cell. Nov. 21, 2013;155(5):1178-87. doi: 10.1016/j.cell.2013.10.034.

Fleischhacker, et al. Methods for isolation of cell-free plasma DNA strongly affect DNA yield. Clin Chim Acta. Nov. 20, 2011;412(23-24):2085-8. doi: 10.1016/j.cca.2011.07.011. Epub Jul. 23, 2011.

Highlander, Sarah K., High throughput sequencing methods for microbiome profiling: application to food animal systems, Animal Health Research Reviews, Jun. 2012, vol. 13(1); pp. 40-53.

International Search Report and Written Opinion dated Oct. 14, 2016 for International PCT Patent Application No. PCT/US2016/032936.

Matvienko, et al. Consequences of Normalizing Transcriptomic and Genomic Libraries of Plant Genomes Using a Duplex-Specific Nuclease and Tetramethylammonium Chloride. PloS One 8.2 (2013): e55913.

Mojsin, et al. Rapid detection and purification of sequence specific DNA binding proteins using magnetic separation. Journal of the Serbian Chemical Society 7105(577):135-141575. Jan. 2006. DOI: 10.2298/JSC0602135M.

Nilsen, et al. The enzyme and the cDNA sequence of a thermolabile and double-strand specific DNase from Northern shrimps (*Pandalus borealis*). PLoS One. Apr. 22, 2010;5(4):e10295. doi: 10.1371/journal.pone.0010295.

Phylochip: Berkeley Lab Earth Sciences Division website. Accessed Apr. 2015. http://esd.lbl.gov/research/facilities/andersenlab/phylochip.html.

Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.

Shagin, et al. A novel method for SNP detection using a new duplex-specific nuclease from crab hepatopancreas. Genome Res. Dec. 2002;12(12):1935-42.

Song, et al. Nuclease-assisted suppression of human DNA background in sepsis. PLoS One. Jul. 30, 2014;9(7):e103610. doi: 10.1371/journal.pone.0103610. eCollection 2014.

Yamada, et al. PrimerStation: a highly specific multiplex genomic PCR primer design server for the human genome. Nucleic Acids Res. Jul. 1, 2006;34(Web Server issue):W665-9.

EP16797172.0 European Search Report dated Sep. 10, 2018.

Arbabi, et al., Cell-free DNA fragment-size distribution analysis for non-invasive prenatal CNV prediction. Bioinformatics, vol. 32, Issue 11, Jun. 1, 2016, pp. 1662-1669.

Barcelos Barra, et al., EDTA-mediated inhibition of DNases protects circulating cell-free DNA from ex vivo degradation in blood samples. Clinical Biochemistry, 2015; 48:976-981.

Begley, et al., The interaction between bacteria and bile. FEMS Microbiology review. 2005; 29: 625-651.

Burnham, et al. Single-stranded DNA library preparation uncovers the origin and diversity of ultrashort cell-free DNA in plasma. Sci Rep. Jun. 14, 2016;6:27859. doi: 10.1038/srep27859.

Burnham, et al. Urinary cell-free DNA is a versatile analyte for monitoring infections of the urinary tract. Nat Commun. Jun. 20, 2018;9(1):2412. doi: 10.1038/s41467-018-04745-0.

Chereji, et al. Quantitative MNase-seq accurately maps nucleosome occupancy levels. Genome Biol. Sep. 13, 2019;20(1):198. doi: 10.1186/s13059-019-1815-z.

Han, et al. The Biology of Cell-free DNA Fragmentation and the Roles of DNASE1, DNASE1L3, and DFFB. Am J Hum Genet. Feb. 6, 2020;106(2):202-214. doi: 10.1016/j.ajhg.2020.01.008. Epub Jan. 30, 2020.

Harkins, et al. A novel NGS library preparation method to characterize native termini of fragmented DNA. Nucleic Acids Res. May 7, 2020;48(8):e47. doi: 10.1093/nar/gkaa128.

* cited by examiner

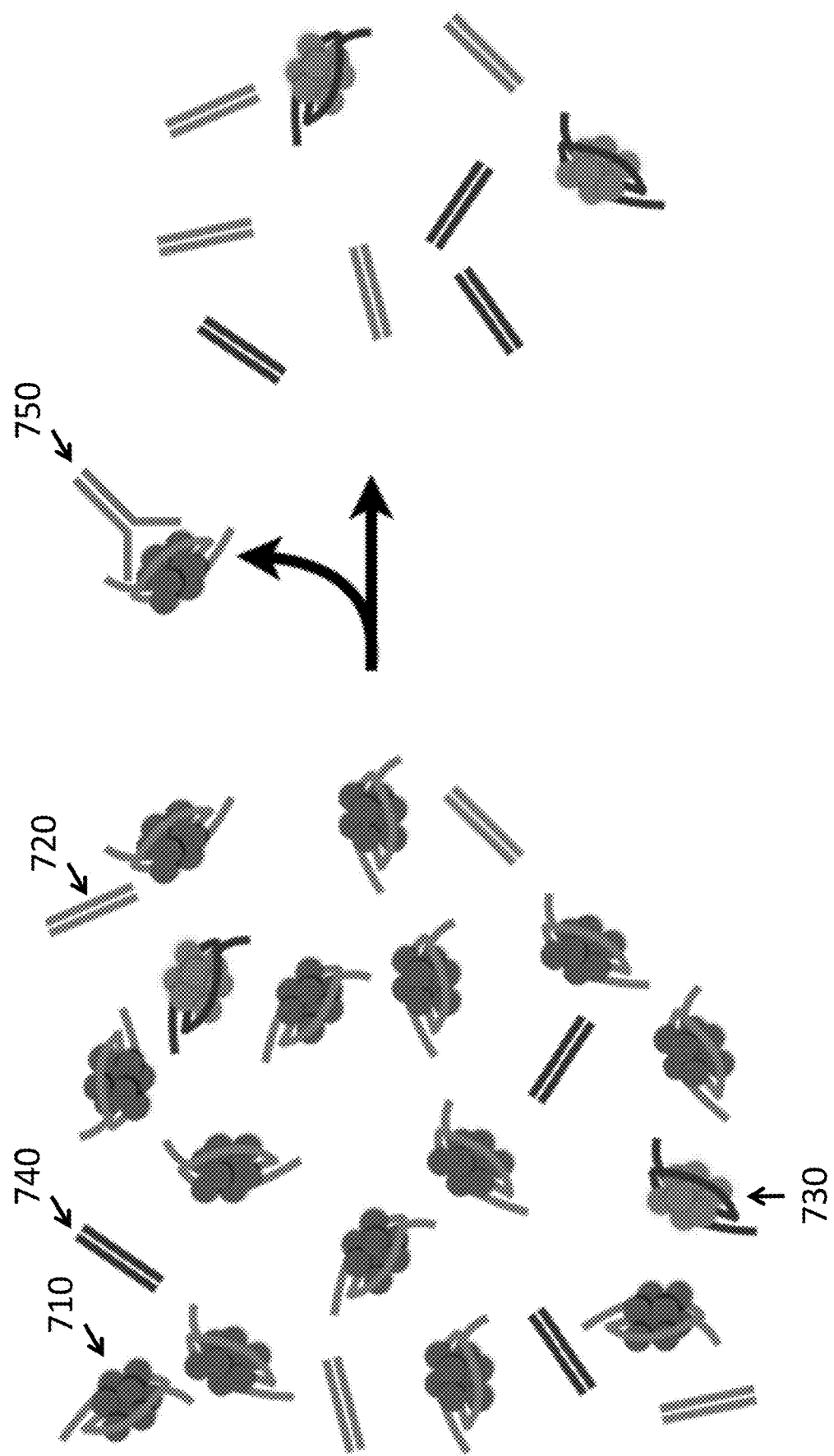

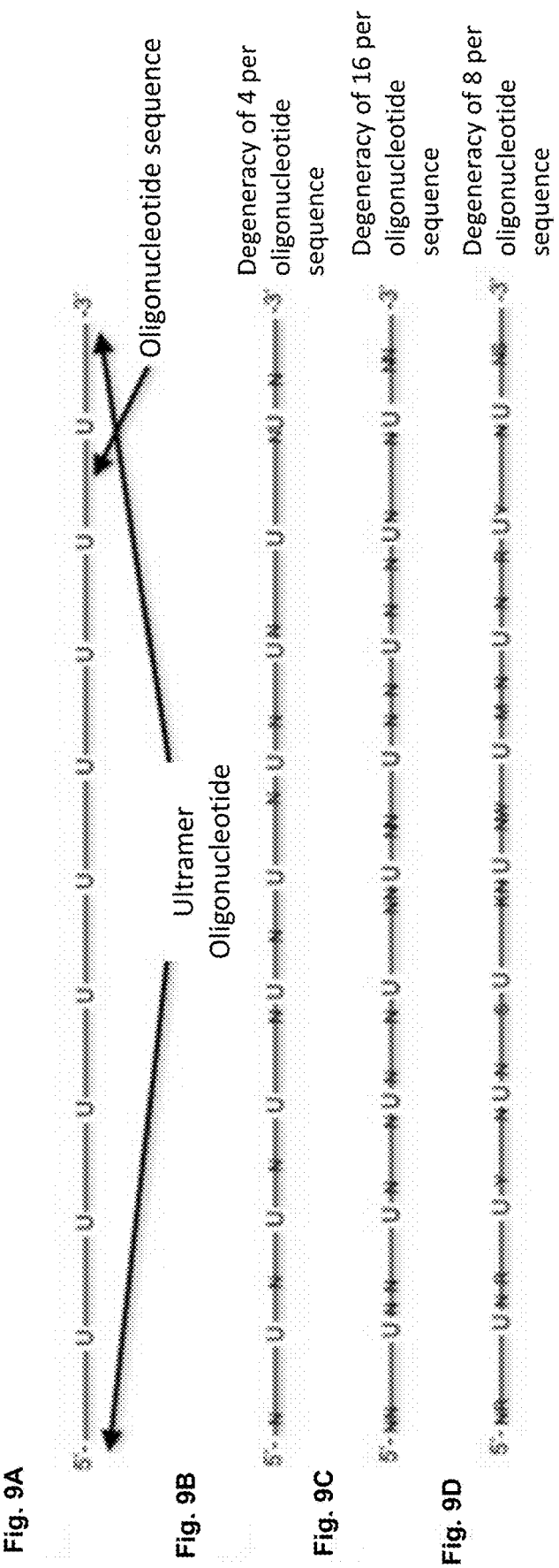

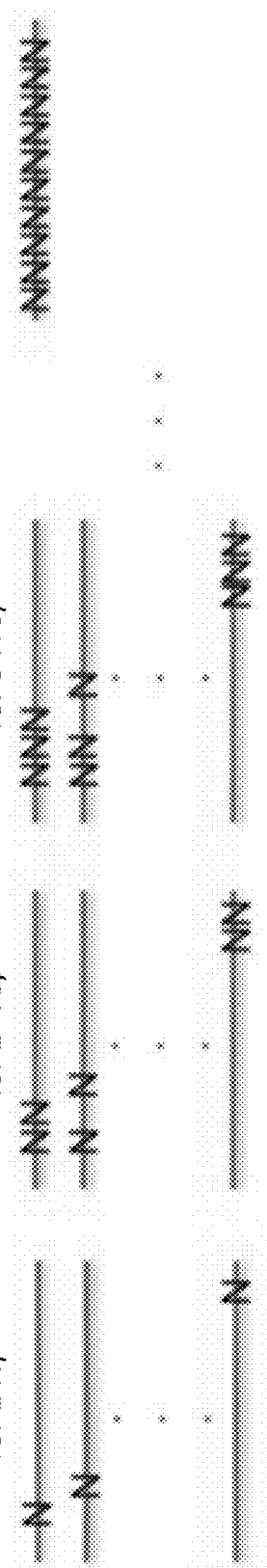
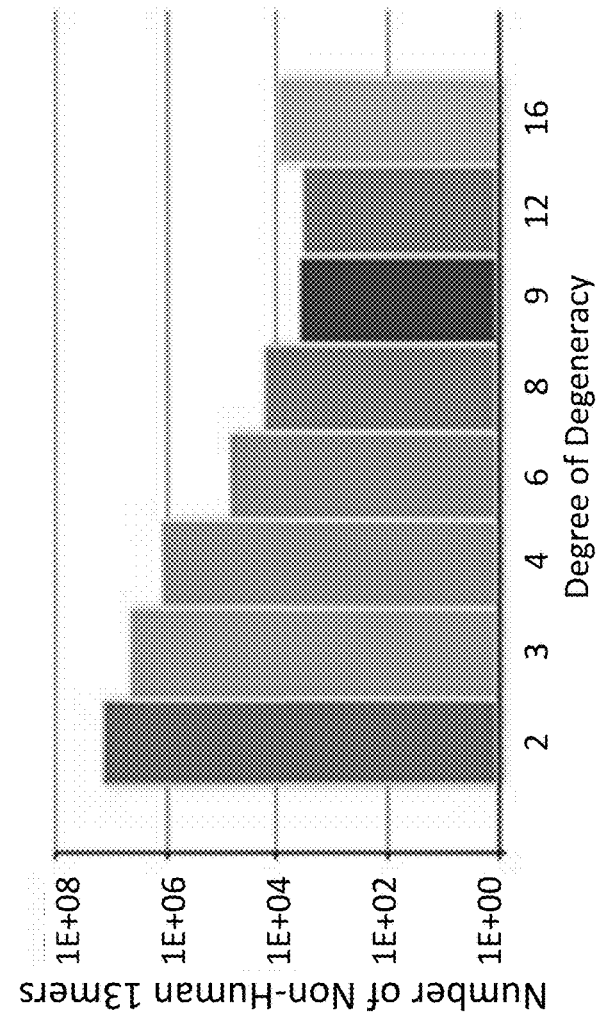

COMPOSITIONS AND METHODS FOR ENRICHING POPULATIONS OF NUCLEIC ACIDS

CROSS-REFERENCE

This application claims the benefit of U.S. Provisional Application No. 62/163,273, filed May 18, 2015, and U.S. Provisional Application No. 62/334,348, filed May 10, 2016, which applications are incorporated herein by reference.

BACKGROUND

Infectious diseases and disorders are a challenge for primary caregivers and patients alike and often have poor rates of detection, especially when compared to other illnesses. Improper detection of infectious disease may be due to a number of factors, including the lack of meaningful tests that can generate an accurate answer quickly. Given the slow speed of some diagnostic tests, many physicians opt to treat patients based on suspected etiology before test results are received, rather than risk worsening of symptoms during the wait time. Tests for infectious disease are also generally pathogen-specific; and thus, physicians must have some idea of the etiologic agent of a patient's symptoms prior to ordering the test. Another confounding factor for some infectious diseases is that the infectious agent may mutate during the course of infection, such that an initial diagnosis may not accurately reflect the nature of a patient's condition at a later time point. Secondary infections and co-infections can also obfuscate diagnoses and treatment, as they may mask other sources of infection or escape detection altogether.

Misdiagnosis and under-diagnosis of pathogenic infections can have dire consequences to patients as well as to communities at large. For example, over-use or misuse of antibiotics can promote the rise of antibiotic-resistant bacteria, which is a danger not only for the patient but for others who come in contact with the patient. There is thus a need in the art for reliable, comprehensive, and affordable tests for identifying pathogens in a sample.

SUMMARY OF THE INVENTION

The present disclosure generally provides methods of identifying non-host nucleic acids in samples taken from a host and in which host nucleic acids are present. Such methods have a variety of applications, including, for example, identification of infectious or pathogenic organisms within a host through the analysis of cell-free samples taken from a host. In general, methods described herein may involve the selective enrichment of non-host nucleic acids relative to host nucleic acids derived in a host sample, such as a cell-free plasma sample from the host. The enriched nucleic acids may then be analyzed in order to identify the presence of the non-host nucleic acids and the presence of a pathogen or infectious organism within the host. Identification of the presence of non-host nucleic acids, pathogens, or infectious organisms may enable detection, diagnosis, prognosis, monitoring, or staging of an infectious disease or disorder experienced by the host.

In one example, the disclosure provides a method of identifying pathogens in a host, where the method begins by providing a cell-free blood or plasma sample from the host. The blood or plasma sample is then enriched for non-host derived nucleic acids relative to host derived nucleic acids, and the enriched sample is then analyzed for the non-host derived nucleic acids, and any pathogens in the host may then be identified from the non-host nucleic acids.

In one aspect, the present disclosure provides a method of priming or capturing non-host sequences in a sample of nucleic acids from a host, the method comprising: (a) providing a sample of nucleic acids from the host, wherein the sample of nucleic acids from the host comprises host nucleic acids and non-host nucleic acids; (b) mixing the sample of nucleic acids from the host with a collection of oligonucleotides, thereby obtaining a mixture, wherein the collection of oligonucleotides comprises at least 1,000 oligonucleotides with different nucleotide sequences, wherein the different nucleotide sequences are specifically selected to contain non-host nucleic acid sequences at least 10 nucleotides in length; and (c) within the mixture, contacting the collection of oligonucleotides with the sample of nucleic acids, wherein the contacting causes non-host nucleic acids within the mixture to bind the non-host nucleic acid sequences at least 10 nucleotides in length, thereby priming or capturing non-host nucleic acids, and the contacting causes up to 10% of the host nucleic acids to bind the non-host nucleic acid sequences at least 10 nucleotides in length.

In some embodiments, the method further comprises preferentially amplifying the primed or captured non-host nucleic acids in a reaction. In some embodiments, the method further comprises sequencing the primed or captured non-host nucleic acids by conducting a sequencing assay, such as a Next Generation sequencing assay, a high-throughput sequencing assay, a massively parallel sequencing assay, a Nanopore sequencing assay, or a Sanger sequencing assay. In some embodiments, the method further comprises preferentially isolating the primed or captured non-host nucleic acids. In some embodiments, the preferentially isolating comprises performing a pull-down assay. In some embodiments, the method further comprises performing a primer extension reaction on the primed or captured non-host nucleic acids. In some embodiments, the at least 1,000 oligonucleotides with different nucleotide sequences contain a nucleic acid label. In some embodiments, the primed or captured non-host nucleic acids are RNA non-host nucleic acids. In some embodiments, the method further comprises conducting a polymerization reaction on the primed or captured RNA non-host nucleic acids. In some embodiments, the polymerization reaction is performed by reverse transcriptase.

In another aspect, the present disclosure provides a method of sequencing non-host sequences in a sample of nucleic acids from a host, the method comprising: (a) providing a sample of nucleic acids from the host, wherein the sample of nucleic acids from the host comprises host nucleic acids and non-host nucleic acids; (b) mixing the sample of nucleic acids from the host with a collection of oligonucleotides, thereby obtaining a mixture, wherein the collection of oligonucleotides comprises at least 1,000 oligonucleotides with different nucleotide sequences, wherein the different nucleotide sequences are specifically selected to contain non-host nucleic acid sequences at least 10 nucleotides in length; (c) within the mixture, contacting the collection of oligonucleotides to the sample of nucleic acids, wherein the contacting causes non-host nucleic acids within the mixture to bind the non-host nucleic acid sequences at least 10 nucleotides in length and the contacting causes up to 10% of the host nucleic acids to bind the non-host nucleic acid sequences at least 10 nucleotides in length; and (d) sequencing the non-host nucleic acids bound to the non-host nucleic acid sequences at least 10 nucleotides in length by conducting a sequencing assay.

In some embodiments, the method further comprises preferentially amplifying the non-host nucleic acids in a reaction. In some embodiments, the sequencing assay is a Next Generation sequencing assay, a high-throughput sequencing assay, a massively parallel sequencing assay, a Nanopore sequencing assay, or a Sanger sequencing assay. In some embodiments, the method further comprises preferentially isolating the non-host nucleic acids. In some embodiments, the isolating comprises performing a pull-down assay. In some embodiments, the method further comprises performing a primer extension reaction on the non-host nucleic acids. In some embodiments, the at least 1,000 oligonucleotides with different nucleotide sequences contain a nucleic acid label. In some embodiments, the non-host nucleic acids are RNA non-host nucleic acids. In some embodiments, the method further comprises conducting a polymerization reaction on the RNA non-host nucleic acids. In some embodiments, the polymerization reaction is performed by reverse transcriptase.

In some embodiments of a method provided herein, the at least 1,000 oligonucleotides with different nucleotide sequences are at least 10,000 oligonucleotides with different nucleotide sequences. In some embodiments of a method provided herein, the at least 1,000 oligonucleotides with different nucleotide sequences are at least 100,000 oligonucleotides with different nucleotide sequences. In some embodiments of a method provided herein, the at least 1,000 oligonucleotides with different nucleotide sequences are at least 1,000,000 oligonucleotides with different nucleotide sequences. In some embodiments of a method provided herein, the at least 1,000 oligonucleotides with different nucleotide sequences are not conjugated to a solid support. In some embodiments of a method provided herein, the at least 1,000 oligonucleotides with different nucleotide sequences have lengths of up to 200 nucleotides. In some embodiments of a method provided herein, each of the at least 1,000 oligonucleotides with different nucleotide sequences comprises a domain of nucleotides from 10 to 20 nucleotides in length, wherein each domain of nucleotides from 10 to 20 nucleotides in length comprises a different nucleotide sequence. In some embodiments of a method provided herein, each domain of nucleotides from 10 to 20 nucleotides in length is 12-15 nucleotides in length. In some embodiments of a method provided herein, each domain of nucleotides from 10 to 20 nucleotides in length is 13-15 nucleotides in length. In some embodiments of a method provided herein, each domain of nucleotides from 10 to 20 nucleotides in length is not a mammalian nucleic acid sequence. In some embodiments of a method provided herein, the host is a mammalian host and the sample of nucleic acids from the mammalian host comprises mammalian host nucleic acids and non-mammalian nucleic acids. In some embodiments of a method provided herein, the host is a human host and the sample of nucleic acids from the human host comprises human host nucleic acids and non-human nucleic acids. In some embodiments of a method provided herein, the non-human nucleic acids comprise microbial nucleic acids. In some embodiments of a method provided herein, the non-human nucleic acids comprise bacterial nucleic acids. In some embodiments of a method provided herein, the sample of nucleic acids from the host comprises at least five non-host nucleic acid sequences and the method further comprises detecting the at least five non-host nucleic acid sequences. In some embodiments of a method provided herein, the sample of nucleic acids from the host is selected from the group consisting of blood, plasma, serum, saliva, cerebrospinal fluid, synovial fluid, lavage, urine, and stool, such as from blood, plasma, and serum. In some embodiments of a method provided herein, the sample is selected from the group consisting of blood, plasma, and serum. In some embodiments of a method provided herein, the sample of nucleic acids from the host is a sample of circulating nucleic acids. In some embodiments of a method provided herein, the sample of nucleic acids from the host is a sample of circulating cell-free nucleic acids. In some embodiments of a method provided herein, the sample of nucleic acids from the host comprises a nucleic acid sequencing-ready library. In some embodiments of a method provided herein, the sample of nucleic acids from the host comprises single-stranded DNA or cDNA. In some embodiments of a method provided herein, the nucleic acids are DNA. In some embodiments of a method provided herein, the nucleic acids are RNA. In some embodiments of a method provided herein, the sample of nucleic acids from the host does not comprise artificially fragmented nucleic acids. In some embodiments of a method provided herein, the collection of oligonucleotides comprises DNA, RNA, PNA, LNA, BNA, or any combination thereof. In some embodiments of a method provided herein, the collection of oligonucleotides comprises DNA oligonucleotides. In some embodiments of a method provided herein, the collection of oligonucleotides comprises RNA oligonucleotides.

In some embodiments of a method provided herein, the collection of oligonucleotides are DNA oligonucleotides. In some embodiments of a method provided herein, the collection of oligonucleotides are RNA oligonucleotides. In some embodiments of a method provided herein, the collection of oligonucleotides is labeled with a nucleic acid label or a chemical label. In some embodiments of a method provided herein, the chemical label is biotin. In some embodiments of a method provided herein, the collection of oligonucleotides does not comprise artificially fragmented nucleic acids. In some embodiments of a method provided herein, the non-host nucleic acids are selected from the group consisting of pathogenic nucleic acids, microbial nucleic acids, bacterial nucleic acids, viral nucleic acids, fungal nucleic acids, parasitic nucleic acids, and any combination thereof. In some embodiments of a method provided herein, the non-host nucleic acids are microbial nucleic acids. In some embodiments of a method provided herein, the non-host nucleic acids are bacterial nucleic acids. In some embodiments of a method provided herein, the non-host nucleic acids are viral nucleic acids.

In still another aspect, the present disclosure provides a method of enriching non-host sequences in a sample of nucleic acids from a host, the method comprising: (a) providing a sample of nucleic acids from the host, wherein the sample of nucleic acids from the host is a sample of single-stranded nucleic acids from the host and comprises host nucleic acids and non-host nucleic acids; (b) renaturing at least a portion of the single-stranded nucleic acids from the host, thereby producing a population of double-stranded nucleic acids within the sample; and (c) removing at least a portion of the double-stranded nucleic acids within the sample using a nuclease, thereby enriching non-host sequences in the sample of nucleic acids from the host.

In some embodiments, the method further comprises performing a sequencing assay. In some embodiments, the sample of nucleic acids from the host comprises at least five non-host nucleic acid sequences and the method further comprises detecting the at least five non-host nucleic acid sequences. In some embodiments, the host is human. In some embodiments, the sample of nucleic acids from the host is a sample of circulating nucleic acids. In some embodiments, the sample of nucleic acids from the host is a sample of circulating cell-free nucleic acids. In some embodiments, the sample of nucleic acids from the host is selected from the group consisting of blood, plasma, serum, saliva, cerebrospinal fluid, synovial fluid, lavage, urine, and stool, such as from blood, plasma, and serum. In some embodiments, the nucleic acids are DNA. In some embodiments, the nucleic acids are RNA. In some embodiments, the method further comprises adding single-stranded host sequences to the sample of single-stranded nucleic acids from the host. In some embodiments, the method further comprises denaturing at least a portion of the nucleic acids in the sample of nucleic acids using heat to generate the sample of single-stranded nucleic acids. In some embodiments, the renaturing at least a portion of the nucleic acids occurs within a set time frame. In some embodiments, the renaturing at least a portion of the nucleic acids occurs within 96 hours. In some embodiments, the renaturing comprises renaturing in the presence of trimethylammonium chloride. In some embodiments, the nuclease is duplex specific nuclease, BAL-31, double-strand specific DNase, or a combination thereof. In some embodiments, the nuclease is duplex specific nuclease. In some embodiments, the nuclease is BAL-31. In some embodiments, the nuclease is active against double-stranded nucleic acids. In some embodiments, the nuclease is not active against single-stranded nucleic acids. In some embodiments, the nucleic acids are not artificially fragmented.

In yet another aspect, the present disclosure provides a method of enriching non-host sequences in a sample of nucleic acids from a host, the method comprising: (a) providing the sample of nucleic acids from the host, wherein the sample of nucleic acids from the host comprises host nucleic acids associated with nucleosomes and non-host nucleic acids; and (b) removing at least a portion of the host nucleic acids associated with nucleosomes, thereby enriching the non-host nucleic acids in the sample of nucleic acids from the host.

In some embodiments, the method further comprises performing a sequencing assay. In some embodiments, the sample of nucleic acids from the host comprises at least five non-host nucleic acid sequences and the method further comprises detecting the at least five non-host nucleic acid sequences. In some embodiments, the host is human. In some embodiments, the sample of nucleic acids from the host is a sample of circulating nucleic acids. In some embodiments, the sample of nucleic acids from the host is a sample of circulating cell-free nucleic acids. In some embodiments, the sample of nucleic acids from the host is selected from the group consisting of blood, plasma, serum, saliva, cerebrospinal fluid, synovial fluid, lavage, urine, and stool, such as from blood, plasma, and serum. In some embodiments, the removing in step (b) comprises performing electrophoresis. In some embodiments, the removing in step (b) comprises performing isotachophoresis. In some embodiments, the removing in step (b) comprises using a porous filter. In some embodiments, the removing in step (b) comprises using an ion exchange column. In some embodiments, the removing in step (b) comprises using one or more antibodies specific to one or more histones. In some embodiments, the one or more histones are selected from the group consisting of Histone H2A N-terminus, Histone H2A solvent exposed epitope, mono-methylation on Lys9 in Histone H3, di-methylation on Lys9 in Histone H3, trimethylation on Lys56 in Histone H3, phosphorylation on Ser14 in Histone H2B, and phosphorylation on Ser139 in Histone H2A.X. In some embodiments, the one or more antibodies are immobilized on a column. In some embodiments, the method further comprises removing the one or more antibodies.

In another aspect, the present disclosure provides a method of enriching non-host sequences in a sample of nucleic acids from a host, the method comprising: (a) providing the sample of nucleic acids from the host, wherein the sample of nucleic acids from the host comprises host nucleic acids and non-host nucleic acids; and (b) removing or isolating DNA of one or more length intervals, thereby enriching the non-host nucleic acids in the sample of nucleic acids from the host.

In some embodiments, step (b) comprises removing DNA of one or more length intervals. In some embodiments, step (b) comprises isolating DNA of one or more length intervals. In some embodiments, the one or more length intervals are selected from the group consisting of about 180 base pairs, about 360 base pairs, about 540 base pairs, about 720 base pairs, and about 900 base pairs. In some embodiments, the one or more length intervals are selected from the group consisting of about 150 base pairs, about 300 base pairs, about 450 base pairs, about 600 base pairs, and about 750 base pairs. In some embodiments, the one or more length intervals are selected from the group consisting of about 160 base pairs, about 320 base pairs, about 480 base pairs, about 640 base pairs, and about 800 base pairs. In some embodiments, the one or more length intervals are selected from the group consisting of about 170 base pairs, about 340 base pairs, about 510 base pairs, about 680 base pairs, and about 850 base pairs. In some embodiments, the one or more length intervals are selected from the group consisting of about 190 base pairs, about 380 base pairs, about 570 base pairs, about 760 base pairs, and about 950 base pairs. In some embodiments, the one or more length intervals are selected from the group consisting of 150 base pairs or multiples thereof, 160 base pairs or multiples thereof, 170 base pairs or multiples thereof, 190 base pairs or multiples thereof, and any combination thereof. In some embodiments, step (b) comprises removing DNA that is above about 100, 120, 150, 175, 200, 250, 300, 400, or 500 bases in length. In some embodiments, step (b) comprises isolating DNA that is up to about 100, 120, 150, 175, 200, 250, or 300 bases in length. In some embodiments, step (b) comprises isolating DNA that is between about 10 bases and about 100 bases in length, between about 10 bases and about 120 bases in length, between about 10 bases and about 150 bases in length, between about 10 bases and about 175 bases in length, between about 10 bases and about 200 bases in length, between about 10 bases and about 250 bases in length, between about 10 bases and about 300 bases in length, about 30 bases and about 100 bases in length, between about 30 bases and about 120 bases in length, between about 30 bases and about 150 bases in length, between about 30 bases and about 175 bases in length, between about 30 bases and about 200 bases in length, between about 30 bases and about 250 bases in length, or between about 30 bases and about 300 bases in length.

In some embodiments, the method further comprises performing a sequencing assay. In some embodiments, the sample of nucleic acids from the host comprises at least five non-host nucleic acid sequences and the method further comprises detecting the at least five non-host nucleic acid sequences. In some embodiments, the host is human. In some embodiments, the sample of nucleic acids from the host is a sample of circulating nucleic acids. In some embodiments, the sample of nucleic acids from the host is a sample of circulating cell-free nucleic acids.

In still another aspect, the present disclosure provides a method of enriching non-host sequences in a sample of nucleic acids from a host, the method comprising: (a) providing a sample of nucleic acids from the host, wherein the sample of nucleic acids from the host comprises host nucleic acids, non-host nucleic acids, and exosomes; and (b) removing or isolating at least a portion of the exosomes, thereby enriching non-host sequences in the sample of nucleic acids from the host.

In some embodiments, step (b) comprises removing at least a portion of the exosomes. In some embodiments, step (b) comprises isolating at least a portion of the exosomes. In some embodiments, the method further comprises performing a sequencing assay. In some embodiments, the sample of nucleic acids from the host comprises at least five non-host nucleic acid sequences and the method further comprises detecting the at least five non-host nucleic acid sequences. In some embodiments, the host is human. In some embodiments, the sample of nucleic acids from the host is selected from the group consisting of blood, plasma, serum, saliva, cerebrospinal fluid, synovial fluid, lavage, urine, and stool, such as from blood, plasma, and serum. In some embodiments, the sample of nucleic acids from the host is a sample of circulating nucleic acids. In some embodiments, the sample of nucleic acids from the host is a sample of circulating cell-free nucleic acids. In some embodiments, the method further comprises removing the host nucleic acids within the exosomes. In some embodiments, the method further comprises isolating non-host nucleic acids. In some embodiments, the removing or isolating in step (b) comprises removing or isolating white blood cell-derived exosomes. In some embodiments, the white blood cell is a macrophage. In some embodiments, the removing or isolating in step (b) comprises using immunoprecipitation to removing or isolating the white blood cell-derived exosomes.

In some embodiments of a method provided herein, the method further comprises adding one or more nucleic acid barcodes to one or more samples. In some embodiments of a method provided herein, the method further comprises adding to the sample one or more nucleic acids specific for one or more pathogenicity loci; antimicrobial resistance markers; antibiotic resistance markers; antiviral resistance markers; antiparasitic resistance markers; informative genotyping regions; sequences common among two or more microbes, pathogens, bacteria, viruses, fungi, and/or parasites; non-host sequences integrated into the host genome; masking non-host sequences; non-host mimicking sequences; masking host sequences; host mimicking sequences; and sequences specific to one or more microbes, pathogens, bacteria, viruses, fungi, and/or parasites.

In yet another aspect, the present disclosure provides a method of priming or capturing sequences in a sample of nucleic acids from a host, the method comprising: (a) providing a sample of nucleic acids from the host; (b) mixing the sample of nucleic acids from the host with one or more region of interest nucleic acids specific for one or more pathogenicity loci; antimicrobial resistance markers; antibiotic resistance markers; antiviral resistance markers; antiparasitic resistance markers; informative genotyping regions; sequences common among two or more microbes, pathogens, bacteria, viruses, fungi, and/or parasites; non-host sequences integrated into the host genome; masking non-host sequences; non-host mimicking sequences; masking host sequences; host mimicking sequences; and sequences specific to one or more microbes, pathogens, bacteria, viruses, fungi, and/or parasites; thereby obtaining a mixture; and (c) within the mixture, contacting the one or more region of interest nucleic acids to the sample of nucleic acids, wherein the contacting causes nucleic acids in the sample of nucleic acids to bind the one or more region of interest nucleic acids, thereby priming or capturing the nucleic acids.

In some embodiments, the method further comprises conducting a nucleic acid amplification reaction using the one or more nucleic acids specific for one or more pathogenicity loci; antimicrobial resistance markers; antibiotic resistance markers; antiviral resistance markers; antiparasitic resistance markers; informative genotyping regions; sequences common among two or more microbes, pathogens, bacteria, viruses, fungi, and/or parasites; non-host sequences integrated into the host genome; masking non-host sequences; non-host mimicking sequences; masking host sequences; host mimicking sequences; and sequences specific to one or more microbes, pathogens, bacteria, viruses, fungi, and/or parasites. In some embodiments, the nucleic acid amplification reaction comprises polymerase chain reaction, reverse transcription, transcription-mediated amplification, or ligase chain reaction. In some embodiments, the method further comprises isolating nucleic acids specific for one or more pathogenicity loci; antimicrobial resistance markers; antibiotic resistance markers; antiviral resistance markers; antiparasitic resistance markers; informative genotyping regions; sequences common among two or more microbes, pathogens, bacteria, viruses, fungi, and/or parasites; non-host sequences integrated into the host genome; masking non-host sequences; non-host mimicking sequences; masking host sequences; host mimicking sequences; and sequences specific to one or more microbes, pathogens, bacteria, viruses, fungi, and/or parasites. In some embodiments, the isolating comprises performing a pull-down assay. In some embodiments, the method further comprises performing a sequencing assay. In some embodiments, the host is human. In some embodiments, the sample of nucleic acids from the host is a sample of circulating nucleic acids. In some embodiments, the sample of nucleic acids from the host is a sample of circulating cell-free nucleic acids.

In another aspect, the present disclosure provides a collection of oligonucleotides comprising at least 1,000 oligonucleotides linked to a sequencing adapter sequence, wherein the collection of oligonucleotides comprising at least 1,000 oligonucleotides is specifically selected such that: (a) each of the at least 1,000 oligonucleotides comprises a domain of nucleotides; (b) the domain of nucleotides has a length from 10 to 20 nucleotides; (c) each domain of nucleotides with length from 10 to 20 nucleotides has a different nucleotide sequence; and (d) each domain of nucleotides with length from 10 to 20 nucleotides is not present in one or more genomes.

In some embodiments, the at least 1,000 oligonucleotides are no more than 200 nucleotides in length. In some embodiments, the one or more genomes are one or more mammalian genomes. In some embodiments, the one or more mammalian genomes are selected from human genomes, dog genomes, cat genomes, rodent genomes, pig genomes, cow genomes, sheep genomes, goat genomes, rabbit genomes, horse genomes, and any combination thereof. In some embodiments, the one or more mammalian genomes are human genomes. In some embodiments, the one or more genomes is one genome. In some embodiments, each domain of nucleotides with length from 10 to 20 nucleotides is 12-15 nucleotides in length. In some embodiments, each domain of nucleotides with length from 10 to 20 nucleotides is 13-15 nucleotides in length. In some embodiments, the oligonucleotides are DNA oligonucleotides. In some embodiments, the oligonucleotides are RNA oligonucleotides. In some embodiments, the oligonucleotides are synthesized oligonucleotides. In some embodiments, the oligonucleotides do not comprise artificially fragmented nucleic acids. In some embodiments, the oligonucleotides are labeled with a nucleic acid label, a chemical label, or an optical label. In some embodiments, the at least 1,000 oligonucleotides are at least 5,000 oligonucleotides. In some embodiments, the at least 1,000 oligonucleotides are at least 10,000 oligonucleotides. In some embodiments, the at least 1,000 oligonucleotides are at least 100,000 oligonucleotides. In some embodiments, the at least 1,000 oligonucleotides are at least 1,000,000 oligonucleotides. In some embodiments, the at least 1,000 oligonucleotides comprise a domain of nucleotides from 10 to 20 nucleotides in length with different sequences that are present in one or more microbial, pathogen, bacterial, viral, fungal, or parasitic genomes.

In still another aspect, the present disclosure provides a method of generating a collection of oligonucleotides, the method comprising: (a) providing at least 1,000 oligonucleotides, wherein the at least 1,000 oligonucleotides comprise a domain of nucleotides from 10 to 20 nucleotides in length with different sequences; (b) providing a sample of nucleic acids from a host; (c) mixing the at least 1,000 oligonucleotides with the nucleic acids from the host; and (d) generating a collection of oligonucleotides, comprising isolating at least a subset of the at least 1,000 oligonucleotides that does not hybridize with the nucleic acids from the host.

In some embodiments, the at least 1,000 oligonucleotides have lengths of up to 200 nucleotides. In some embodiments, the domain of nucleotides is 12-15 nucleotides in length. In some embodiments, the domain of nucleotides is 13-15 nucleotides in length. In some embodiments, the oligonucleotides are DNA or RNA. In some embodiments, the oligonucleotides are single-stranded. In some embodiments, the oligonucleotides are synthesized oligonucleotides. In some embodiments, the nucleic acids from the host are labeled with a nucleic acid label or a chemical label. In some embodiments, the chemical label is biotin. In some embodiments, isolating of step (d) comprises performing electrophoresis. In some embodiments, isolating of step (d) comprises performing a pull-down assay. In some embodiments, the method further comprises denaturing at least a portion of the nucleic acids from the host using heat.

In yet another aspect, the present disclosure provides a method of generating a collection of oligonucleotides, the method comprising: (a) determining domains of nucleotides from 10 to 20 nucleotides in length that are present in a background population selected from the group consisting of a genome, exome, and transcriptome; and (b) generating a collection of oligonucleotides, comprising at least 1,000 oligonucleotides, wherein the at least 1,000 oligonucleotides comprise a domain of nucleotides from 10 to 20 nucleotides in length with different sequences that are not present in the background population.

In some embodiments, the at least 1,000 oligonucleotides have lengths of up to 200 nucleotides. In some embodiments, the domain of nucleotides is 12-15 nucleotides in length. In some embodiments, the domain of nucleotides is 13-15 nucleotides in length. In some embodiments, the host is a human. In some embodiments, the background population is a genome. In some embodiments, the background population is an exome. In some embodiments, the background population is a transcriptome. In some embodiments, the determining is performed computationally.

In another aspect, the present disclosure provides a method of identifying pathogens in a host, the method comprising: providing a sample from the host; enriching the sample for non-host derived nucleic acids relative to host derived nucleic acids, wherein the enriching comprises preferentially removing nucleic acids with lengths that are above about 300 bases in length from the sample; analyzing the non-host derived nucleic acids; and identifying pathogens in the host from the non-host nucleic acids.

In some embodiments of a method described herein, the enriching step comprises preferentially removing nucleic acids from the sample that are above about 120, about 150, about 200, or about 250 bases in length. In some embodiments of a method described herein, the enriching step comprises preferentially enriching nucleic acids from the sample that are between about 10 bases and about 60 bases in length, between about 10 bases and about 120 bases in length, between about 10 bases and about 150 bases in length, between about 10 bases and about 300 bases in length between about 30 bases and about 60 bases in length, between about 30 bases and about 120 bases in length, between about 30 bases and about 150 bases in length, or between about 30 bases and about 200 bases in length, between about 30 bases and about 300 bases in length. In some embodiments of a method described herein, the enriching step comprises preferentially digesting host derived nucleic acids. In some embodiments of a method described herein, the enriching step comprises preferentially replicating the non-host derived nucleic acids. In some embodiments of a method described herein, the non-host nucleic acids are preferentially replicated using one or more priming or capturing oligonucleotides that are complementary to one or more domains of nucleotides not present in the host derived nucleic acids. In some embodiments of a method described herein, the domain of nucleotides is from 10 to 20 nucleotides in length. In some embodiments of a method described herein, the domain of nucleotides is from 12 to 15 nucleotides in length. In some embodiments of a method described herein, the domain of nucleotides is a 13-mer or 14-mer. In some embodiments of a method described herein, the host is a eukaryotic host. In some embodiments of a method described herein, the host is a vertebrate host. In some embodiments of a method described herein, the host is a mammalian host. In some embodiments of a method described herein, the non-host DNA comprises DNA from a pathogenic organism. In some embodiments of a method described herein, the sample comprises a blood or plasma sample. In some embodiments of a method described herein, the sample is a cell-free sample. In some embodiments of a method described herein, the enriching step increases the ratio of non-host derived nucleic acids relative to host derived nucleic acids by at least 2×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 30×, at least 40×, at least 50×, at least 60×, at least 70×, at least 80×, at least 90×, at least 100×, at least 1000×, at least 5000×, or at least 10,000×.

In another aspect, the present disclosure provides an ultramer oligonucleotide, comprising 10 oligonucleotide sequences in a single oligonucleotide, wherein: (a) each of the 10 oligonucleotide sequences is separated by a uracil residue or apurinic/apyrimidinic site; (b) each of the 10 oligonucleotide sequences comprises a domain of nucleotides; (c) the domain of nucleotides has a length from 10 to 20 nucleotides; and (d) each domain of nucleotides with length from 10 to 20 nucleotides has a different nucleotide sequence. In some embodiments, the 10 oligonucleotide sequences are no more than 200, 150, 100, 50, 40, 30, or 20 nucleotides in length. In some embodiments, the 10 oligonucleotide sequences are the same length. In some embodiments, each domain of nucleotides with length from 10 to 20 nucleotides is not present in one or more genomes. In some embodiments, the one or more genomes are one or more mammalian genomes. In some embodiments, the one or more mammalian genomes are selected from human genomes, dog genomes, cat genomes, rodent genomes, pig genomes, cow genomes, sheep genomes, goat genomes, rabbit genomes, horse genomes, and any combination thereof. In some embodiments, the one or more mammalian genomes are human genomes. In some embodiments, the one or more genomes is one genome. In some embodiments, each domain of nucleotides with length from 10 to 20 nucleotides is 12-15 nucleotides in length. In some embodiments, each domain of nucleotides with length from 10 to 20 nucleotides is 13-15 nucleotides in length. In some embodiments, each domain of nucleotides with length from 10 to 20 nucleotides comprises a mixed base. In some embodiments, each domain of nucleotides with length from 10 to 20 nucleotides comprises 1 or more, 2 or more, 3 or more, 4 or more, 5 or more, 6 or more, 7 or more, 8 or more, 9 or more, 10 or more, 11 or more, 12 or more, or 13 or more mixed bases. In some embodiments, the mixed base is selected from the group consisting of N (A, C, G, T), D (A, G, T), V (A, C, G), B (C, G, T), H (A, C, T), W (A, T), S (C, G), K (G, T), M (A, C), Y (C, T), R (A, G), and any combination thereof. In some embodiments, the 10 oligonucleotide sequences have a same degree of degeneracy. In some embodiments, the 10 oligonucleotide sequences have a degree of degeneracy of 2, 3, 4, 6, 8, 9, 12, 16, 18, 24, 27, 32, 36, 48, 54, 64, 72, 81, 96, 108, 128, 144, 162, 192, 216, 243, or 256. In some embodiments, the 10 oligonucleotide sequences have a degree of degeneracy with prime factors selected from 2 and 3. In some embodiments, the 10 oligonucleotide sequences are DNA. In some embodiments, the 10 oligonucleotide sequences are RNA. In some embodiments, the 10 oligonucleotide sequences are synthesized. In some embodiments, the ultramer oligonucleotide comprises about or at least about 10, 20, 30, 40, 50, 60, 70, 80, 90, 100, 200, 300, 400, or 500 oligonucleotide sequences. In some embodiments, the ultramer oligonucleotide comprises up to about 10, 20, 30, 40, 50, 60, 70, 80, 90, 100, 200, 300, 400, or 500 oligonucleotide sequences. In some embodiments, the 10 oligonucleotide sequences comprise a domain of nucleotides from 10 to 20 nucleotides in length with different sequences that are present in one or more microbial, pathogen, bacterial, viral, fungal, or parasitic genomes.

In another aspect, the present disclosure provides a method of generating a collection of oligonucleotides, the method comprising: (a) providing an ultramer oligonucleotide disclosed herein; and (b) hydrolyzing the ultramer oligonucleotide, thereby generating a collection of oligonucleotides. In some embodiments, step (b) comprises hydrolyzing an apurinic/apyrimidinic site in the ultramer. In some embodiments, step (b) is performed using endonuclease IV or endonuclease VII. In some embodiments, the method further comprises hydrolyzing a uracil residue in the ultramer oligonucleotide to form an apurinic/apyrimidinic site. In some embodiments, the hydrolyzing a uracil residue is performed using a uracil DNA glycosylase. In some embodiments, the method further comprises biotinylating the oligonucleotides in the collection of oligonucleotides. In some embodiments, the biotinylating is performed enzymatically (e.g., using T4 Polynucleotide Kinase) or chemically. In some embodiments, the method further comprises attaching a probe to the oligonucleotides in the collection of oligonucleotides. In some embodiments, the probe is digoxigenin or a fluorescent probe.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 shows nucleosome depletion by nucleosome-specific antibodies.

FIG. 9A shows an exemplary ultramer oligonucleotide design. FIG. 9B shows an ultramer oligonucleotide containing oligonucleotide sequences with an N mixed base. FIG. 9C shows an ultramer oligonucleotide containing oligonucleotide sequences with two N mixed bases. FIG. 9D shows an ultramer oligonucleotide containing oligonucleotide sequences with two mixed bases.

FIG. 11A shows representative oligonucleotides with mixed-base sites. FIG. 11B shows an analysis of non-human 13-mer probe pool grouped according to degree of degeneracy.

DETAILED DESCRIPTION OF THE INVENTION

General Overview

This disclosure provides novel and fast approaches for enriching pathogen nucleic acids in patient samples in which an overwhelmingly high proportion of the sample is made up of the patient's own nucleic acids. Since this disclosure enables detection of multiple pathogen nucleic acids in a sample, pathogens may be detected even in hypothesis-blind situations, such as situations in which a patient's caregiver has no clear idea or suspicion of what pathogen may have infected the patient. In general, the compositions and methods provided herein are designed to enrich biological samples containing nucleic acids in order to increase the representation of pathogen nucleic acids when compared to nucleic acids from the host. Enrichment of the pathogen nucleic acids within a sample may reduce the time and cost associated with analysis of the sample, particularly when the analysis involves a sequencing reaction.

This disclosure provides several ways of performing the enrichment. In some instances, this disclosure provides methods for producing novel collections of oligonucleotides that preferentially bind to sets of non-host nucleic acids in a sample. The collections of oligonucleotides can be used to preferentially detect non-host nucleic acids in multiple different types of molecular biology assays. For example, the collections of oligonucleotides may be used as primers in primer extension reactions, PCR reactions, or reverse-transcription reactions. In addition, the collections of oligonucleotides may be used in hybridization and/or pull-down assays to preferentially bind and isolate pathogen nucleic acids. In some cases, the collections of oligonucleotides may be used not only to enrich for pathogen nucleic acids, but also add a tag to such nucleic acids.

Additional enrichment techniques are also provided herein; such techniques can be used singly or in combination with the collections of oligonucleotides or with another method of enrichment. Examples of such additional enrichment techniques include: (a) self-hybridization techniques in which the major population in a sample of nucleic acids self-hybridizes more rapidly than the minor population in the sample; (b) depletion of nucleosome-associated DNA from free DNA; (c) removing and/or isolating DNA of specific length intervals; (d) exosome depletion or enrichment; and (e) strategic capture of regions of interest.

The enrichment approaches provided herein are particularly well-suited for detecting microbial nucleic acids such as circulating or circulating cell-free microbial nucleic acids present in blood samples from infected patients. They are also useful in any other context involving detection of minor populations of nucleic acids in a mixture dominated by a major population.

Figure 1:
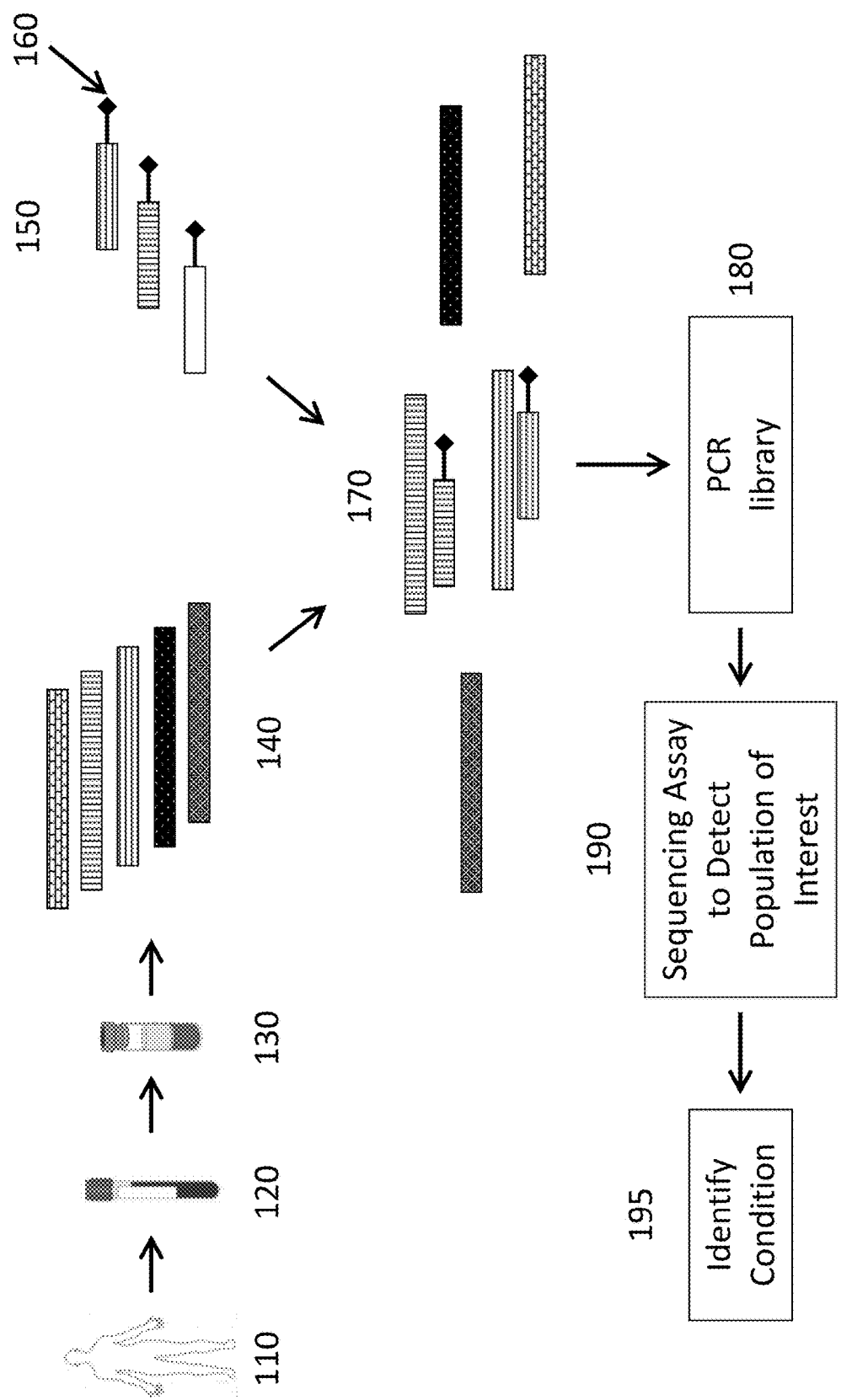
FIG. 1 shows a priming strategy using a collection of oligonucleotides to enrich a population of nucleic acids.

FIG. 1 provides a general method disclosed herein to detect pathogen or other non-human nucleic acids within a human patient sample. In some instances, a blood sample (120) or plasma sample (130) is obtained from a human patient (110) infected with (or suspected of being infected with) pathogens (e.g., microbes, bacteria, viruses, fungi, or parasites). The blood sample may contain nucleic acids such as circulating cell-free nucleic acids (140) which may be contacted with a collection of oligonucleotides (150) provided herein. The collection of oligonucleotides may preferentially bind to pathogen or non-human nucleic acid sequences (170). The collection of oligonucleotides may be linked to a label (160) which may comprise a nucleic acid label, barcode, sample-specific barcode, universal primer sequence, sequencing primer binding site, primer binding site to enable amplification of the barcode, sequencer-compatible sequence, and/or an adapter (e.g., sequencing adapter). In some cases, where a nucleic acid sample comprises RNA, the collection of oligonucleotides may be used to prime cDNA synthesis from an RNA template (170), in order to preferentially prime non-host RNA. In some cases, a collection of oligonucleotides may be used in a primer extension reaction (170) to preferentially prime pathogen DNA sequences within the sample. The primer extension reaction may also append overhang sequences to the pathogen nucleic acids. For example, sequences within the label (160) (e.g., adapter, barcode, etc.) may be appended to the pathogen nucleic acid via the primer extension reaction. A PCR reaction may be conducted to prepare the final library (180), which may be subjected to a sequencing assay (190) to aid in the detection and identification of pathogen species within the sample (195).

Figure 2:
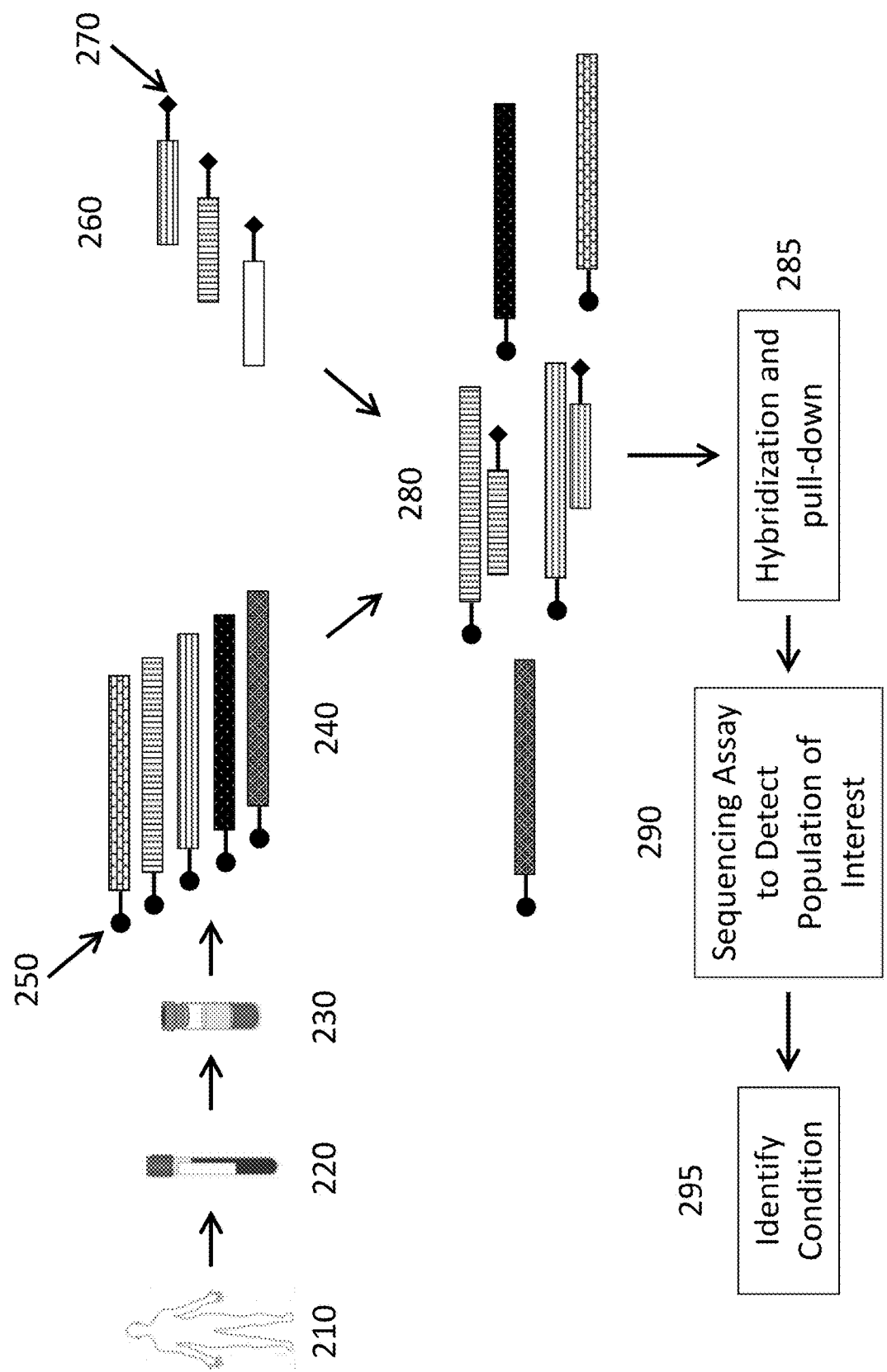
FIG. 2 shows a pull-down strategy using a collection of oligonucleotides to enrich a population of nucleic acids.

FIG. 2 shows steps in another method provided herein involving hybridization and pull-down steps. A sample may be provided as in FIG. 1 (210, 220, 230). The sample may be used to prepare a sequencing-ready library, and the nucleic acids within the sample (240) may be tagged with a label (250). The sample may be contacted with a collection of oligonucleotides (260), each of which may be conjugated to a label such as a biotin tag (270). The oligonucleotides may hybridize to the non-human sequences within the sample (280, 285) and then may be preferentially pulled down in a pull-down assay using, for example, avidin or streptavidin attached to a solid support (285). The library may then be sequenced (290) in order to identify the non-host species (e.g., pathogens) within the infected host (e.g., human) (295).

The methods and compositions provided herein provide many advantages over current methods of detecting minor populations of interest nucleic acids in a complex mixture. One advantage is that they alleviate sequencing costs by reducing library size or the number of sequence reads that are analyzed. Also, using targeted oligonucleotides such as the collections of oligonucleotides provided herein may speed the process of priming, capturing or amplifying a minor population, particularly when compared to other methods such as methods that rely on depleting the background population nucleic acids (e.g., human nucleic acids from the sample). They can be used to dramatically increase the sensitivity and specificity of detecting particular populations (e.g., pathogens or microbes) in a sample. Additionally, the collections of oligonucleotides can be used to produce DNA or RNA sequencing libraries; in some cases, they can be used to produce both DNA and RNA sequencing libraries from the same sample. As a result, the methods and compositions provided herein provide new, efficient approaches to detecting infectious diseases including pneumonia, tuberculosis, HIV infection, hepatitis infection (e.g., Hep A, B, or C), sepsis, human papilloma virus (HPV) infection, chlamydial infection, syphilitic infection, Ebola infection, multi-drug resistant infections, *Staphylococcus aureus* infections, enterococcus infections and influenza. In another example, the methods and compositions may be used to monitor the presence of one or more microbes, e.g., in the microbiome, in a host, who may or may not be experiencing symptoms associated with infection.

Collections of Oligonucleotides for Sequence Enrichment

This disclosure provides collections of oligonucleotides that are useful for enriching, capturing, or priming a particular population of nucleic acids (a "population of interest") within a complex mixture of nucleic acids. The population of interest may be non-host nucleic acids (e.g., non-human, microbial, or pathogen nucleic acids) in a population containing both host (e.g., human) and non-host nucleic acids. Often, the population of interest makes up a minor portion of a complex mixture of nucleic acids that may comprise another population of nucleic acids (a "background" population, e.g., host nucleic acids) that makes up a greater portion of the complex mixture of nucleic acids. In some cases, the methods and compositions provided herein are particularly useful when the population of interest makes up at most 1% or 0.1% of the total nucleic acids in the sample.

Generally, the methods provided herein involve using oligonucleotides in order to prime, capture or enrich for a population of interest. Often, the population of interest has a particular attribute or characteristic, and the oligonucleotides are designed to prime, capture or enrich for the population of interest and not to prime, capture or enrich for another population (e.g., "background" population) that may constitute a majority of the total population of nucleic acids. For example, the population of interest may be a subset of non-host (e.g., non-mammalian, non-human, pathogen, microbe, virus, bacteria, fungus, or parasite) nucleic acids in a population containing both host and non-host nucleic acids. In some cases, the oligonucleotides may be designed to remove, segregate, isolate, or deplete a background population (e.g., human nucleic acids), thereby enriching for the population of interest (e.g., non-human nucleic acids). In some cases, the oligonucleotides may comprise domains of nucleotides with sequences that may match (either completely or substantially) or may be complementary (either completely or substantially) to certain population of interest sequences (e.g., non-human nucleic acid sequences).

The collections of oligonucleotides provided herein may comprise nucleic acids sequences capable of binding or recognizing a population of interest. The collection of oligonucleotides may be used to specifically target and detect a population of interest in a sample, e.g., a sample comprising nucleic acids from a background population (e.g., host or human) and a population of interest (e.g., non-host or non-human). For example, the collection of oligonucleotides may be used as primers to specifically prime, capture, amplify, replicate or detect non-host nucleic acids in a sample comprising both host and non-host nucleic acids. More specifically, in some cases, they can be used to prime cDNA synthesis from an RNA template present in a sample. In some cases, they can be used in primer extension reactions in order to append a nucleic acid label or sequence to a target sequence. In some cases, they can be used as baits to capture non-host sequences from a library of DNA, cDNA, or RNA. The primed, amplified, or captured non-host nucleic acids may be identified by any method known in the art such as by conducting a sequencing assay, particularly a high-throughput sequencing assay, a Next Generation sequencing platform, a massively parallel sequencing platform, a Nanopore sequencing assay, or another sequencing assay known in the art.

A collection of oligonucleotides may comprise one or more oligonucleotides. In some cases, the collection of oligonucleotides may comprise about 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; $10^7$; $5 \times 10^7$; $10^8$; $5 \times 10^8$; or $10^9$ oligonucleotides. In some cases, the collection of oligonucleotides may comprise up to 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; $10^7$; $5 \times 10^7$; $10^8$; $5 \times 10^8$; or $10^9$ oligonucleotides. In some cases, the collection of oligonucleotides may comprise at least 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $3.5 \times 10^6$; $4 \times 10^6$; $4.5 \times 10^6$; $5 \times 10^6$; $5.5 \times 10^6$; $6 \times 10^6$; $6.5 \times 10^6$; $7 \times 10^6$; $7.5 \times 10^6$; $8 \times 10^6$; $8.5 \times 10^6$; $9 \times 10^6$; $9.5 \times 10^6$; $10^7$; $5 \times 10^7$; $10^8$; $5 \times 10^8$; or $10^9$ oligonucleotides.

Oligonucleotides in a collection of oligonucleotides may have the same or different lengths. In some cases, two or more oligonucleotides in the collection of oligonucleotides have the same length. In some cases, all oligonucleotides in the collection of oligonucleotides have the same length. In some cases, oligonucleotides in the collection of oligonucleotides have different lengths. In some cases, oligonucleotides in the collection of oligonucleotides have about 1, 2, 3, 4, 5, 6, 7, 8, 9, 10, 11, 12, 13, 14, 15, or 20 different lengths. In some cases, the oligonucleotides in the collection of oligonucleotides have up to 1, 2, 3, 4, 5, 6, 7, 8, 9, 10, 11, 12, 13, 14, 15, or 20 lengths. In some cases, the oligonucleotides in the collection of oligonucleotides have at least 1, 2, 3, 4, 5, 6, 7, 8, 9, 10, 11, 12, 13, 14, 15, or 20 lengths.

In some cases, the oligonucleotide may be about 10, 11, 12, 13, 14, 15, 16, 17, 18, 19, 20, 21, 22, 23, 24, 25, 30, 40, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, or 1,000 nucleotides in length. In some cases, the oligonucleotide may be up to 10, 11, 12, 13, 14, 15, 16, 17, 18, 19, 20, 21, 22, 23, 24, 25, 30, 40, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, or 1,000 nucleotides in length. In some cases, the oligonucleotide may be at least 10, 11, 12, 13, 14, 15, 16, 17, 18, 19, 20, 21, 22, 23, 24, 25, 30, 40, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, or 1,000 nucleotides in length. In some cases, the oligonucleotide may be from 10-1,000, 10-500, 10-400, 10-300, 10-200, 10-100, 10-90, 10-80, 10-70, 10-60, 10-50, 10-40, 10-30, 10-20, 10-15, 11-1,000, 11-500, 11-400, 11-300, 11-200, 11-100, 11-90, 11-80, 11-70, 11-60, 11-50, 11-40, 11-30, 11-20, 11-15, 12-1,000, 12-500, 12-400, 12-300, 12-200, 12-100, 12-90, 12-80, 12-70, 12-60, 12-50, 12-40, 12-30, 12-20, 12-15, 13-1,000, 13-500, 13-400, 13-300, 13-200, 13-100, 13-90, 13-80, 13-70, 13-60, 13-50, 13-40, 13-30, 13-20, 13-15, 13-14, 14-1,000, 14-500, 14-400, 14-300, 14-200, 14-100, 14-90, 14-80, 14-70, 14-60, 14-50, 14-40, 14-30, 14-20, or 14-15 nucleotides in length.

Oligonucleotides in a collection of oligonucleotides may have different nucleotide sequences. In some cases, the collection of oligonucleotides may comprise about 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides with different nucleotide sequences. In some cases, the collection of oligonucleotides may comprise up to 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides with different nucleotide sequences. In some cases, the collection of oligonucleotides may comprise at least 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides with different nucleotide sequences.

Oligonucleotides with different sequences may be present in multiple copies in a collection of oligonucleotides. A collection of oligonucleotides may contain oligonucleotides with identical nucleotide sequences. In some cases, the collection of oligonucleotides may comprise about 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 copies of an identical nucleotide sequence. In some cases, the collection of oligonucleotides may comprise up to 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 copies of an identical nucleotide sequence. In some cases, the collection of oligonucleotides may comprise at least 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 copies of an identical nucleotide sequence.

In some cases, one or more oligonucleotides within the collection of oligonucleotides are unlabeled; in some cases, one or more oligonucleotides within the collection of oligonucleotides are labeled. In some cases, one or more oligonucleotides are labeled, e.g., with a nucleic acid label, a chemical label, or an optical label. In some cases, one or more oligonucleotides are conjugated to a solid support. In some cases, one or more oligonucleotides are not conjugated to a solid support. In some cases, a label may be attached at the 5' or 3' end of an oligonucleotide or internally within an oligonucleotide. In some cases, one or more oligonucleotides within the collection of oligonucleotides are labeled with more than one label.

An oligonucleotide may comprise a nucleic acid label. In some cases, a nucleic acid label may comprise one or more of the following: barcode (e.g., sample barcode), universal primer sequence, primer binding site (e.g., for sequencing or to read a barcode, including, but not limited to, DNA sequencing primer binding site, sample barcode sequencing primer binding site, and amplification primer binding site compatible with various sequencing platform requirements), sequencer-compatible sequence, sequence to attach to a sequencing platform, sequencing adapter sequence, or adapter. Nucleic acid labels may be attached to the oligonucleotide (e.g., by ligation, or by synthetic design). In some cases, the length of a nucleic acid label is included in the length of an oligonucleotide. In some cases, the length of a nucleic acid label is not included in the length of an oligonucleotide.

An oligonucleotide may comprise a chemical label. Some non-limiting examples of a chemical label include biotin, avidin, streptavidin, radiolabel, polypeptide, and polymers. An oligonucleotide may comprise an optical label. Some non-limiting examples of an optical label include a fluorophore, fluorescent protein, dye, and quantum dot. An oligonucleotide may be conjugated to a solid support. In some cases, an oligonucleotide is not conjugated to a solid support. Some non-limiting examples of a solid support include a bead, magnetic bead, polymer, slide, chip, surface, plate, channel, cartridge, microfluidic device, and microarray. One or more oligonucleotides may be conjugated to a solid support for affinity chromatography. In some cases, each oligonucleotide has a different label. In some cases, each oligonucleotide has the same label. In some cases, each copy of an oligonucleotide has the same label. In some cases, each oligonucleotide with a different sequence has a different label.

The oligonucleotides provided herein generally comprise one or more nucleotides. In some cases, a nucleotide may be a deoxyribonucleotide (e.g., A, C, G, or T), ribonucleotide (e.g., A, C, G, or U), modified nucleotide, or synthetic nucleotide. In some cases, an oligonucleotide may comprise DNA, RNA, cDNA, dsDNA, ssDNA, mRNA, or cRNA. In some cases, an oligonucleotide may comprise DNA or RNA. In some cases, an oligonucleotide may comprise DNA and RNA. In some cases, an oligonucleotide may comprise DNA. In some cases, an oligonucleotide may comprise RNA. In some cases, an oligonucleotide may comprise modified or synthetic nucleotides. In some cases, an oligonucleotide may comprise one or more modified or synthetic nucleic acids, such as peptide nucleic acid (PNA), locked nucleic acid (LNA), or bridged nucleic acid (BNA). In some cases, an oligonucleotide may comprise DNA, RNA, PNA, LNA, BNA, or any combination thereof. In some cases, an oligonucleotide does not comprise an artificially fragmented nucleic acid. In some cases, a collection of oligonucleotides does not comprise artificially fragmented nucleic acids. In some cases, an oligonucleotide comprises a synthesized nucleic acid (e.g., by DNA synthesis). In some cases, a collection of oligonucleotides comprises synthesized nucleic acids (e.g., by DNA synthesis). In some cases, a collection of oligonucleotides may be lyophilized or dried. In some cases, a collection of oligonucleotides may comprise water or a buffered solution (e.g., an aqueous buffered solution).

In some cases, the oligonucleotide may contain about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, 1,000, or more PNA, LNA, and/or BNA linkages. In some cases, the oligonucleotide may contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 91, 92, 93, 94, 95, 96, 97, 98, 99, or 100% PNA, LNA, and/or BNA linkages.

Domains of Nucleotides

An oligonucleotide may comprise one or more domains of nucleotides. In some cases, the oligonucleotide comprises one domain of nucleotides. In some cases, the domain of nucleotides is the oligonucleotide. In some cases, the portion of the oligonucleotide with different nucleotide sequences appears within a domain of nucleotides. In some cases, the portion of the oligonucleotide with different nucleotide sequences makes up the entire oligonucleotide. In some cases, the portion of the oligonucleotide with different nucleotide sequences makes up a subset of the oligonucleotide such as a domain of nucleotides within the oligonucleotide. In some cases, a collection of oligonucleotides may comprise oligonucleotides, wherein the oligonucleotides comprise a domain of nucleotides with different sequences, wherein the oligonucleotides may be present in multiple copies. In some cases, a domain of nucleotides does not comprise an artificially fragmented nucleic acid. In some cases, a domain of nucleotides is synthesized (e.g., by DNA synthesis).

In some cases, a collection of oligonucleotides may comprise oligonucleotides, wherein each oligonucleotide comprises a domain of nucleotides that has a different nucleotide sequence. In some cases, the collection of oligonucleotides may comprise about 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides, wherein each oligonucleotide comprises a domain of nucleotides that has a different nucleotide sequence. In some cases, the collection of oligonucleotides may comprise up to 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides, wherein each oligonucleotide comprises a domain of nucleotides that has a different nucleotide sequence. In some cases, the collection of oligonucleotides may comprise at least 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; $10^6$; $1.1 \times 10^6$; $1.2 \times 10^6$; $1.3 \times 10^6$; $1.4 \times 10^6$; $1.5 \times 10^6$; $1.6 \times 10^6$; $1.7 \times 10^6$; $1.8 \times 10^6$; $1.9 \times 10^6$; $2 \times 10^6$; $2.1 \times 10^6$; $2.2 \times 10^6$; $2.3 \times 10^6$; $2.4 \times 10^6$; $2.5 \times 10^6$; $2.6 \times 10^6$; $2.7 \times 10^6$; $2.8 \times 10^6$; $2.9 \times 10^6$; $3 \times 10^6$; $4 \times 10^6$; $5 \times 10^6$; $6 \times 10^6$; $7 \times 10^6$; $8 \times 10^6$; $9 \times 10^6$; or $10^7$ oligonucleotides, wherein each oligonucleotide comprises a domain of nucleotides that has a different nucleotide sequence.

Oligonucleotides in a collection of oligonucleotides may comprise a domain of nucleotides with an identical nucleotide sequence. In some cases, the collection of oligonucleotides may comprise about 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 oligonucleotides containing a domain of nucleotides with an identical nucleotide sequence. In some cases, the collection of oligonucleotides may comprise up to 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 oligonucleotides containing a domain of nucleotides with an identical nucleotide sequence. In some cases, the collection of oligonucleotides may comprise at least 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 150; 200; 250; 300; 350; 400; 450; 500; 600; 700; 800; 900; or 1,000 oligonucleotides containing a domain of nucleotides with an identical nucleotide sequence.

In some cases, each oligonucleotide in a collection of oligonucleotides may comprise a domain of nucleotides that is not present in one or more background populations. In some cases, each oligonucleotide in a collection of oligonucleotides may comprise a domain of nucleotides that is not present in a host genome, exome, or transcriptome. In some cases, each oligonucleotide in a collection of oligonucleotides may comprise a domain of nucleotides that is not present in one or more vertebrate genomes, exomes, or transcriptomes. In some cases, each oligonucleotide in a collection of oligonucleotides may comprise a domain of nucleotides that is not present in one or more mammalian genomes, exomes, or transcriptomes. In some cases, each oligonucleotide in a collection of oligonucleotides may comprise a domain of nucleotides that is not present in one or more human genomes, exomes, or transcriptomes. In some cases, each oligonucleotide in a collection of oligonucleotides may comprise a domain of nucleotides that is not present in one or more human and one or more bacterial genomes, exomes, or transcriptomes. In some cases, each oligonucleotide in a collection of oligonucleotides may comprise a domain of nucleotides that is not present in one or more human and one or more viral genomes, exomes, or transcriptomes.

Figure 4:
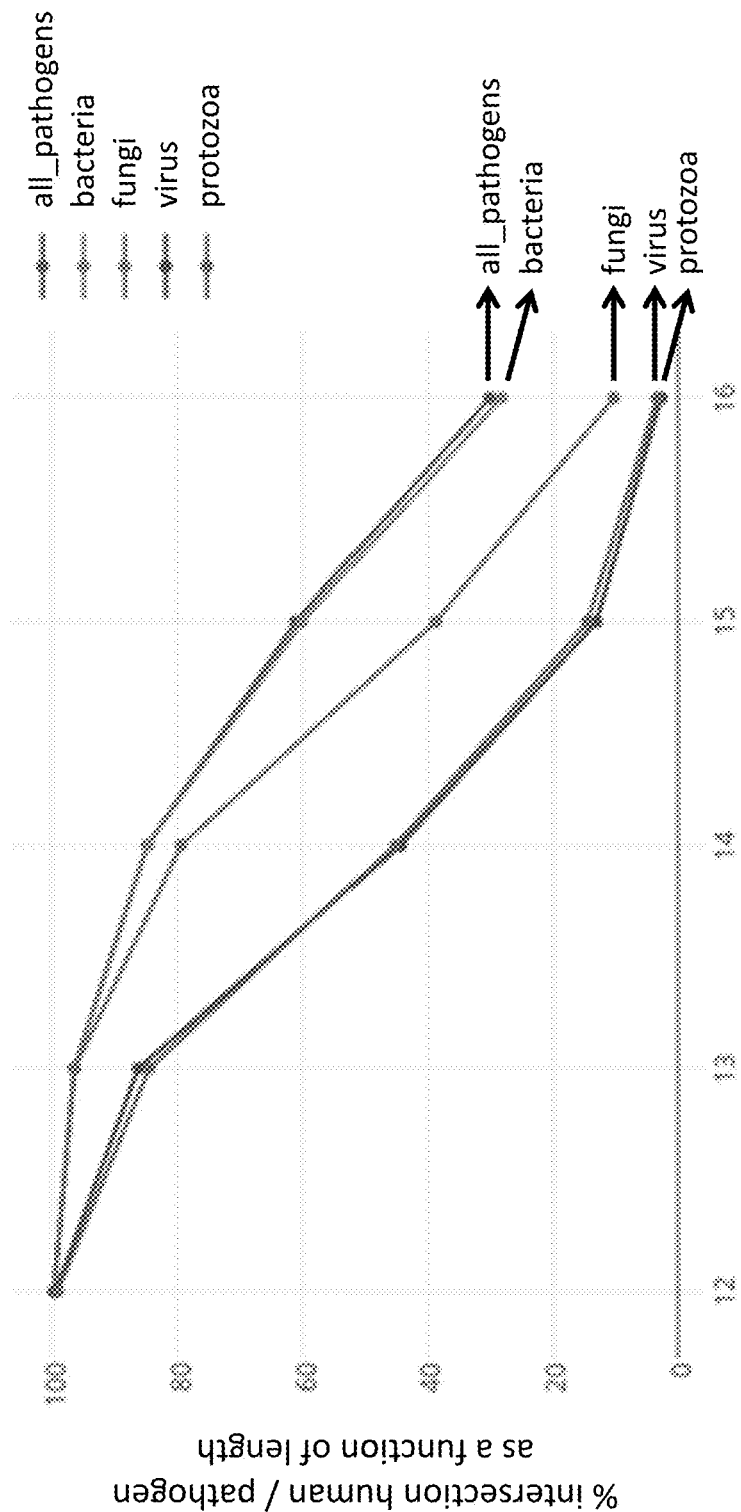
FIG. 4 shows length and sequence coverage of a domain of nucleotides. Approximately 96.5% of domains of nucleotides with length of 13 nucleotides are human.
Figure 5:
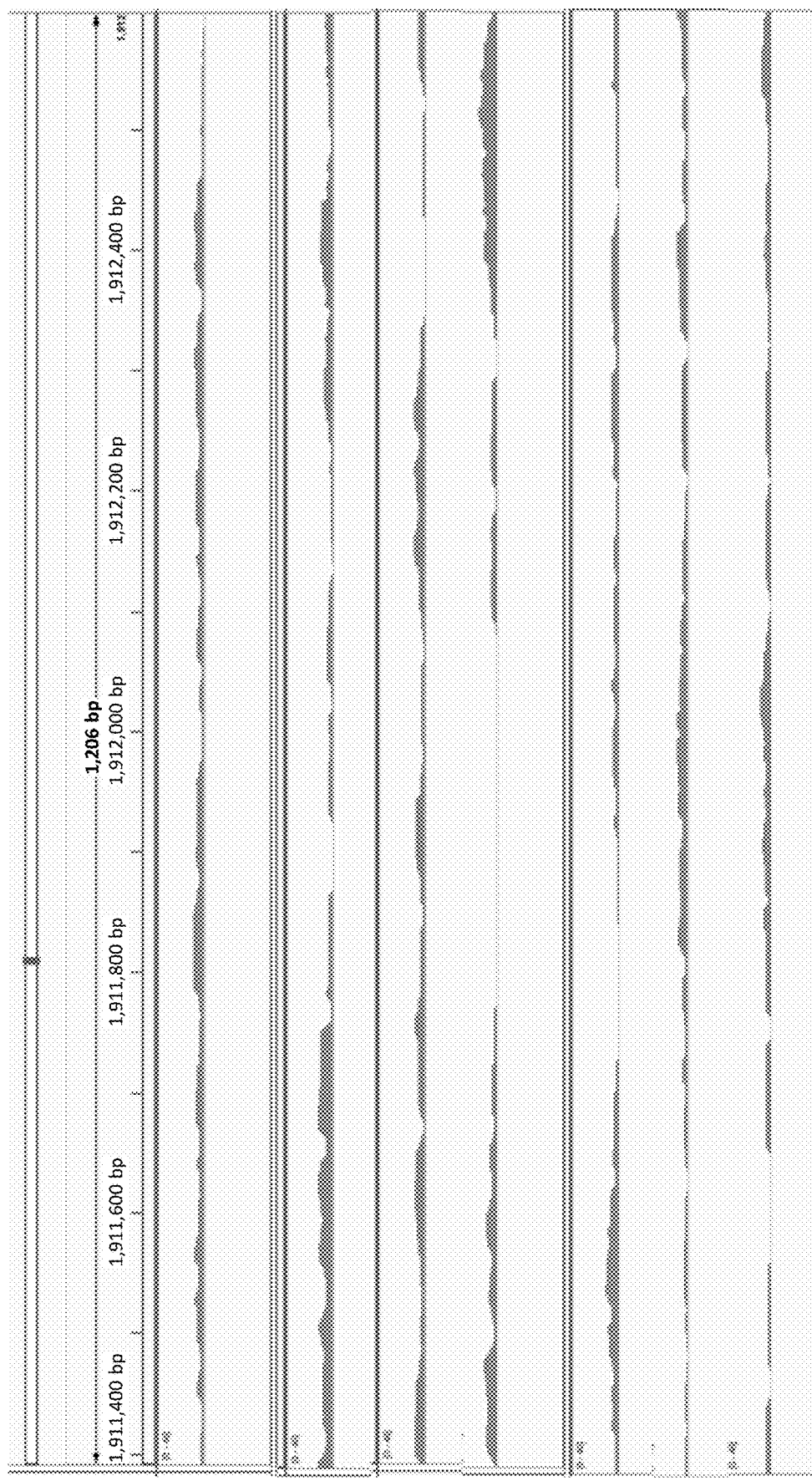
FIG. 5 shows estimated sequence coverage of a population of interest using a collection of oligonucleotides. Coverage of the *E. coli* genome is shown using a collection of oligonucleotides, wherein the oligonucleotides comprise domains of nucleotides with length of 13 nucleotides that are non-human.

In some cases, the domain of nucleotides may comprise nucleotide sequences that are identical to, nearly identical to, complementary to, or nearly complementary to one or more populations of interest. In some cases, the domains of nucleotides may comprise nucleotide sequences that are identical to, nearly identical to, complementary to, or nearly complementary to a subset of a populations of interest. In some cases, the domain of nucleotides may comprise nucleotide sequences that are identical to, nearly identical to, complementary to, or nearly complementary to about 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a population of interest. In some cases, the domain of nucleotides may comprise nucleotide sequences that are identical to, nearly identical to, complementary to, or nearly complementary to up to 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a population of interest. In some cases, the domain of nucleotides may comprise nucleotide sequences that are identical to, nearly identical to, complementary to, or nearly complementary to at least 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a population of interest. In some cases, the domain of nucleotides may comprise nucleotide sequences, wherein about 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are identical to, nearly identical to, complementary to, or nearly complementary to nucleic acids in a population of interest. In some cases, the domain of nucleotides may comprise nucleotide sequences, wherein up to 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are identical to, nearly identical to, complementary to, or nearly complementary to nucleic acids in a population of interest. In some cases, the domain of nucleotides may comprise nucleotide sequences, wherein at least 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are identical to, nearly identical to, complementary to, or nearly complementary to nucleic acids in a population of interest. In some cases, the domain of nucleotides may comprise nucleotide sequences that are not identical to, nearly identical to, complementary to, or nearly complementary to one or more populations of interest. In some cases, the domain of nucleotides may retain coverage of a population of interest, as shown in FIG. 4 and FIG. 5.

In some cases, the domain of nucleotides may comprise nucleotide sequences that are not identical to, nearly identical to, complementary to, or nearly complementary to one or more background populations. In some cases, the domain of nucleotides may comprise nucleotide sequences that are not identical to, nearly identical to, complementary to, or nearly complementary to a subset of a background populations. In some cases, the domain of nucleotides may comprise nucleotide sequences that are not identical to, nearly identical to, complementary to, or nearly complementary to about 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a background population. In some cases, the domain of nucleotides may comprise nucleotide sequences that are not identical to, nearly identical to, complementary to, or nearly complementary to up to 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a background population. In some cases, the domain of nucleotides may comprise nucleotide sequences that are not identical to, nearly identical to, complementary to, or nearly complementary to at least 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the nucleic acids in a background population. In some cases, the domain of nucleotides may comprise nucleotide sequences, wherein about 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are not identical to, nearly identical to, complementary to, or nearly complementary to nucleic acids in a background population. In some cases, the domain of nucleotides may comprise nucleotide sequences, wherein up to 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are not identical to, nearly identical to, complementary to, or nearly complementary to nucleic acids in a background population. In some cases, the domain of nucleotides may comprise nucleotide sequences, wherein at least 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of nucleotide sequences are not identical to, nearly identical to, complementary to, or nearly complementary to nucleic acids in a background population. In some cases, the domain of nucleotides may comprise nucleotide sequences that are identical to, nearly identical to, complementary to, or nearly complementary to one or more background populations.

In some cases, the domain of nucleotides may comprise nucleotide sequences that bind with a mismatch to one or more background population nucleic acids. In some cases, the domain of nucleotides may comprise nucleotide sequences that bind with 1, 2, 3, 4, 5, 6, 7, 8, 9, 10, 11, 12, 13, 14, 15, 16, 17, 18, 19, 20, 21, 22, 23, 24, or 25 mismatches to one or more background population nucleic acids. In some cases, the domain of nucleotides may comprise nucleotide sequences that bind with up to 1, 2, 3, 4, 5, 6, 7, 8, 9, 10, 11, 12, 13, 14, 15, 16, 17, 18, 19, 20, 21, 22, 23, 24, or 25 mismatches to one or more background population nucleic acids. In some cases, the domain of nucleotides may comprise nucleotide sequences that bind with at least 1, 2, 3, 4, 5, 6, 7, 8, 9, 10, 11, 12, 13, 14, 15, 16, 17, 18, 19, 20, 21, 22, 23, 24, or 25 mismatches to one or more background population nucleic acids.

Domains of nucleotides may be one or more lengths. In some cases, domains of nucleotides are a single length. In some cases, domains of nucleotides are different lengths. In some cases, the domain of nucleotides may be 10, 11, 12, 13, 14, 15, 16, 17, 18, 19, 20, 21, 22, 23, 24, or 25 nucleotides in length. In some cases, the domain of nucleotides is 13 or 14 nucleotides in length. In some cases, the domain of nucleotides is 13 nucleotides in length. In some cases, the domain of nucleotides is 14 nucleotides in length. In some cases, the domain of nucleotides may be up to 10, 11, 12, 13, 14, 15, 16, 17, 18, 19, 20, 21, 22, 23, 24, or 25 nucleotides in length. In some cases, the domain of nucleotides is up to 13 or 14 nucleotides in length. In some cases, the domain of nucleotides is up to 13 nucleotides in length. In some cases, the domain of nucleotides is up to 14 nucleotides in length. In some cases, the domain of nucleotides may be at least 10, 11, 12, 13, 14, 15, 16, 17, 18, 19, 20, 21, 22, 23, 24, or 25 nucleotides in length. In some cases, the domain of nucleotides is at least 13 or 14 nucleotides in length. In some cases, the domain of nucleotides is at least 13 nucleotides in length. In some cases, the domain of nucleotides is at least 14 nucleotides in length. In some cases, the domain of nucleotides may be from 10-20, 11-20, 12-20, 13-20, 14-20, 10-19, 10-18, 10-17, 10-16, 10-15, 10-14, 10-13, 11-19, 12-19, 13-19, 14-19, 11-18, 11-17, 11-16, 11-15, 11-14, 11-13, 12-18, 12-17, 12-16, 12-15, 12-14, 12-13, 13-18, 13-17, 13-16, 13-15, 13-14, 14-18, 14-17, 14-16, or 14-15 nucleotides in length. In some cases, the domain of nucleotides is 12-15 nucleotides in length. In some cases, the domain of nucleotides is 13-15 nucleotides in length. In some cases, the domain of nucleotides is 13-14 nucleotides in length. In some cases, the domain of nucleotides is a k-mer such as a 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, or 25-mer. In some cases, the domain of nucleotides is a 13-mer or 14-mer. In some cases, the domain of nucleotides is a 13-mer. In some cases, the domain of nucleotides is a 14-mer.

Background Population

As used herein, a background population is generally a population that is not a population of interest. A background population of nucleic acids may be used to produce a collection of oligonucleotides. For example, a background population of nucleic acids may be used to produce a collection of oligonucleotides capable of hybridizing to a population of interest (e.g., the background population nucleic acids can be used as "bait" to fish out oligonucleotides from a starting heterogeneous collection of oligonucleotides). In some cases, a background population is a population of nucleic acids in a sample. The methods and compositions provided herein may be used to preferentially remove or isolate the background population of nucleic acids in the sample; in some cases, the methods and compositions may be used to specifically target a population of interest in a preferential fashion such that the population of interest is isolated, removed, or detected but not necessarily the background population.

In some cases, the background population may be derived from (e.g., contain a sequence present in or identical to, nearly identical to, complementary to, or nearly complementary to) a sequence in the genome, exome, or transcriptome of a host organism or host. In some cases, a host may be a mammal, human, non-human mammal, a domesticated animal (e.g., laboratory animals, household pets, or livestock), or non-domesticated animal (e.g., wildlife). In some cases, the host may be a dog, cat, rodent, mouse, hamster, cow, bird, chicken, pig, horse, goat, sheep, rabbit, microbe, pathogen, bacteria, virus, fungus, or parasite. In some cases, the host is a mammal. In some cases, the host is a human. The host may be a patient. In some cases, the host may be treated with an antimicrobial, antibacterial, antiviral, or antiparasitic drug. In some cases, the host may have been treated or may be treated with an antimicrobial, antibacterial, antiviral, or antiparasitic drug. In some cases, the host is infected (e.g., with one or more microbes, pathogens, bacteria, viruses, fungi, or parasites). In some cases, the host is not infected (e.g., with one or more microbes, pathogens, bacteria, viruses, fungi, or parasites). In some cases, the host is healthy. In some cases, the host is susceptible or at risk of an infection.

In some cases, the background population may be derived from a dog, cat, rodent, mouse, hamster, cow, bird, chicken, pig, horse, goat, sheep, rabbit, microbe, pathogen, bacteria, virus, fungus, or parasite. In some cases, the background population is mammalian. In some cases, the background population is human. In some cases, the background population may be derived from a host. In some cases, the background population contains multiple populations, such as human and microbial populations of nucleic acids (e.g., human alone, human and viral, human and bacterial, human and fungal, human and parasitic, etc.).

In some cases, the background population may be one or more genomes, exomes, and/or transcriptomes. In some cases, the background population may be about 1, 2, 3, 4, 5, 6, 7, 8, 9, 10, 15, 20, 25, 30, 35, 40, 45, 50, 60, 70, 80, 90, or 100 genomes, exomes, and/or transcriptomes. In some cases, the background population may be up to 1, 2, 3, 4, 5, 6, 7, 8, 9, 10, 15, 20, 25, 30, 35, 40, 45, 50, 60, 70, 80, 90, or 100 genomes, exomes, and/or transcriptomes. In some cases, the background population may be at least 1, 2, 3, 4, 5, 6, 7, 8, 9, 10, 15, 20, 25, 30, 35, 40, 45, 50, 60, 70, 80, 90, or 100 genomes, exomes, and/or transcriptomes.

In some cases, the background population may be the mammalian genome, exome, or transcriptome from multiple individual mammals of the same species. In some cases, the background population may be the mammalian genome, exome, or transcriptome from multiple individual mammals of one or more species. In some cases, the background population may be the mammalian genome, exome, or transcriptome from one or more male and one or more female mammals of the same species. The background population may be mammalian genomic DNA and mammalian RNA. In some cases, the background population may be a mammalian genome, exome, or transcriptome and one or more microbial genomes, exomes, or transcriptomes. In some cases, the background population may be a mammalian genome, exome, or transcriptome and one or more pathogen genomes, exomes, or transcriptomes. In some cases, the background population may be a mammalian genome, exome, or transcriptome and one or more bacterial genomes, exomes, or transcriptomes. In some cases, the background population may be a mammalian genome, exome, or transcriptome and one or more viral genomes, exomes, or transcriptomes. In some cases, the background population may be a mammalian genome, exome, or transcriptome and one or more retroviral genomes, exomes, or transcriptomes. In some cases, the background population may be a mammalian genome, exome, or transcriptome and one or more viral and one or more bacterial genomes, exomes, or transcriptomes. In some cases, the background population may be a mammalian genome, exome, or transcriptome and one or more parasite genomes, exomes, or transcriptomes. In some cases, one or more may be about 1, 2, 3, 4, 5, 6, 7, 8, 9, 10, 15, 20, 25, 30, 35, 40, 45, 50, 60, 70, 80, 90, or 100. In some cases, one or more may be up to 1, 2, 3, 4, 5, 6, 7, 8, 9, 10, 15, 20, 25, 30, 35, 40, 45, 50, 60, 70, 80, 90, or 100. In some cases, one or more may be at least 1, 2, 3, 4, 5, 6, 7, 8, 9, 10, 15, 20, 25, 30, 35, 40, 45, 50, 60, 70, 80, 90, or 100. In some cases, the mammalian genome, exome, or transcriptome is a non-human genome, exome, or transcriptome.

In some cases, the mammalian genome, exome, or transcriptome is a human genome, exome, or transcriptome. In some cases, the background population is a human genome, exome, or transcriptome. In some cases, the background population may be the human genome, exome, or transcriptome from multiple individual humans. In some cases, the background population may be the human genome, exome, or transcriptome from one or more male and one or more female humans. The background population may be human genomic DNA and human RNA. In some cases, the background population may be a human genome, exome, or transcriptome and one or more microbial genomes, exomes, or transcriptomes. In some cases, the background population may be a human genome, exome, or transcriptome and one or more pathogen genomes, exomes, or transcriptomes. In some cases, the background population may be a human genome, exome, or transcriptome and one or more bacterial genomes, exomes, or transcriptomes. In some cases, the background population may be a human genome, exome, or transcriptome and one or more viral genomes, exomes, or transcriptomes. In some cases, the background population may be a human genome, exome, or transcriptome and one or more retroviral genomes, exomes, or transcriptomes. In some cases, the background population may be a human genome, exome, or transcriptome and one or more viral and one or more bacterial genomes, exomes, or transcriptomes. In some cases, the background population may be a human genome, exome, or transcriptome and one or more parasite genomes, exomes, or transcriptomes. In some cases, one or more may be about 1, 2, 3, 4, 5, 6, 7, 8, 9, 10, 15, 20, 25, 30, 35, 40, 45, 50, 60, 70, 80, 90, or 100. In some cases, one or more may be up to 1, 2, 3, 4, 5, 6, 7, 8, 9, 10, 15, 20, 25, 30, 35, 40, 45, 50, 60, 70, 80, 90, or 100. In some cases, one or more may be at least 1, 2, 3, 4, 5, 6, 7, 8, 9, 10, 15, 20, 25, 30, 35, 40, 45, 50, 60, 70, 80, 90, or 100.

In some cases, the background population may comprise about 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome. In some cases, the background population may comprise up to 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome. In some cases, the background population may comprise at least 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome.

In some cases, the background population may comprise about 0.01, 0.05, 0.1, 0.5, 1, 2, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, or 99.9% of the total population of nucleic acids in the sample. In some cases, the background population may comprise up to 0.01, 0.05, 0.1, 0.5, 1, 2, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, or 99.9% of the total population of nucleic acids in the sample. In some cases, the background population may comprise at least 0.01, 0.05, 0.1, 0.5, 1, 2, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, or 99.9% of the total population of nucleic acids in the sample.

In some cases, the background population may comprise DNA, RNA, cDNA, mRNA, cRNA, dsDNA, ssDNA, miRNA, circulating nucleic acids, circulating DNA, circulating RNA, cell-free nucleic acids, cell-free DNA, cell-free RNA, circulating cell-free DNA, circulating cell-free RNA, or genomic DNA. The background population may be a mixture of DNA and RNA. The background population may be genomic DNA. In some cases, the background population comprises artificially fragmented nucleic acids. In some cases, the background population does not comprise artificially fragmented nucleic acids. In some cases, the background population comprises synthesized nucleic acids (e.g., by DNA synthesis). In some cases, the background population nucleic acids are synthesized (e.g., by DNA synthesis). In some cases, the background population may be a genome, exome, or transcriptome.

In some cases, one or more nucleic acids in a background population are unlabeled; in some cases, one or more nucleic acids in a background population are labeled. In some cases, one or more nucleic acids in a background population are labeled, e.g., with a nucleic acid label, a chemical label, or an optical label. In some cases, one or more nucleic acids in a background population are conjugated to a solid support. In some cases, a label may be attached at the 5' or 3' end of a nucleic acid in a background population or internally within a nucleic acid in a background population. In some cases, one or more nucleic acids in a background population are labeled with more than one label.

A nucleic acid in a background population may comprise a nucleic acid label. In some cases, a nucleic acid label may comprise one or more of the following: barcode (e.g., sample barcode), universal primer sequence, primer binding site (e.g., for sequencing or to read a barcode, including, but not limited to, DNA sequencing primer binding site, sample barcode sequencing primer binding site, and amplification primer binding site compatible with various sequencing platform requirements), sequencer-compatible sequence, sequence to attach to a sequencing platform, sequencing adapter sequence, or adapter. Nucleic acid labels may be attached to the nucleic acid in a background population (e.g., by ligation, or by synthetic design). In some cases, the length of a nucleic acid label is included in the length of a nucleic acid in a background population. In some cases, the length of a nucleic acid label is not included in the length of a nucleic acid in a background population.

A nucleic acid in a background population may comprise a chemical label. Some non-limiting examples of a chemical label include biotin, avidin, streptavidin, radiolabel, polypeptide, and polymers. A nucleic acid in a background population may comprise an optical label. Some non-limiting examples of an optical label include a fluorophore, fluorescent protein, dye, and quantum dot. A nucleic acid in a background population may be conjugated to a solid support. Some non-limiting examples of a solid support include a bead, magnetic bead, polymer, slide, chip, surface, plate, channel, cartridge, microfluidic device, and microarray. The nucleic acid in a background population may be conjugated to a solid support for affinity chromatography. In some cases, each nucleic acid in a background population has a different label. In some cases, each nucleic acid in a background population has the same label. In some cases, each copy of a nucleic acid in a background population has the same label. In some cases, each nucleic acid in a background population with a different sequence has a different label.

Population of Interest

In general, a population of interest is a population with some feature distinguishing it from other components of larger population. A population of interest may be non-host nucleic acids (e.g., bacterial nucleic acids) present in a complex mixture of host and non-host nucleic acids.

In some cases, the population of interest may comprise DNA, RNA, cDNA, mRNA, cRNA, dsDNA, ssDNA, miRNA, circulating nucleic acids, circulating DNA, circulating RNA, cell-free nucleic acids, cell-free DNA, cell-free RNA, circulating cell-free DNA, circulating cell-free RNA, or genomic DNA. The population of interest may be a mixture of DNA and RNA. The population of interest may be genomic DNA. In some cases, the population of interest comprises artificially fragmented nucleic acids. In some cases, the population of interest does not comprise artificially fragmented nucleic acids. In some cases, the population of interest comprises synthesized nucleic acids (e.g., by DNA synthesis). In some cases, the population of interest is synthesized (e.g., by DNA synthesis). In some cases, the population of interest may be a genome, exome, or transcriptome.

In some cases, the population of interest is non-host. In some cases, non-host refers to organisms other than the host. In some cases, non-host refers to species other than the host. In some cases, non-host may refer to other organisms of the same species as the host. In some cases, non-host may be non-mammalian, non-human, non-dog, non-cat, non-rodent, non-mouse, non-hamster, non-cow, non-bird, non-chicken, non-pig, non-horse, non-goat, non-sheep, or non-rabbit. In some cases, non-host may be microbial, pathogen, bacterial, viral, fungal, parasite, or a combination thereof. In some cases, non-host is non-mammalian. In some cases, non-host is non-human. In some cases, non-host is non-patient.

In some cases, the population of interest may be non-mammalian or non-human. In some cases, the population of interest may be microbial, bacterial, viral, fungal, retroviral, pathogen, or parasitic. In some cases, the population of interest may be non-microbial, non-bacterial, non-viral, non-fungal, non-retroviral, non-pathogen, or non-parasite. In some cases, the population of interest may be derived from a microbe, pathogen, bacteria, virus, fungus, or parasite. In some cases, the population of interest is non-mammalian. In some cases, the population of interest is non-human. In some cases, the population of interest may be derived from a microbe or pathogen infecting a host. In some cases, the population of interest may be non-mammalian DNA or RNA. In some cases, the population of interest may be non-human DNA or RNA. In some cases, the population of interest may be microbial, bacterial, viral, fungal, retroviral, pathogen, or parasitic DNA or RNA. In some cases, the population of interest may be non-microbial, non-bacterial, non-viral, non-fungal, non-retroviral, non-pathogen, or non-parasite DNA or RNA.

In some cases, the population of interest may comprise one or more non-host genomes, exomes, or transcriptomes. In some cases, the population of interest may comprise about 1; 2; 3; 4; 5; 6; 7; 8; 9; 10; 15; 20; 25; 30; 35; 40; 45; 50; 60; 70; 80; 90; 100; 500; 1,000; 5,000; 10,000; 50,000; or 100,000 non-host genomes, exomes, or transcriptomes. In some cases, the population of interest may comprise up to 1; 2; 3; 4; 5; 6; 7; 8; 9; 10; 15; 20; 25; 30; 35; 40; 45; 50; 60; 70; 80; 90; 100; 500; 1,000; 5,000; 10,000; 50,000; or 100,000 non-host genomes, exomes, or transcriptomes. In some cases, the population of interest may comprise at least 1; 2; 3; 4; 5; 6; 7; 8; 9; 10; 15; 20; 25; 30; 35; 40; 45; 50; 60; 70; 80; 90; 100; 500; 1,000; 5,000; 10,000; 50,000; or 100,000 non-host genomes, exomes, or transcriptomes. In some cases, the population of interest may comprise the non-mammalian genome, exome, or transcriptome from multiple individuals of the same non-mammalian species. In some cases, the population of interest may comprise the non-mammalian genome, exome, or transcriptome from multiple individuals of one or more non-mammalian species. In some cases, the population of interest may comprise non-mammalian genomic DNA and non-mammalian RNA. In some cases, the population of interest may comprise one or more microbial genomes, exomes, or transcriptomes. In some cases, the population of interest may comprise one or more pathogen genomes, exomes, or transcriptomes. In some cases, the population of interest may comprise one or more bacterial genomes, exomes, or transcriptomes. In some cases, the population of interest may comprise one or more viral genomes, exomes, or transcriptomes. In some cases, the population of interest may comprise one or more retroviral genomes, exomes, or transcriptomes. In some cases, the population of interest may comprise one or more viral and one or more bacterial genomes, exomes, or transcriptomes. In some cases, the population of interest may comprise one or more parasite genomes, exomes, or transcriptomes. In some cases, one or more may be about 1, 2, 3, 4, 5, 6, 7, 8, 9, 10, 15, 20, 25, 30, 35, 40, 45, 50, 60, 70, 80, 90, or 100. In some cases, one or more may be up to 1, 2, 3, 4, 5, 6, 7, 8, 9, 10, 15, 20, 25, 30, 35, 40, 45, 50, 60, 70, 80, 90, or 100. In some cases, one or more may be at least 1, 2, 3, 4, 5, 6, 7, 8, 9, 10, 15, 20, 25, 30, 35, 40, 45, 50, 60, 70, 80, 90, or 100. In some cases, the non-mammalian genome, exome, or transcriptome is a non-human genome, exome, or transcriptome. In some cases, the non-mammalian genome, exome, or transcriptome is a microbial, bacterial, viral, fungal, retroviral, pathogen, or parasite genome, exome, or transcriptome.

A population of interest may include a portion of a genome, exome, or transcriptome. In some cases, the population of interest may comprise about 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome. In some cases, the population of interest may comprise up to 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome. In some cases, the population of interest may comprise at least 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of a genome, exome, or transcriptome.

A population of interest may account for a portion of a total population of nucleic acids in a sample. In some cases, the population of interest may comprise about 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, or 50% of the total population of nucleic acids in the sample. In some cases, the population of interest may comprise up to 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, or 50% of the total population of nucleic acids in the sample. In some cases, the population of interest may comprise at least 0.000001, 0.000005, 0.00001, 0.00005, 0.0001, 0.0005, 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, or 50% of the total population of nucleic acids in the sample.

The background population nucleic acids may be present in excess quantities relative to the population of interest nucleic acids in a sample. The ratio of background population to population of interest nucleic acids may be about 1; 2; 3; 4; 5; 6; 7; 8; 9; 10; 11; 12; 13; 14; 15; 16; 17; 18; 19;

20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; 1,000,000; 2,000,000; 3,000,000; 4,000,000; 5,000,000; 6,000,000; 7,000,000; 8,000,000; 9,000,000; or 10,000,000. The ratio of background population to population of interest nucleic acids may be up to 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; 1,000,000; 2,000,000; 3,000,000; 4,000,000; 5,000,000; 6,000,000; 7,000,000; 8,000,000; 9,000,000; or 10,000,000. The ratio of background population to population of interest nucleic acids may be at least 1; 2; 3; 4; 5; 6; 7; 8; 9; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; 10,000; 20,000; 30,000; 40,000; 50,000; 60,000; 70,000; 80,000; 90,000; 100,000; 200,000; 300,000; 400,000; 500,000; 600,000; 700,000; 800,000; 900,000; 1,000,000; 2,000,000; 3,000,000; 4,000,000; 5,000,000; 6,000,000; 7,000,000; 8,000,000; 9,000,000; or 10,000,000. The ratio may be calculated in terms of concentration, moles, or mass.

A population of interest may include nucleic acids derived from one or more species. In some cases, the population of interest may comprise nucleic acids derived from about 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, the population of interest may comprise nucleic acids derived from up to 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, the population of interest may comprise nucleic acids derived from at least 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, the species is a non-mammalian species. In some cases, the species is a non-human species. In some cases, the species is a microbe, bacteria, virus, fungus, retrovirus, pathogen, or parasite. In some cases, the population of interest may comprise nucleic acids derived from about 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, the population of interest may comprise nucleic acids derived from up to 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, the population of interest may comprise nucleic acids derived from at least 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, the population of interest may comprise at least one nucleic acid derived from about 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, the population of interest may comprise at least one nucleic acid derived from up to 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, the population of interest may comprise at least one nucleic acid derived from at least 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, the population of interest may comprise at least one nucleic acid derived from about 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species. In some cases, the population of interest may comprise at least one nucleic acid derived from up to 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species. In some cases, the population of interest may comprise at least one nucleic acid derived from at least 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species.

In some cases, one or more nucleic acids in a population of interest are unlabeled; in some cases, one or more nucleic acids in a population of interest are labeled. In some cases, one or more nucleic acids in a population of interest are labeled, e.g., with a nucleic acid label, a chemical label, or an optical label. In some cases, one or more nucleic acids in a population of interest are conjugated to a solid support. In some cases, a label may be attached at the 5' or 3' end of a nucleic acid in a population of interest or internally within a nucleic acid in a population of interest. In some cases, one or more nucleic acids in a population of interest are labeled with more than one label.

A nucleic acid in a population of interest may comprise a nucleic acid label. In some cases, a nucleic acid label may comprise one or more of the following: barcode (e.g., sample barcode), universal primer sequence, primer binding site (e.g., for sequencing or to read a barcode, including, but not limited to, DNA sequencing primer binding site, sample barcode sequencing primer binding site, and amplification primer binding site compatible with various sequencing platform requirements), sequencer-compatible sequence, sequence to attach to a sequencing platform, sequencing adapter sequence, or adapter. Nucleic acid labels may be attached to the nucleic acid in a population of interest (e.g., by ligation, or by synthetic design). In some cases, the length of a nucleic acid label is included in the length of a nucleic acid in a population of interest. In some cases, the length of a nucleic acid label is not included in the length of a nucleic acid in a population of interest.

A nucleic acid in a population of interest may comprise a chemical label. Some non-limiting examples of a chemical label include biotin, avidin, streptavidin, radiolabel, polypeptide, and polymers. A nucleic acid in a population of interest may comprise an optical label. Some non-limiting examples of an optical label include a fluorophore, fluorescent protein, dye, and quantum dot. A nucleic acid in a population of interest may be conjugated to a solid support. Some non-limiting examples of a solid support include a bead, magnetic bead, polymer, slide, chip, surface, plate, channel, cartridge, microfluidic device, and microarray. The nucleic acid in a population of interest may be conjugated to a solid support for affinity chromatography. In some cases, each nucleic acid in a population of interest has a different label. In some cases, each nucleic acid in a population of interest has the same label. In some cases, each copy of a nucleic acid in a population of interest has the same label. In some cases, each nucleic acid in a population of interest with a different sequence has a different label.

Some non-limiting examples of a microorganism or microbe that can be detected by the methods provided herein include bacteria, archaea, protozoa, protists, fungus, algae, virus, retrovirus, pathogen, or parasite. In some cases, the microorganism or microbe is a prokaryote. In some cases, the microorganism or microbe is a eukaryote. Some non-limiting examples of bacteria include *Bacillus, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Staphyloccus Aures, Streptococcus, Treponema, Vibrio,* and *Yersinia*. Some non-limiting examples of fungi include *Candida, Aspergillus, Cryptococcus, Histoplasma, Pneumocystis,* and *Stachybotrys*. In some instances, the microbe or microorganism detected by the methods provided herein is a drug-resistant microbe or multi-drug resistant pathogen. Non-limiting examples of drug-resistant or multi-drug resistant pathogens include: In some cases, drug-resistant strains of *Clostridium difficile (C. difficile)*, carbapenem-resistant *Enterobacteriaceae* (CRE), drug-resistant Neisseria, gonorrhoeae (cephalosporin resistant), multidrug-resistant *Acinetobacter*, drug-resistant *Campylobacter*, fluconazole-resistant *Candida* (a fungus), extended spectrum β-lactamase producing *Enterobacteriaceae* (ESBLs), vancomycin-resistant *Enterococcus* (VRE), multidrug-resistant *Pseudomonas aeruginosa*, drug-resistant non-typhoidal *Salmonella*, drug-resistant *Salmonella Typhi*, drug-resistant *Shigella*, methicillin-resistant *Staphylococcus aureus* (MRSA), drug-resistant *Streptococcus pneumonia*, drug-resistant *tuberculosis* (MDR and XDR), multi-drug resistant *Staphylococcus aureus*, vancomycin-resistant *Staphylococcus aureus* (VRSA), erythromycin-resistant *Streptococcus* Group A, or clindamycin-resistant *Streptococcus* Group B.

In some cases, the methods and compositions provided herein may be used to detect a virus such as a retrovirus or lentivirus. In some cases, the virus is a member of Group I, Group II, Group III, Group IV, Group V, Group VI, or Group VII in the Baltimore virus classification system. In some cases, a virus is a member of the family Adenoviridae, Anelloviridae, Arenaviridae, Astroviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Papovaviridae, Paramyxoviridae, Parvoviridae, Picornaviridae, Polyomaviridae, Poxviridae, Reoviridae, Retroviridae, Rhabdoviridae, or Togaviridae. In some cases, a virus is *Adenovirus, Amur virus, Andes virus, Animal virus, Astrovirus, Avian nephritis virus, Avian orthoreovirus, Avian Reovirus, Banna virus, Bas-Congo virus, Bat-borne virus, BK virus, Blueberry shock virus, Chicken anaemia virus, Bovine adenovirus, Bovine coronavirus, Bovine herpesvirus 4, Bovine parvovirus, Bulbul coronavirus HKU11, Carrizal virus, Catacamas virus, Chandipura virus, Channel catfish virus, Choclo virus, Coltivirus, Coxsackievirus, Cricket paralysis virus, Crimean-Congo hemorrhagic fever virus, Cytomegalovirus, dengue virus, Dobrava-Belgrade virus, Ebola virus, Ebolavirus, El Moro Canyon virus, Elephant endotheliotropic herpesvirus, Epstein-Barr virus, Feline leukemia virus, Foot-and-mouth disease virus, Gou virus, Guanarito virus, Hantaan River virus, Hantavirus, HCoV-EMC/2012, Hendra virus, Henipavirus, Hepatitis A virus, Hepatitis B virus, Hepatitis C virus, Hepatitis D, Hepatitis E virus, Herpes simplex type 1, Herpes simplex type 2, Herpes simplex virus type 1, Herpes simplex virus type 2, HIV, Human astrovirus, Human bocavirus, Human cytomegalovirus, Human herpesvirus type 8, Human herpesvirus type 8, Human immunodeficiency virus (HIV), Human metapneumovirus, Human papillomavirus, Imjin virus, Influenza virus, Isla Vista virus, JC virus, Junin virus, Khabarovsk virus, Koi herpes virus, Kunjin virus, Lassa virus, Limestone Canyon virus, Lloviu cuevavirus, Lloviu virus, Lujo virus, Machupo virus, Magboi virus, Marburg marburgvirus, Marburg virus, Marburgvirus, Measles virus, Melaka virus, Menangle virus, Middle East respiratory syndrome coronavirus, Miniopterus Bat coronavirus 1, Miniopterus Bat coronavirus HKU8, Monkeypox virus, Monongahela virus, Muju virus, Mumps virus, Nipah virus, Norwalk virus, Orbivirus, Parainfluenza virus, Parvovirus B19, Phytoreovirus, Pipistrellus bat coronavirus HKU5, Poliovirus, Porcine adenovirus, Prospect Hill virus, Qalyub virus, Rabies virus, Ravn virus, Respiratory syncytial virus, Reston virus, Reticuloendotheliosis virus, Rhinolophus Bat coronavirus HKU2, rhinovirus, Roseolovirus, Ross River virus, Rotavirus, Rousettus bat coronavirus HKU9, Rubella virus, Saaremaa virus, Sabia virus, Sangassou virus, Scotophilus Bat coronavirus 512, Serang virus, Severe acute respiratory syndrome virus, Shope papilloma virus, Simian foamy virus, Sin Nombre virus, Smallpox, Soochong virus, Sudan ebolavirus, Sudan virus, Tai Forest ebolavirus, Tai Forest virus, Tanganya virus, Thottapalayam virus, Topografov virus, Tremovirus, Tula virus, Turkey coronavirus, Turkeypox virus, Tylonycteris bat coronavirus HKU4, Varicella zoster virus, Varicella-zoster virus, West*

Nile virus, Woodchuck hepatitis virus, yellow fever virus, Zika virus, or Zaire ebolavirus.

Some non-limiting examples of a pathogen include a virus, bacterium, prion, fungus, parasite, protozoan, and microbe. Some non-limiting examples of pathogens include Acanthamoeba, Acari, Acinetobacter baumannii, Actinomyces israelii, Actinomyces gerencseriae, Propionibacterium propionicus, Actinomycetoma, Eumycetoma, Adenoviridae, Alphavirus, Anaplasma genus, Anaplasma phagocytophilum, Ancylostoma braziliense, Ancylostoma duodenale, Necator americanus, Angiostrongylus costaricensis, Anisakis, Arachnida Ixodidae, Argasidae, Arcanobacterium haemolyticum, Archiacanthocephala, Moniliformis moniliformis, Arenaviridae, Ascaris lumbricoides, Ascaris sp. Ascaris lumbricoides, Aspergillus genus, Astroviridae, Babesia B. divergens, B. bigemina, B. equi, B. microfti, B. duncani, Babesia genus, Bacillus anthracis, Bacillus cereus, Bacteroides genus, Balamuthia mandrillaris, Balantidium coli, Bartonella henselae, Baylisascaris genus, Baylisascaris procyonis, Bertiella mucronata, Bertiella studeri, BK virus, Blastocystis, Blastocystis hominis, Blastomyces dermatitidis, Bordetella pertussis, Borrelia burgdorferi, Borrelia species, Borrelia genus, Brucella genus, Brugia malayi, Brugia timori, Bunyaviridae, Burkholderia cepacia, Burkholderia species, Burkholderia mallei, Burkholderia pseudomallei, Caliciviridae, Campylobacter genus, Candida albicans, Candida species, Cestoda, Taenia multiceps, Chlamydia trachomatis, Chlamydia trachomatis, Neisseria gonorrhoeae, Chlamydophila pneumoniae, Chlamydophila psittaci, Cimicidae Cimex lectularius, Clonorchis sinensis; Clonorchis viverrini, Clostridium botulinum, Clostridium difficile, Clostridium perfringens, Clostridium perfringens, Clostridium species, Clostridium tetani, Coccidioides immitis, Coccidioides posadasii, Cochliomyia hominivorax, Colorado tick fever virus (CTFV), Coronaviridae, Corynebacterium diphtheriae, Coxiella burnetii, Crimean-Congo hemorrhagic fever virus, Cryptococcus neoformans, Cryptosporidium, Cryptosporidium genus, Cyclospora cayetanensis, Cytomegalovirus, Demodex folliculorum/brevis/canis, Dengue viruses (DEN-1, DEN-2, DEN-3 and DEN-4), Flaviviruses, Dermatobia hominis, Dicrocoelium dendriticum, Dientamoeba fragilis, Dioctophyme renale, Diphyllobothrium, Diphyllobothrium latum, Dracunculus medinensis, Ebolavirus (EBOV), Echinococcus genus, Echinococcus granulosus, Echinococcus multilocularis, E. vogeli, E. oligarthrus, Ehrlichia chaffeensis, Ehrlichia ewingii, Ehrlichia genus, Entamoeba histolytica, Entamoeba histolytica, Enterobius vermicularis, Enterobius gregorii, Enterococcus genus, Enterovirus genus, Enteroviruses, Coxsackie A virus, Enterovirus 71 (EV71), Epidermophyton floccosum, Trichophyton rubrum, Trichophyton mentagrophytes, Epstein-Barr Virus (EBV), Escherichia coli O157:H7, O111 and O104:H4, Fasciola hepatica, Fasciola gigantica, Fasciolopsis buski, Filarioidea superfamily, Filoviridae, Flaviviridae, Fonsecaea pedrosoi, Francisella tularensis, Fusobacterium genus, Geotrichum candidum, Giardia intestinalis, Giardia lamblia, Gnathostoma spinigerum, Gnathostoma hispidum, Group A Streptococcus, Staphylococcus, Guanarito virus, Haemophilus ducreyi, Haemophilus influenzae, Halicephalobus gingivalis, Heartland virus, Helicobacter pylori, Hepadnaviridae, Hepatitis A Virus, Hepatitis B Virus, Hepatitis C Virus, Hepatitis D Virus, Hepatitis E Virus, Hepeviridae, Herpes simplex virus 1 and 2 (HSV-1 and HSV-2), Herpesviridae, Histoplasma capsulatum, HIV (Human immunodeficiency virus), Hortaea werneckii, Human bocavirus (HBoV), Human herpesvirus 6 (HHV-6), Human herpesvirus 7 (HHV-7), Human metapneumovirus (hMPV), Human papillomavirus (HPV), Human parainfluenza viruses (HPIV), Hymenolepis nana, Hymenolepis diminuta, Isospora belli, JC virus, Junin virus, Kingella kingae, Klebsiella granulomatis, Lassa virus, Legionella pneumophila, Leishmania, Leptospira genus, Linguatula serrata, Listeria monocytogenes, Loa loa filaria, Lymphocytic choriomeningitis virus (LCMV), Machupo virus, Malassezia genus, Mansonella streptocerca, Marburg virus, Measles virus, Metagonimus yokagawai, Microsporidia phylum, Middle East respiratory syndrome coronavirus, Molluscum contagiosum virus (MCV), Monkeypox virus, Mucorales order (Mucormycosis), Entomophthorales order (Entomophthoramycosis), Mumps virus, Mycobacterium leprae, Mycobacterium lepromatosis, Mycobacterium tuberculosis, Mycobacterium ulcerans, Mycoplasma pneumoniae, Naegleria fowleri, Neisseria gonorrhoeae, Neisseria meningitidis, Nocardia asteroides, Nocardia species, Oestroidea, Calliphoridae, Sarcophagidae, Onchocerca volvulus, Opisthorchis viverrini, Opisthorchis felineus, Clonorchis sinensis, Orthomyxoviridae, Papillomaviridae, Paracoccidioides brasiliensis, Paragonimus africanus; Paragonimus caliensis; Paragonimus kellicotti; Paragonimus skrjabini; Paragonimus uterobilateralis, Paragonimus westermani, Paragonimus species, Paramyxoviridae, parasitic dipterous fly larvae, Parvoviridae, Parvovirus B19, Pasteurella genus, Pediculus humanus, Pediculus humanus capitis, Pediculus humanus corporis, Phthirus pubis, Picornaviridae, Piedraia hortae, Plasmodium falciparum, Plasmodium vivax, Plasmodium ovale curtisi, Plasmodium ovale wallikeri, Plasmodium malariae, Plasmodium knowlesi, Plasmodium genus, Pneumocystis jirovecii, Poliovirus, Polyomaviridae, Poxviridae, Prevotella genus, PRNP, Pthirus pubis, Pulex irritans, Rabies virus, Reoviridae, Respiratory syncytial virus (RSV), Retroviridae, Rhabdoviridae, Rhinosporidium seeberi, Rhinovirus, rhinoviruses, coronaviruses, Rickettsia akari, Rickettsia genus, Rickettsia prowazekii, Rickettsia rickettsii, Rickettsia typhi, Rift Valley fever virus, Rotavirus, Rubella virus, Sabia, Salmonella enterica subsp. enterica, serovar typhi, Salmonella genus, Sarcocystis bovihominis, Sarcocystis suihominis, Sarcoptes scabiei, SARS coronavirus, Schistosoma genus, Schistosoma haematobium, Schistosoma japonicum, Schistosoma mansoni and Schistosoma intercalatum, Schistosoma mekongi, Schistosoma sp., Shigella genus, Sin Nombre virus, Spirometra erinaceieuropaei, Sporothrix schenckii, Staphylococcus genus, Streptococcus agalactiae, Streptococcus pneumoniae, Streptococcus pyogenes, Strongyloides stercoralis, Taenia genus, Taenia saginata, Taenia solium, the bacterial family Enterobacteriaceae, Thelazia californiensis, Thelazia callipaeda, Togaviridae, Toxocara canis, Toxocara cati, Toxoplasma gondii, Treponema pallidum, Trichinella spiralis, Trichinella britovi, Trichinella nelsoni, Trichinella nativa, Trichobilharzia regenti, Schistosomatidae, Trichomonas vaginalis, Trichophyton genus, Trichophyton rubrum, Trichophyton tonsurans, Trichosporon beigelii, Trichuris trichiura, Trichuris trichiura, Trichuris vulpis, Trypanosoma brucei, Trypanosoma cruzi, Tunga penetrans, Ureaplasma urealyticum, Varicella zoster virus (VZV), Variola major, Variola minor, Venezuelan equine encephalitis virus, Vibrio cholerae, West Nile virus, Wuchereria bancrofti, Wuchereria bancrofti, Brugia malayi, Yellow fever virus, Yersinia enterocolitica, Yersinia pestis, and Yersinia pseudotuberculosis.

Methods of Generating a Collection of Oligonucleotides

This disclosure provides multiple avenues for generating a collection of oligonucleotides for use in the methods provided herein, particularly for targeting or detecting a population of interest (e.g., microbial or pathogen nucleic acids). In some cases, a method of generating a collection of oligonucleotides may be a bioinformatic, computational, hybridization-based, or digestion-based method.

In some cases, a background population nucleic acid such as host (e.g., human) genomic DNA may be used to remove host sequences from a population of oligonucleotides that contains host and non-host (e.g., non-human, pathogen) sequences. The method may involve providing a heterogeneous collection of oligonucleotides (e.g., a collection of oligonucleotide randomers such as e.g., 5'-NNNNNNNNNNNNN-3', where N is A, C, G, or T) containing oligonucleotides capable of binding host (e.g., human) and non-host nucleic acids. In some instances, the host genomic DNA may be introduced to the heterogeneous collection of oligonucleotides under conditions promoting binding of the host genomic DNA with complementary sequences in the heterogeneous collection of oligonucleotides. The method may comprise depleting the oligonucleotides bound to the host genomic DNA from the heterogeneous collection of oligonucleotides. Often, in such methods, the host nucleic acids (e.g., host genomic nucleic acids) are provided in excess quantities relative to the heterogeneous collection of oligonucleotides. The depletion may be completed by methods provided herein such as by removing the hybridized or bound oligonucleotides from the heterogeneous collection of oligonucleotides, destroying the hybridized or bound oligonucleotides, or preferentially isolating unbound oligonucleotides.

Figure 3:
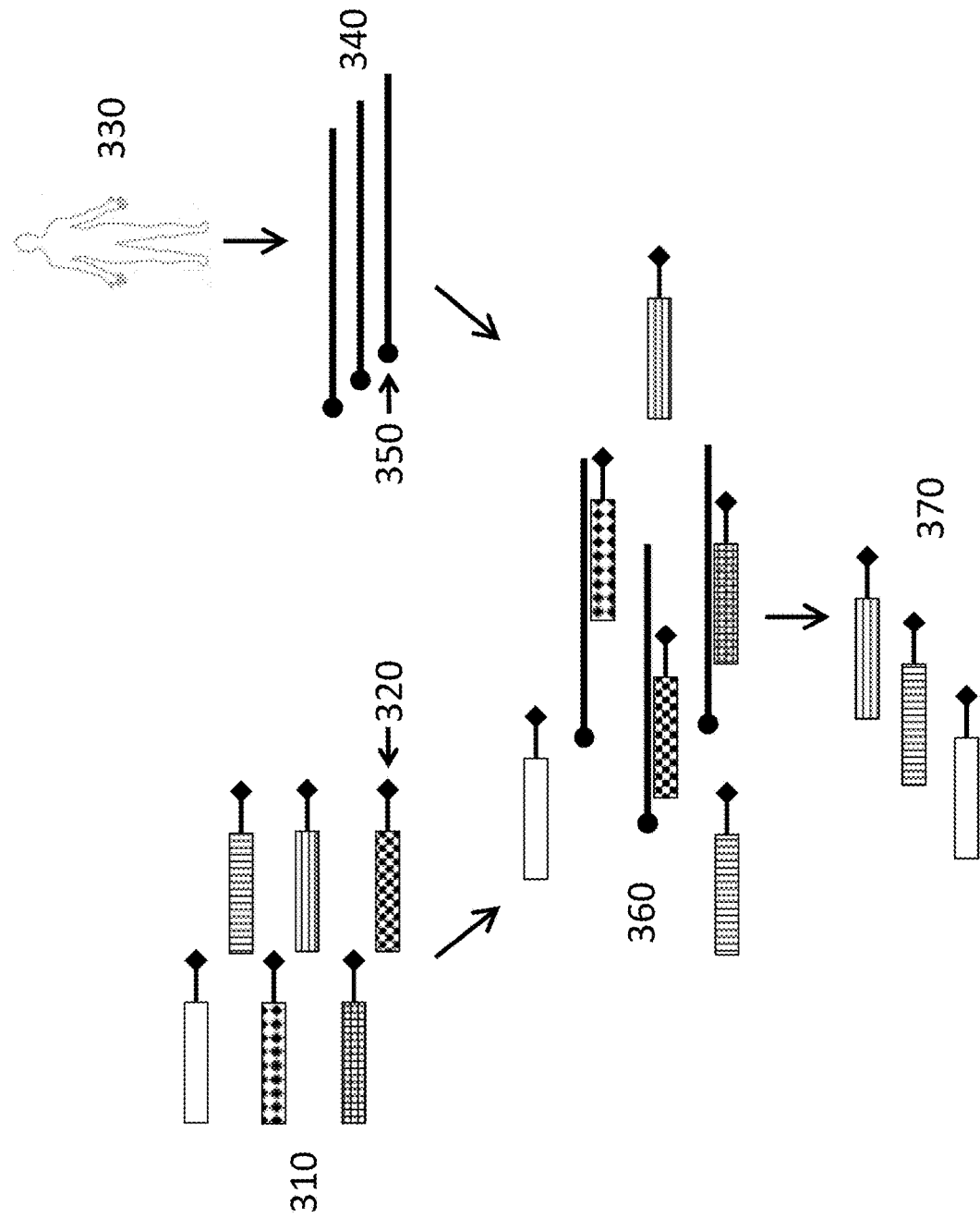
FIG. 3 shows a method of generating a collection of oligonucleotides using a hybridization-based method.

FIG. 3 shows a pictorial example of generating a collection of oligonucleotides (370). The method may comprise providing a heterogeneous collection of oligonucleotides (310). In some cases, the heterogeneous collection of oligonucleotides may comprise oligonucleotides labeled with a nucleic acid label, a chemical label, or an optical label (320). The method may comprise depleting oligonucleotides comprising a domain of nucleotides with sequences identical to, nearly identical to, complementary to, or nearly complementary to background population nucleic acids (e.g., host nucleic acids, human nucleic acids, etc.) from the heterogeneous collection of oligonucleotides. In some cases, the depleting is accomplished by contacting (360) the heterogeneous collection of oligonucleotides with background population nucleic acids (340) (e.g., human genomic DNA) such that the background population nucleic acids hybridize, or otherwise specifically bind to, complementary or nearly complementary domains of nucleotides of oligonucleotides within the heterogeneous collection of oligonucleotides. The hybridization reaction may include a denaturation step and/or a renaturation step. For example, in order to denature the nucleic acids in the reaction, the nucleic acids may be heated or subjected to tiered heating (e.g., 95° C. for 10 seconds and at 65° C. for 3 min). In order to renature the nucleic acids, the nucleic acids may be incubated at 36° C. for a certain amount of time, such as hours or weeks. In some cases, the background population nucleic acids are derived or isolated from a host (330). In some cases, the background population nucleic acids are labeled with a nucleic acid label, a chemical label, or an optical label (350). In some cases, the method further comprises denaturing at least a portion of the background population nucleic acids, e.g., by heat.

In some cases, one or more blocker oligonucleotides may be present during the hybridization step (360), and may be included before or during the hybridization step. In some instances, a blocker oligonucleotide comprises DNA, RNA, PNA, LNA, BNA, or any combination thereof. A blocker oligonucleotide may be complementary to sequences of oligonucleotides outside of the domain of nucleotides and, as such, may be designed to not hybridize to the domain of nucleotides, but rather to "block" other nucleotides present on the same strand. The presence of the blocker oligonucleotides may help reduce the possibility that sequences outside of the domain of nucleotides bind to the background population of oligonucleotides (e.g., human genomic DNA). As such, the blocker oligonucleotides may promote binding specificity of the collection of oligonucleotides to the background population of oligonucleotides. In some specific examples, the heterogeneous collection of oligonucleotides may hybridize to genomic DNA in a buffered solution comprising blocker oligonucleotide (e.g., 0.5×PBS, blocker oligonucleotide, RNase inhibitor).

Often, the heterogeneous collection of oligonucleotides that is used as the starting population to produce the collection of oligonucleotides provided herein are collections of randomly generated nucleic acid sequences (e.g., a collection of oligonucleotide randomers such as e.g., 5'-NNNNNNNNNNNNN-3', where N is A, C, G, or T). In some cases, a heterogeneous collection of oligonucleotides may be synthesized (e.g., by DNA synthesis). In some cases, a heterogeneous collection of oligonucleotides does not comprise artificially fragmented nucleic acids. In some cases, a heterogeneous collection of oligonucleotides comprises oligonucleotides comprising a domain of nucleotides, wherein about 5, 10, 20, 30, 40, 50, 60, 70, 80, 90, 91, 92, 93, 94, 95, 96, 97, 98, 99, 99.1, 99.2, 99.3, 99.4, 99.5, 99.6, 99.7, 99.8, 99.9, or 100% of possible sequences for a domain of nucleotides are present. In some cases, a heterogeneous collection of oligonucleotides comprises oligonucleotides comprising a domain of nucleotides, wherein up to 5, 10, 20, 30, 40, 50, 60, 70, 80, 90, 91, 92, 93, 94, 95, 96, 97, 98, 99, 99.1, 99.2, 99.3, 99.4, 99.5, 99.6, 99.7, 99.8, 99.9, or 100% of possible sequences for a domain of nucleotides are present. In some cases, a heterogeneous collection of oligonucleotides comprises oligonucleotides comprising a domain of nucleotides, wherein at least 5, 10, 20, 30, 40, 50, 60, 70, 80, 90, 91, 92, 93, 94, 95, 96, 97, 98, 99, 99.1, 99.2, 99.3, 99.4, 99.5, 99.6, 99.7, 99.8, 99.9, or 100% of possible sequences for a domain of nucleotides are present.

In some cases, the heterogeneous collection of oligonucleotides comprises oligonucleotides comprising a domain of nucleotides with sequences identical to, nearly identical to, complementary to, or nearly complementary to background population nucleic acids or nucleic acids from a population of interest. In some cases, the heterogeneous collection of oligonucleotides comprises oligonucleotides comprising a domain of nucleotides with sequences that are identical to, nearly identical to, complementary to, or nearly complementary to one or more background populations. In some cases, the heterogeneous collection of oligonucleotides comprises oligonucleotides comprising a domain of nucleotides with sequences that are not identical to, nearly identical to, complementary to, or nearly complementary to one or more background populations. In some cases, the heterogeneous collection of oligonucleotides comprises oligonucleotides comprising a domain of nucleotides with sequences that are identical to, nearly identical to, complementary to, or nearly complementary to one or more populations of interest. In some cases, the heterogeneous collection of oligonucleotides comprises oligonucleotides comprising a domain of nucleotides with sequences that are not identical to, nearly identical to, complementary to, or nearly complementary to one or more populations of interest.

In some cases, one or more oligonucleotides within the heterogeneous collection of oligonucleotides are unlabeled; in some cases, one or more oligonucleotides within the heterogeneous collection of oligonucleotides are labeled. In some cases, one or more oligonucleotides are labeled, e.g., with a nucleic acid label, a chemical label, or an optical label. In some cases, one or more oligonucleotides are conjugated to a solid support. In some cases, one or more oligonucleotides are not conjugated to a solid support. In some cases, a label may be attached at the 5' or 3' end of an oligonucleotide or internally within an oligonucleotide. In some cases, one or more oligonucleotides within the heterogeneous collection of oligonucleotides are labeled with more than one label.

The background population nucleic acids may be provided in excess quantities relative to the heterogeneous collection of oligonucleotides. The ratio of background population to oligonucleotides may be about 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population to oligonucleotides may be up to 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population to oligonucleotides may be at least 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population to oligonucleotides may be saturating. The ratio of background population to oligonucleotides may be non-saturating. The ratio may be calculated in terms of concentration, moles, or mass.

In some cases, the nucleic acids are single-stranded. In some cases, double-stranded nucleic acids are denatured into single-stranded nucleic acids. Nucleic acids may be denatured using heat. In some cases, nucleic acids are heated to about 35, 40, 45, 50, 55, 60, 65, 70, 75, 80, 85, 90, 91, 92, 93, 94, 95, 96, 97, 98, or 99° C. In some cases, nucleic acids are heated for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes. In some cases, nucleic acids are denatured using a chemical denaturant (e.g., acid, base, solvent, chaotropic agent, salt).

A sample of single-stranded nucleic acids may be renatured or hybridized. In some cases, a sample of single-stranded nucleic acids is hybridized with a heterogeneous collection of oligonucleotides. In some cases, a heterogeneous collection of oligonucleotides is hybridized with blocker oligonucleotides. In some cases, at least a portion of the single-stranded nucleic acids is renatured or hybridized. In some cases, nucleic acids are renatured or hybridized at about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 40, 45, 50, 55, 60, 65, 68, or 70° C. In some cases, nucleic acids are renatured or hybridized on ice. In some cases, nucleic acids are renatured or hybridized at room temperature. In some cases, nucleic acids are renatured or hybridized for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes or 2, 3, 4, 5, 10, 15, 20, 22, 24, 30, 40, 46, 48, 50, 60, 70, 72, 80, or 96 hours. Temperature, buffer composition, reaction time, and concentration can affect the extent of hybridization. In some cases, nucleic acids are renatured in the presence of trimethylammonium chloride.

The depletion may be completed by methods provided herein such as by removing the hybridized nucleic acids from the heterogeneous collection of oligonucleotides. The background population may be chemically labeled and removed, thereby removing hybridized oligonucleotides. The background population may be conjugated to magnetic beads and removed with a magnet, thereby removing hybridized oligonucleotides. The background population may be labeled with a nucleic acid tag. The nucleic acid tag may bind to or hybridize to a nucleic acid sequence that is conjugated to a solid support or tagged with a chemical tag. Hybridized oligonucleotides may be removed by size separation (e.g., gel electrophoresis, capillary electrophoresis, etc.), affinity separation (e.g., a DNA pull-down assay, chromatography, etc.), or other methods. In some cases, the hybridized oligonucleotides may be isolated based on differences in size of non-hybridized oligonucleotides and hybridized oligonucleotides using a separation method such as gel electrophoresis, capillary electrophoresis, or chromatography. In some cases, non-hybridized background population nucleic acids are not removed.

In some cases, the depletion may be completed by inactivating the oligonucleotides that are hybridized to background population nucleic acids. Inactivation may prevent oligonucleotides that hybridize to background population nucleic acids from acting as a primer, e.g., by chemically binding the oligonucleotides to labeled background population nucleic acids and then amplifying only using unbound oligonucleotides.

In some cases, the collection of oligonucleotides is designed to target a population of interest (e.g., pathogen nucleic acids, non-human nucleic acids) using bioinformatic or computational tools and then synthesized according to the design. In some cases, the method of synthesis is DNA synthesis. The method may involve obtaining a database of randomly-generated oligonucleotides of a certain length. The method may comprise bioinformatically or computationally determining domains of nucleotides present in one or more background populations (e.g., human genomic nucleic acids). Sequences associated with such domains of nucleotides may then be computationally subtracted from the randomly-generated heterogeneous collection of oligonucleotides, such that the resulting collection of oligonucleotides has little or no background population sequences of a particular length (e.g., 10, 11, 12, 13, 14, or 15 nucleotides, etc.).

Synthesis of Collections of Non-Host Oligonucleotides

Following identification of non-host oligonucleotide sequences, synthesis of collections of non-host oligonucleotides can be accomplished via a myriad of approaches. For example, non-host oligonucleotides may be synthesized on an individual basis by the step-wise addition of nucleotides to produce an oligonucleotide of a desired length (e.g., 13-mer).

Figure 10A:
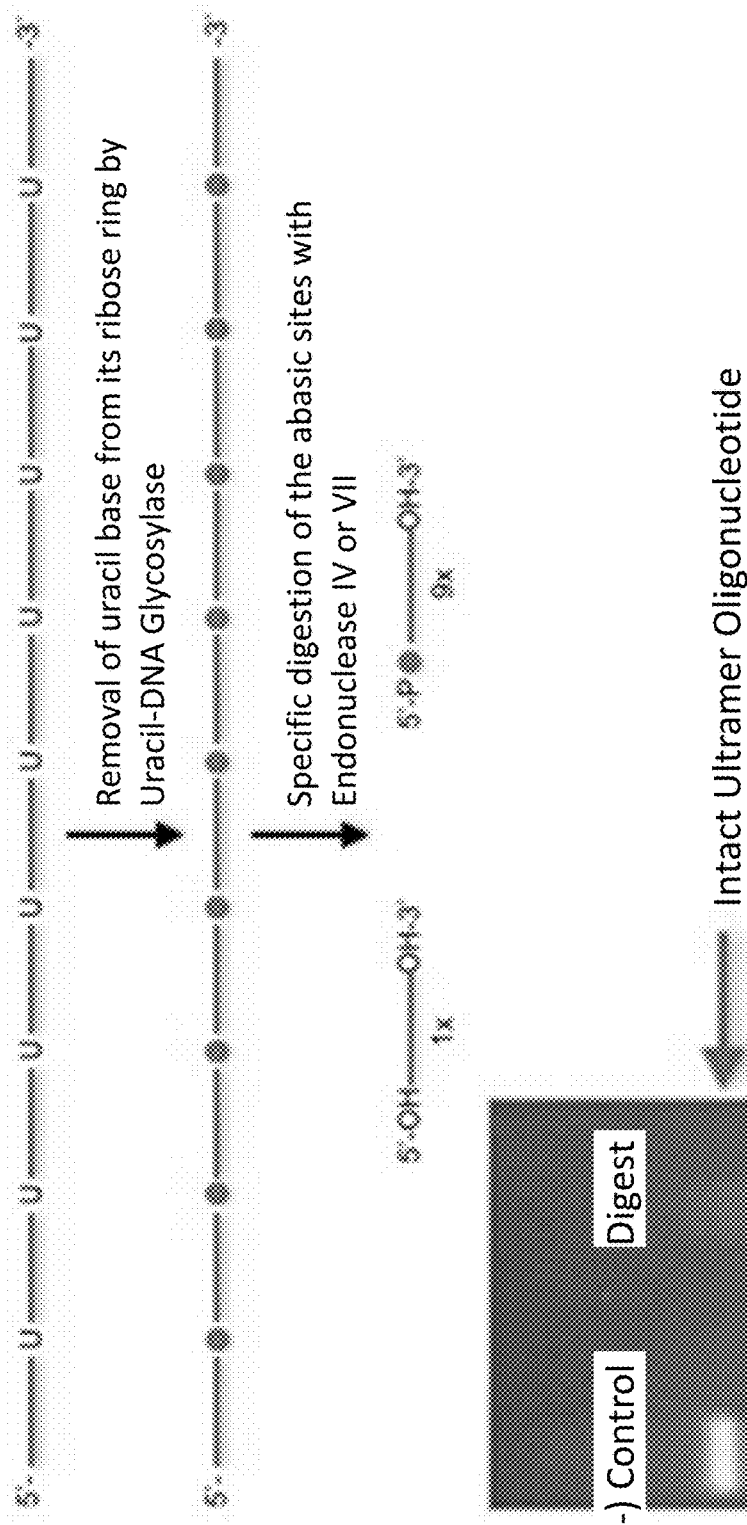
FIG. 10A illustrates a reaction scheme for generating a collection of oligonucleotides from an ultramer oligonucleotide.
Figure 10B:
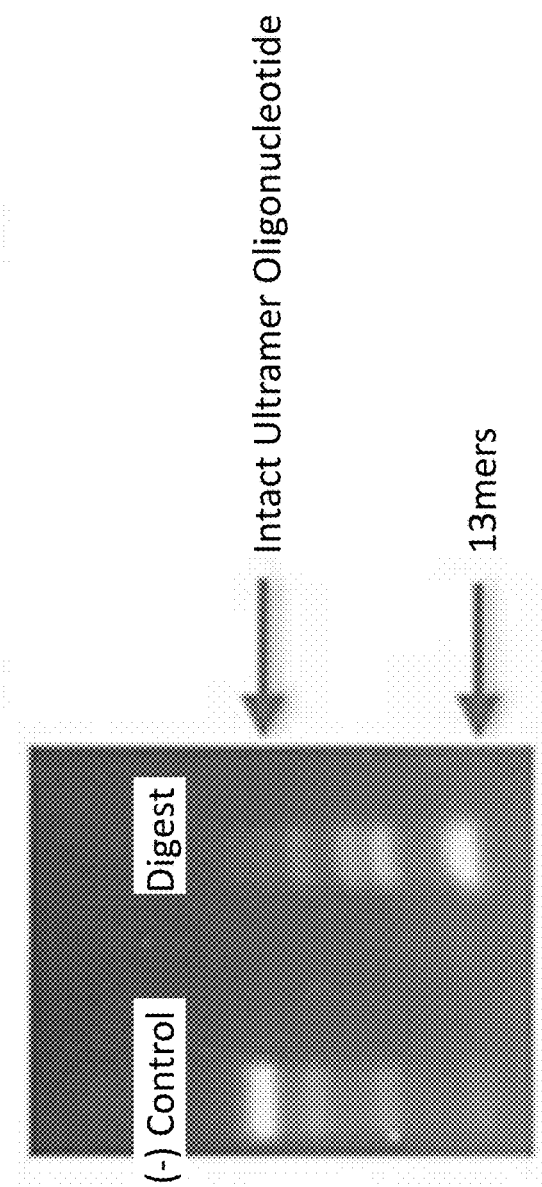
FIG. 10B shows an example of the digestion reaction products after digestion of an ultramer oligonucleotide.

In some instances, ultramer oligonucleotides are used to synthesize a collection of oligonucleotides provided herein. In general, an ultramer oligonucleotide is a long oligonucleotide containing numerous oligonucleotide sequence units strung together, each of which is separated by one or more spacer nucleotides. The spacer nucleotides can be cut or otherwise separated in order to produce a set of oligonucleotides from a single ultramer oligonucleotide. FIG. 9A shows a general design of a representative ultramer oligonucleotide. Here, individual oligonucleotide sequences are separated by a deoxyuracil nucleotide (U), which serves as a spacer nucleotide. The ultramer oligonucleotides may be digested by the double action of Uracil-DNA Glycosylase (UDG) (which excises uracil residues from DNA by cleaving N-glycosidic bonds) and an endonuclease with specificity for abasic sites (e.g., apurinic/apyrimidinic site or AP site), thereby producing individual oligonucleotides (e.g., 13-mer oligonucleotides). In some cases, the ultramer oligonucleotide is hydrolyzed using endonuclease IV or endonuclease VII. An exemplary reaction is described in FIG. 10A. FIG. 10B shows an example of the digestion reaction products after digestion of an ultramer oligonucleotide with UDG and Endonuclease VII.

Ultramer oligonucleotides can be designed such that individual oligonucleotide units within the same ultramer strand share the same degree of degeneracy. Degeneracy generally refers to the number of different unique sequences that can be produced from a single variable sequence. This can be accomplished by inserting one or more mixed bases at certain positions within the oligonucleotide units. A mixed base may refer to any one of a set of bases (e.g., any one of the four canonical bases: A, C, G, or T bases). For example, in standard coding schemes, an "N" mixed base may be any one of A, C, G, or T bases. Similarly, a "D" mixed base may be A, G, or T; a "V" mixed base may be A, C, or G; a "B" mixed base may be C, G, or T; an "H" mixed base may be A, C, or T; a "W" mixed base may be A or T; an "S" mixed base may be C or G; a "K" mixed base may be C or G; an "M" mixed base may be A or C; a "Y" mixed base may be C or T; and a "R" mixed base may be A or G. Under such a coding scheme, an oligonucleotide sequence containing one N mixed base would have a degree of degeneracy of 4, since four possible sequences can be generated, as shown in FIG. 9B and FIG. 11A. Likewise, an oligonucleotide sequence containing two N mixed bases would have a degree of degeneracy of 4×4=16, since 16 possible sequences can be generated, as shown in FIG. 9C and FIG. 11A. An oligonucleotide sequence containing one N mixed base and one W, S, K, M, Y, or R mixed base would have a degree of degeneracy of 4×2=8, since 8 possible sequences can be generated, as shown in FIG. 9D. An oligonucleotide sequence containing one R mixed base and one D mixed base would have a degree of degeneracy of 2×3=6, since 6 possible sequences can be generated.

When oligonucleotide sequences within an ultramer share the same degree of degeneracy, each oligonucleotide sequence within the ultramer will likely be represented in equal number following digestion of the ultramer. For example, when oligonucleotide sequences within an ultramer each possess a degree of degeneracy of 4, then each of the four different unique oligonucleotides per oligonucleotide sequence unit will be present in approximately equal amounts in the resulting synthesized pool. However, if for example, an ultramer contains one oligonucleotide unit with 2 degrees of degeneracy and 9 oligonucleotide units with 4 degrees of degeneracy, then the two oligonucleotides from the one 2-degree unit will be over-represented at ~5% each in the resulting synthesized and digested pool relative to the 36 oligonucleotides from the nine 4-degree units at ~2.5% each. Therefore, ultramers with oligonucleotide units with shared degrees of degeneracy may yield collections of oligonucleotides with evenly-distributed unique sequences.

Non-host oligonucleotide sequences can be identified computationally and grouped by degree of degeneracy. The degeneracy of sequences can be identified by computationally sorting sequences together that differ only by a certain number of positions, for example, all sequences that are identical except at positions 1 and 2. The number and type of mixed bases required to group multiple degenerate sequences into a single variable sequence with one or more mixed bases can determine the degree of degeneracy. FIG. 11 shows a computational grouping of non-host oligonucleotides by degrees of degeneracy. FIG. 11A shows representative oligonucleotides with 1, 2, or 3 "N" mixed-base sites. The histogram in FIG. 11B shows bucketing of non-human 13-mers based on the degree of degeneracy. The first column in FIG. 11B shows the number of non-human 13-mers with a degree of degeneracy of "2," meaning that they contain a single mixed base signifying two possible bases (e.g., a W mixed base, a S mixed base, a K mixed base, a M mixed base, a Y mixed base, or a R mixed base). The second column shows the number of non-human 13-mers with 3 degrees of degeneracy (e.g., a D, V, B or H mixed base). The remaining columns indicate the number of non-human 13-mers with 4, 6, 8, 9, 12, or 16 degrees of degeneracy. For example, non-human 13-mers with a degree of degeneracy of 4 could include one N mixed base or any two mixed bases selected from W, S, K, M, Y, and R.

Representatives of each degenerate group of non-host (e.g., non-human) oligonucleotides (e.g., 13-mers) can be combined with other representatives of the same degree of degeneracy into an ultramer oligonucleotide, as shown in FIG. 9, discussed elsewhere herein. The designed ultramer oligonucleotide may then be synthesized by conventional nucleic acid synthesis processes and service providers, e.g., IDT.

Digestion of ultramers containing oligonucleotide units (or sequences) with a shared degree of degeneracy can be carried out in any of a number of different steps. In some cases, groups of ultramers, all containing units with a shared degree of degeneracy, are combined and then digested. For example, multiple ultramer oligonucleotides, all carrying oligonucleotide sequences with the same degree of degeneracy, can be combined in equimolar concentrations and digested in order to maintain equimolar concentrations of the resulting oligonucleotides. In another approach, ultramers may be first individually digested and then the resulting oligonucleotide units may be combined in equimolar concentrations following such digestion.

Digestion of ultramers containing oligonucleotide units (or sequences) with different degrees of degeneracy can be carried out in any of a number of different steps. In some cases, groups of ultramers, each containing units with a different degree of degeneracy, are combined and then digested. For example, multiple ultramer oligonucleotides, each carrying oligonucleotide sequences with a different degree of degeneracy, can be combined in appropriate ratios and digested in order to produce equimolar concentrations of the resulting oligonucleotides. In another approach, ultramers may be first individually digested and then the resulting oligonucleotide units may be combined in appropriate ratios following such digestion to produce equimolar concentrations of the resulting oligonucleotides.

An ultramer oligonucleotide provided herein may comprise any number of oligonucleotide units (or sequences). For example, an ultramer oligonucleotide may comprise 5, 6, 7, 8, 9, 10, 15, 20, 25, 50, 100, or 200 or more oligonucleotide units or sequences. In some cases, the oligonucleotide units or sequences contain a domain of nucleotides with a certain length, such as a length between 5 and 100 nucleotides (e.g., 5, 10, 11, 12, 13, 14, 15, 16, 17, 18, 19, 20, or more nucleotides). Preferably, the domain of nucleotides is a 13-mer. In some embodiments, each domain of nucleotides comprises 1 or more, 2 or more, 3 or more, 4 or more, 5 or more, 6 or more, 7 or more, 8 or more, 9 or more, 10 or more, 11 or more, 12 or more, or 13 or more mixed bases. In some embodiments, the mixed base is selected from the group consisting of N (A, C, G, T), D (A, G, T), V (A, C, G), B (C, G, T), H (A, C, T), W (A, T), S (C, G), K (G, T), M (A, C), Y (C, T), R (A, G), and any combination thereof. In some embodiments, the oligonucleotide sequences have a same degree of degeneracy. In some embodiments, the oligonucleotide sequences have a degree of degeneracy of 2, 3, 4, 6, 8, 9, 12, 16, 18, 24, 27, 32, 36, 48, 54, 64, 72, 81, 96, 108, 128, 144, 162, 192, 216, 243, or 256.

Figures 12A, 12B:
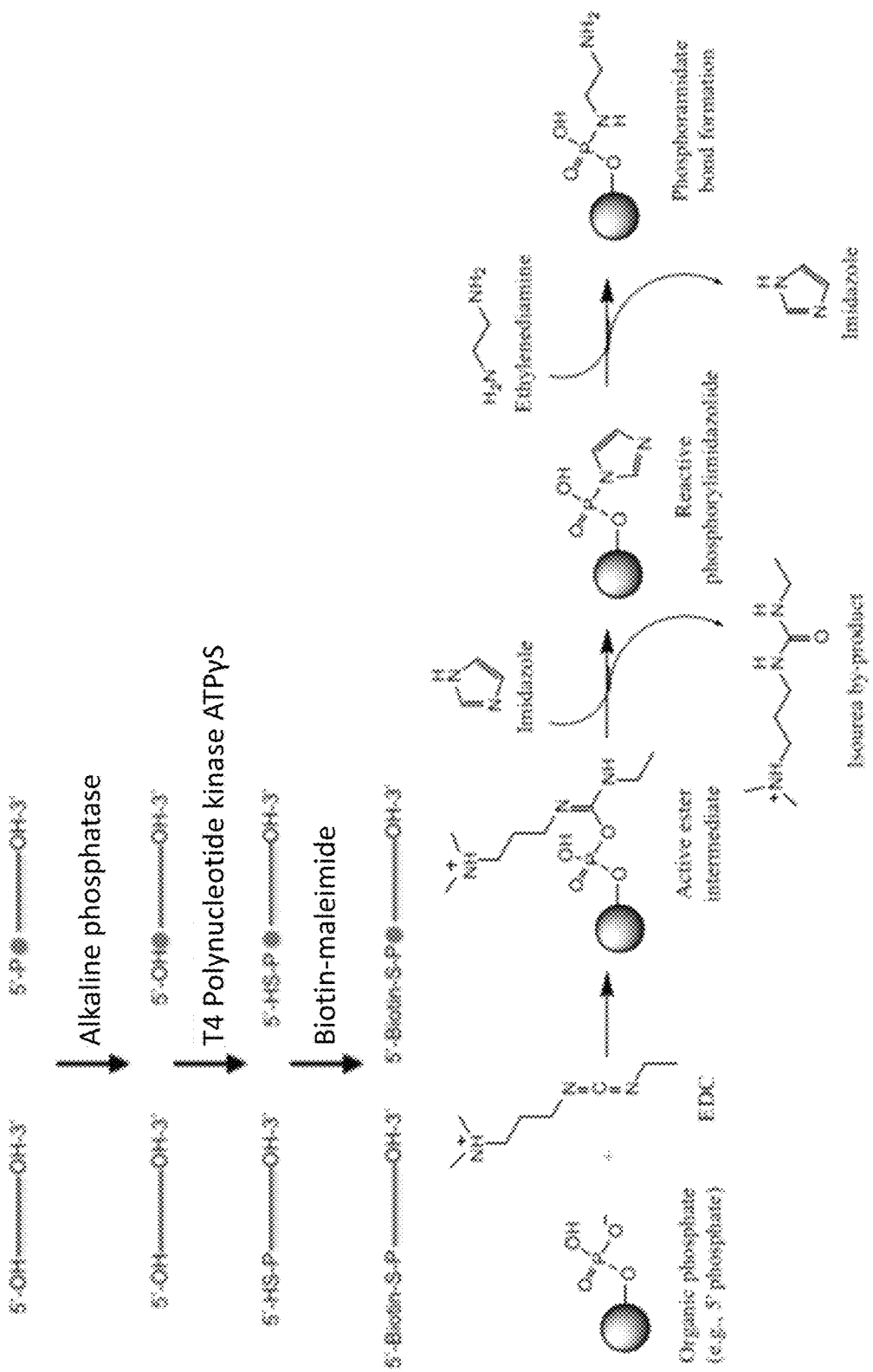
FIG. 12A provides a schematic illustration of a process for enzymatic biotinylation of oligonucleotides.
FIG. 12B provides a schematic illustration of a process for chemical biotinylation of oligonucleotides.

Individual oligonucleotides may be biotinylated, e.g., using T4 Polynucleotide Kinase (T4 PNK) or chemically as shown in FIG. 12. This step may be particularly useful if surface immobilization or magnetic bead purification is required. For example, the biotinylated oligonucleotides may be combined with a sample and allowed to hybridize to non-host oligonucleotides within the sample. Streptavidin-coated beads may be added to the sample and used to pull-down, or otherwise isolate, the non-host oligonucleotides.

The ultramer approaches to producing oligonucleotides provided herein have several advantages. In some cases, such methods can reduce the number of synthesis runs needed to produce a highly-diverse collection of oligonucleotides (e.g., collection of highly-diverse 13-mer oligonucleotides). Such methods may also reduce synthesis costs, reduce synthesis of excess amounts of oligonucleotides, minimize manual steps of mixing oligonucleotides together, or enable synthesis of oligonucleotides in high yields.

Using a Collection of Oligonucleotides

In some cases, a collection of oligonucleotides may be used as primers or capturing agents for PCR amplification, cDNA synthesis, sequencing, or primer extension reactions, as shown in FIG. 1 and FIG. 2. In some cases, the collection of oligonucleotides (150) is mixed with a sample of nucleic acids (140). In some cases, the sample of nucleic acids is derived from a biological sample, e.g., a blood sample (120) or plasma (130), from a host (110). In many cases, where the collection of oligonucleotides is used to prime amplification, cDNA synthesis, sequencing or primer extension, the oligonucleotides and sample nucleic acids may be combined with appropriate polymerization enzymes, such as DNA polymerases, reverse transcriptases, RNA polymerases, and the like. In some cases, where a nucleic acid sample comprises RNA, a collection of oligonucleotides may be used to prime cDNA synthesis from an RNA template (150). In some cases, where a nucleic acid sample comprises DNA, a collection of oligonucleotides may be used in a primer extension reaction (170). The primer extension reaction may append overhang sequences to the population of interest nucleic acids, e.g., adding a nucleic acid label, nucleic acid tag, barcode (e.g., sample barcode), universal primer sequence, primer binding site (e.g., for sequencing or to read a barcode, including, but not limited to, DNA sequencing primer binding site, sample barcode sequencing primer binding site, and amplification primer binding site compatible with various sequencing platform requirements), sequencer-compatible sequence, sequence to attach to a sequencing platform, sequencing adapter sequence, or adapter. In some cases, the primer extension reaction may add sequencing adapters only to population of interest (e.g., non-mammalian, non-human, microbial, or pathogen) nucleic acids. In some cases, a collection of oligonucleotides may be used as primers for a PCR reaction to amplify population of interest nucleic acids. In some cases, a labeled collection of oligonucleotides may be used to label a population of interest. Labeled population of interest nucleic acids may then be isolated, e.g., by hybridization-based or pull-down methods.

The pool of non-host oligonucleotides of any particular length may be different when seeking to enrich for non-host sequences in libraries prepared from DNA or RNA. For example, a greater fraction of all possible N-mers may remain after removing the N-mers with perfect complimentarily to the host genome relative to when removing N-mers with perfect complimentarily to the host exome. A greater fraction of the non-host exome can be probed relative to the non-host genome, potentially providing greater sensitivity in some cases. In addition, when seeking to utilize the same number oligonucleotides to probe the non-host genome and exome, the greater number of oligonucleotides that are not complimentary to the host exome may provide additional versatility in selecting which non-complimentary oligonucleotides are included in the pool, enabling selection of oligonucleotides with desirable sequence characteristics.

In some cases, a collection of oligonucleotides may be used for nucleic acid pull-down, as shown in FIG. 2. For instance, a collection of oligonucleotides (250) may be used as bait to capture a population of interest from a sample of nucleic acids (240). In some cases, a collection of oligonucleotides is labeled or conjugated to a solid support. Oligonucleotides in the collection of oligonucleotides may hybridize or otherwise specifically bind to, complementary or nearly complementary population of interest nucleic acids within the sample (260). In some cases, a labeled collection of oligonucleotides functions as primers for PCR amplification. In some cases, the PCR amplification products are pulled down. In some cases, the labels on the oligonucleotides of the collection of oligonucleotides are used to isolate the collection of oligonucleotides and hybridized or bound population of interest nucleic acids (e.g., by biotin-avidin, biotin-streptavidin, or nucleic acid hybridization interactions). In some cases, the sample of nucleic acids comprises circulating nucleic acids such as circulating cell-free nucleic acids. In some cases, the sample of nucleic acids comprises amplified, purified, or isolated nucleic acids, such as a sequencing-ready library of nucleic acids.

In some cases, a collection of oligonucleotides may be used for nucleic acid pull-down as a method for enriching non-host (e.g., pathogen) sequences after library preparation. In some cases, a labeled collection of oligonucleotides (e.g., a collection of oligonucleotides chemically labeled with biotin) may be hybridized to a single-stranded DNA or cDNA library. In some cases, a polymerase may be used to extend the hybridized oligonucleotides along library fragments, for example, under high fidelity conditions. The extended hybridized oligonucleotides may be pulled out using a binding partner of the label, such as streptavidin for a biotin label. In some cases, the enriched library may be amplified, for example, by PCR. Advantages of such a method include being an open ended enrichment method, in which host nucleic acids are selected against. In some cases, the enrichment method can be used for DNA or cDNA libraries. In some cases, positive selection of non-host library fragments results in improved kinetics and thermodynamics. In some cases, applying the method after standard library preparation allows batch processing of multiple samples that may be individually barcoded.

In some cases, population of interest (e.g., non-host) sequences in a sample of nucleic acids such as circulating nucleic acids may be primed or captured by: (a) providing a sample of nucleic acids, where the sample of nucleic acids comprises background population (e.g., host) nucleic acids and population of interest nucleic acids; (b) mixing the sample of nucleic acids with a collection of oligonucleotides, thereby obtaining a mixture, where the collection of oligonucleotides contains oligonucleotides with a domain of nucleotides; and (c) within the mixture, contacting the collection of oligonucleotides to the sample of nucleic acids, where the contacting causes population of interest nucleic acids within the mixture to bind the domains of nucleotides, thereby priming or capturing the population of interest nucleic acids.

Primed or captured nucleic acids may be further analyzed or processed. In some cases, primed or captured nucleic acids may be preferentially amplified in a reaction (e.g., a PCR reaction). In some cases, primed or captured nucleic acids may be sequenced by conducting a sequencing assay (e.g., a Next Generation sequencing assay, a high-throughput sequencing assay, a massively parallel sequencing assay, a Nanopore sequencing assay, or a Sanger sequencing assay). In some cases, primed or captured nucleic acids are preferentially isolated (e.g., by performing a pull-down assay). In some cases, a primer extension reaction is performed on the primed or captured nucleic acids (e.g., to attach a nucleic acid label to the primed or captured nucleic acids). In some cases, the primed or captured nucleic acids are RNA, and a polymerization reaction is performed on the primed or captured RNA nucleic acids (e.g., by reverse transcriptase).

In some cases, population of interest (e.g., non-host) sequences in a sample of nucleic acids such as circulating nucleic acids may be sequenced by: (a) providing a sample of nucleic acids, where the sample of nucleic acids comprises background population (e.g., host) nucleic acids and population of interest nucleic acids; (b) mixing the sample of nucleic acids with a collection of oligonucleotides, thereby obtaining a mixture, where the collection of oligonucleotides contains oligonucleotides with a domain of nucleotides; and (c) within the mixture, contacting the collection of oligonucleotides to the sample of nucleic acids, where the contacting causes population of interest nucleic acids within the mixture to bind the domains of nucleotides; and (d) sequencing the bound population of interest nucleic acids by conducting a sequencing assay (e.g., a Next Generation sequencing assay, a high-throughput sequencing assay, a massively parallel sequencing assay, a Nanopore sequencing assay, or a Sanger sequencing assay). In some cases, prior to sequencing, the bound population of interest nucleic acids are preferentially amplified in a reaction (e.g., a PCR reaction). In some cases, prior to sequencing, the bound population of interest nucleic acids are preferentially isolated (e.g., by performing a pull-down assay). In some cases, prior to sequencing, a primer extension reaction is performed on the bound population of interest nucleic acids (e.g., to attach a nucleic acid label to the bound nucleic acids). In some cases, the bound population of interest nucleic acids are RNA. In some cases, a polymerization reaction is performed on the bound population of interest nucleic acids that are RNA (e.g., by reverse transcriptase).

Contacting a collection of oligonucleotides to a sample of nucleic acids such as circulating nucleic acids may cause a portion of the background population (e.g., host) nucleic acids to bind the domains of nucleotides. In some cases, contacting causes about 0.1, 0.5, 1, 2, 3, 4, 5, 6, 7, 8, 9, 10, 11, 12, 13, 14, 15, 20, 25, 30, 35, 40, 45, or 50% of the background population nucleic acids to bind the domains of nucleotides. In some cases, contacting causes up to 0.1, 0.5, 1, 2, 3, 4, 5, 6, 7, 8, 9, 10, 11, 12, 13, 14, 15, 20, 25, 30, 35, 40, 45, or 50% of the background population nucleic acids to bind the domains of nucleotides. In some cases, contacting causes at least 0.1, 0.5, 1, 2, 3, 4, 5, 6, 7, 8, 9, 10, 11, 12, 13, 14, 15, 20, 25, 30, 35, 40, 45, or 50% of the background population nucleic acids to bind the domains of nucleotides.

The collection of oligonucleotides may be provided in excess quantities relative to the sample nucleic acids. The ratio of oligonucleotides to sample nucleic acids may be about 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to sample nucleic acids may be up to 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to sample nucleic acids may be at least 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to sample nucleic acids may be saturating. The ratio of oligonucleotides to sample nucleic acids may be non-saturating. The ratio may be calculated in terms of concentration, moles, or mass.

The collection of oligonucleotides may be provided in excess quantities relative to the population of interest nucleic acids. The ratio of oligonucleotides to population of interest nucleic acids may be about 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to population of interest nucleic acids may be up to 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to population of interest nucleic acids may be at least 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of oligonucleotides to population of interest nucleic acids may be saturating. The ratio of oligonucleotides to population of interest nucleic acids may be non-saturating. The ratio may be calculated in terms of concentration, moles, or mass.

In some cases, the nucleic acids, such as circulating nucleic acids or a sequencing-ready library, are single-stranded. In some cases, double-stranded nucleic acids are denatured into single-stranded nucleic acids. Nucleic acids may be denatured using heat. In some cases, nucleic acids are heated to about 35, 40, 45, 50, 55, 60, 65, 70, 75, 80, 85, 90, 91, 92, 93, 94, 95, 96, 97, 98, or 99° C. In some cases, nucleic acids are heated for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes. In some cases, nucleic acids are denatured using a chemical denaturant (e.g., acid, base, solvent, chaotropic agent, salt).

A sample of single-stranded nucleic acids, such as single-stranded circulating nucleic acids or a sequencing-ready library, may be renatured or hybridized. In some cases, a sample of single-stranded nucleic acids is hybridized with a collection of oligonucleotides. In some cases, a collection of oligonucleotides is hybridized with blocker oligonucleotides. In some cases, at least a portion of the single-stranded nucleic acids is renatured or hybridized. In some cases, nucleic acids are renatured or hybridized at about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 40, 45, 50, 55, 60, 65, 68, or 70° C. In some cases, nucleic acids are renatured or hybridized on ice. In some cases, nucleic acids are renatured or hybridized at room temperature. In some cases, nucleic acids are renatured or hybridized for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes or 2, 3, 4, 5, 10, 15, 20, 22, 24, 30, 40, 46, 48, 50, 60, 70, 72, 80, or 96 hours. Temperature, buffer composition, reaction time, and concentration can affect the extent of hybridization. In some cases, nucleic acids are renatured in the presence of trimethylammonium chloride.

Self-Hybridization Method

Additional methods and compositions for priming, capturing or enriching for a population of interest within a nucleic acid sample are provided herein as well. In some cases, a population of interest is enriched by a self-hybridization method, for example a method that exploits hybridization kinetics based on concentration. Nucleic acid hybridization kinetics are dependent on the concentration of the hybridizing strands. In general, high concentration nucleic acids hybridize more quickly than low concentration nucleic acids. In complex populations of nucleic acids, abundant nucleic acids (e.g., a background population) hybridize faster than rare nucleic acids (e.g., a population of interest). This concentration dependence can be used to reduce the amount of abundant nucleic acids and enrich the amount of rare nucleic acids in a sample by removing at least a portion of double-stranded nucleic acids or isolating at least a portion of single-stranded nucleic acids after partial hybridization of a population of nucleic acids. As a result, the quantity of background population (e.g., human) nucleic acids may be reduced, and the amount of population-of-interest (e.g., non-human, microbial, or pathogen) nucleic acids may be enriched.

In some cases, a sample of DNA (e.g., circulating DNA or circulating cell-free DNA) comprising background population DNA (e.g., human DNA) and population-of-interest DNA (e.g., non-human or pathogen DNA) is obtained. The nucleic acids in the sample may be denatured to produce a sample of single-stranded DNA. In some cases, the nucleic acids in the sample are single-stranded DNA and denaturation is not necessary. In some cases, the sample is then renatured for a defined period of time in a defined buffer, with the expectation that the background population DNA hybridizes faster than the population-of-interest DNA since the background population DNA is present at a higher concentration than the population of interest DNA. The sample may then be subjected to conditions to remove double-stranded DNA—such as by using a duplex-specific nuclease—thereby preferentially removing the background population DNA in the sample. In some cases, a sample comprising RNA is combined with a mixture of single-stranded background population (e.g., human) exome sequences. In some cases, the sample is renatured for a defined period of time, permitting the more abundant exome sequences to hybridize to the RNA. DNA-RNA duplexes are then removed, thereby preferentially removing the background population (e.g., human) RNA in the sample.

In some cases, the nucleic acids such as circulating nucleic acids are single-stranded. In some cases, double-stranded nucleic acids are denatured into single-stranded nucleic acids. In some cases, about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the nucleic acids are single-stranded. In some cases, up to 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the nucleic acids are single-stranded. In some cases, at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the nucleic acids are single-stranded. Nucleic acids may be denatured using heat. In some cases, nucleic acids are heated to about 35, 40, 45, 50, 55, 60, 65, 70, 75, 80, 85, 90, 91, 92, 93, 94, 95, 96, 97, 98, or 99° C. In some cases, nucleic acids are heated up to 35, 40, 45, 50, 55, 60, 65, 70, 75, 80, 85, 90, 91, 92, 93, 94, 95, 96, 97, 98, or 99° C. In some cases, nucleic acids are heated to at least 35, 40, 45, 50, 55, 60, 65, 70, 75, 80, 85, 90, 91, 92, 93, 94, 95, 96, 97, 98, or 99° C. In some cases, nucleic acids are heated for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes. In some cases, nucleic acids are heated for up to 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes. In some cases, nucleic acids are heated for at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes. In some cases, nucleic acids are denatured using a chemical denaturant (e.g., acid, base, solvent, chaotropic agent, salt).

A sample of single-stranded nucleic acids such as single-stranded circulating nucleic acids may be renatured or hybridized. In some cases, at least a portion of the single-stranded nucleic acids is renatured or hybridized. In some cases, about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the single-stranded nucleic acids are renatured or hybridized. In some cases, up to 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the single-stranded nucleic acids are renatured or hybridized. In some cases, at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the single-stranded nucleic acids are renatured or hybridized. In some cases, nucleic acids are renatured or hybridized at about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 40, 45, 50, 55, 60, 65, 68, or 70° C. In some cases, nucleic acids are renatured or hybridized at up to 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 40, 45, 50, 55, 60, 65, 68, or 70° C. In some cases, nucleic acids are renatured or hybridized at least at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 40, 45, 50, 55, 60, 65, 68, or 70° C. In some cases, nucleic acids are renatured or hybridized on ice. In some cases, nucleic acids are renatured or hybridized at room temperature. In some cases, nucleic acids are renatured or hybridized for about 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes or 2, 3, 4, 5, 10, 15, 20, 22, 24, 30, 40, 46, 48, 50, 60, 70, 72, 80, or 96 hours. In some cases, nucleic acids are renatured or hybridized for up to 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes or 2, 3, 4, 5, 10, 15, 20, 22, 24, 30, 40, 46, 48, 50, 60, 70, 72, 80, or 96 hours. In some cases, nucleic acids are renatured or hybridized for at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, or 60 minutes or 2, 3, 4, 5, 10, 15, 20, 22, 24, 30, 40, 46, 48, 50, 60, 70, 72, 80, or 96 hours. Temperature, buffer composition, reaction time, and concentration can affect the extent of hybridization. In some cases, nucleic acids are renatured in the presence of trimethylammonium chloride.

Upon renaturation, single-stranded nucleic acids can hybridize or reanneal into double-stranded nucleic acids. In some cases, a double-stranded nucleic acid is double-stranded DNA, double-stranded RNA, or a DNA-RNA duplex. At least a portion of double-stranded nucleic acids may be removed to generate an enriched population of nucleic acids. In some cases, about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the double-stranded nucleic acids are removed. In some cases, up to 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the double-stranded nucleic acids are removed. In some cases, at least 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% of the double-stranded nucleic acids are removed.

In some cases, at least a portion of double-stranded nucleic acids are removed to generate an enriched population of nucleic acids. In some cases, at least a portion of single-stranded nucleic acids are isolated to generate an enriched population of nucleic acids. In some cases, at least a portion of double-stranded nucleic acids are removed using a separation method such as gel electrophoresis or capillary electrophoresis. In some cases, at least a portion of single-stranded nucleic acids are isolated using a separation method such as gel electrophoresis or capillary electrophoresis. In some cases, at least a portion of double-stranded nucleic acids are removed using one or more nucleases. In some cases, the nuclease acts on double-stranded nucleic acids. In some cases, the nuclease acts on double-stranded DNA. In some cases, the nuclease acts on DNA-RNA duplexes. In some cases, the nuclease does not act on single-stranded nucleic acids. In some cases, the nuclease does not act on single-stranded DNA. In some cases, the nuclease does not act on single-stranded RNA. Some non-limiting examples of a nuclease include duplex specific nuclease (DSN) (e.g., from kamchatka crab), thermolabile DSN-TL, BAL-31, double-strand specific DNase (e.g., from Northern shrimps Pandalus borealis), Exonuclease III, and secreted endonuclease (e.g., from Culex quinquefasciatus). Temperature, buffer composition, reaction time, concentration, and nuclease to substrate ratio can affect nuclease specificity or activity. For example, the substrate preference of the double-strand specific DNase from Northern shrimps is reported to be for double-stranded DNA in the presence of magnesium, but the nuclease becomes active against single-stranded DNA in the presence of calcium (Nilsen et al. "The Enzyme and the cDNA Sequence of a Thermolabile and Double-Strand Specific DNase from Northern Shrimps (Pandalus borealis) PLOS One 2010). A combination of nucleases may be used in series or in parallel. In some cases, nucleic acids are purified after nuclease treatment to replace the buffer composition and/or to remove nucleases, nucleotides, and/or short nucleic acid fragments.

In some cases, a sample comprising nucleic acids is combined with a mixture of single-stranded background population (e.g., human) nucleic acids. The sample is renatured for a defined period of time, permitting the more abundant background population nucleic acids to hybridize to nucleic acids in the sample. Double stranded nucleic acids are then removed, thereby preferentially removing the background population (e.g., human) nucleic acids in the sample. In some cases, the sample comprises RNA. In some cases, the double stranded nucleic acid is a DNA-RNA duplex. In some cases, the background population nucleic acids are exome sequences. In some cases, the depleting is accomplished by contacting the sample comprising nucleic acids with background population nucleic acids such that the background population nucleic acids hybridize, or otherwise specifically bind to, complementary or nearly complementary background population nucleic acids within the sample. In some cases, the method further comprises denaturing at least a portion of the background population nucleic acids, e.g., by heat. In some cases, the background population nucleic acid sequences may be identified bioinformatically or computationally. In some cases, the background population nucleic acids are synthesized. In some cases, the background population nucleic acids are DNA.

The background population nucleic acids may be provided in excess quantities relative to the sample nucleic acids. The ratio of background population nucleic acids to sample nucleic acids may be about 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population nucleic acids to sample nucleic acids may be up to 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population nucleic acids to sample nucleic acids may be at least 0.1; 0.2; 0.3; 0.4; 0.5; 0.6; 0.7; 0.8; 0.9; 1.0; 1.1; 1.2; 1.3; 1.4; 1.5; 1.6; 1.7; 1.8; 1.9; 2.0; 2.5; 3.0; 3.5; 4.0; 4.5; 5.0; 5.5; 6.0; 6.5; 7.0; 7.5; 8.0; 8.5; 9.0; 9.5; 10; 11; 12; 13; 14; 15; 16; 17; 18; 19; 20; 25; 30; 35; 40; 45; 50; 55; 60; 65; 70; 75; 80; 85; 90; 95; 100; 200; 300; 400; 500; 600; 700; 800; 900; 1,000; 2,000; 3,000; 4,000; 5,000; 6,000; 7,000; 8,000; 9,000; or 10,000. The ratio of background population to sample nucleic acids may be saturating. The ratio of background population to sample nucleic acids may be non-saturating. The ratio may be calculated in terms of concentration, moles, or mass.

In some cases, at least a portion of double stranded nucleic acids are removed to generate an enriched population of nucleic acids. The background population nucleic acids may be chemically labeled and removed, thereby removing double stranded nucleic acids. The background population nucleic acids may be conjugated to magnetic beads and removed with a magnet, thereby removing double stranded nucleic acids. The background population nucleic acids may be labeled with a nucleic acid label. The nucleic acid label may bind to or hybridize to a nucleic acid sequence that is conjugated to a solid support or tagged with a chemical label. Double stranded nucleic acids may be removed by size separation (e.g., gel electrophoresis, capillary electrophoresis, etc.), affinity separation (e.g., a pull-down assay, chromatography, etc.), or other methods. In some cases, double stranded nucleic acids may be isolated based on differences in size of single-stranded nucleic acids and double stranded nucleic acids using a separation method such as gel electrophoresis, capillary electrophoresis, or chromatography. In some cases, non-hybridized background population nucleic acids are not removed.

Enrichment by Nucleosome Depletion

Figure 6:
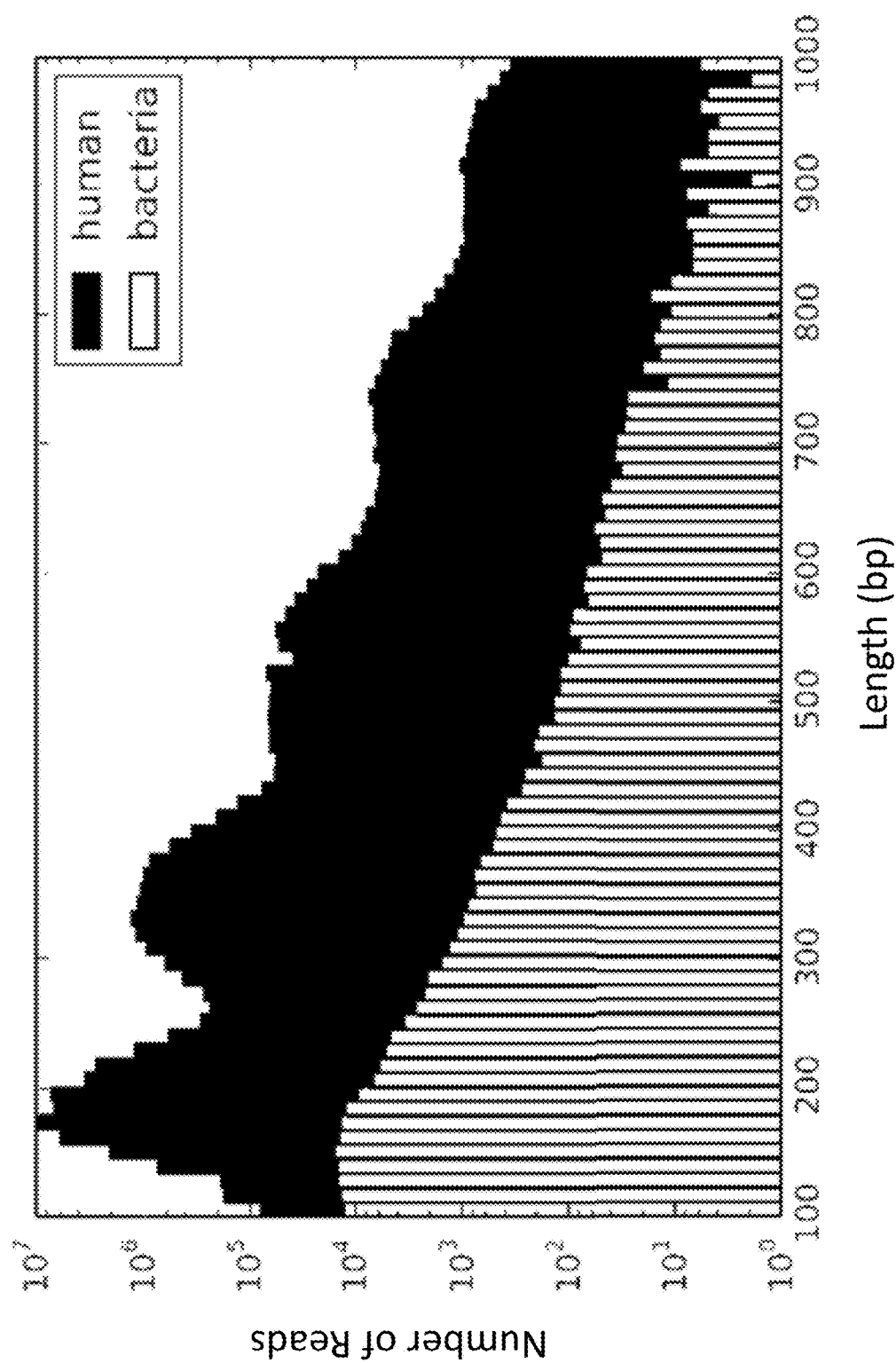
FIG. 6 shows periodicity of human cell-free DNA length.

Another example of an enrichment method provided herein is a nucleosome depletion method. Purified human cell-free DNA has a length periodicity of approximately 180 base pairs, as shown in FIG. 6, suggesting that the majority of human cell-free DNA is histone associated in nucleosomes. Bacterial DNA does not exhibit specific length periodicity, as shown in FIG. 6. Depleting nucleosomal or nucleosome-associated DNA may provide a method for enriching a population of interest.

In some cases, methods to separate nucleosomal DNA or nucleosome-associated DNA from free DNA (e.g., non-nucleosomal DNA or non-nucleosome-associated DNA) include electrophoresis and isotachophoresis to separate based on mass and/or net charge, porous filters to separate based on shape and/or size, ion exchange column to separate based on charge (nucleosomes have histones with positively charged tails, DNA has a negatively charged backbone), and antibodies specific to host histones to immuno-deplete host nucleosomes and associated DNA. In some cases, a portion of host nucleic acid is nucleosome-associated and a portion of host nucleic acid is not nucleosome-associated.

In some cases, one or more antibodies may be used to immuno-deplete histones or nucleosomes, as shown in FIG. 7. In some cases, an antibody (750) may be specific to a background population (e.g., host) histone or nucleosome (710). In some cases, an antibody may be specific to a mammalian histone or nucleosome. In some cases, an antibody may be specific to a human histone or human nucleosome. In some cases, one or more antibodies are specific to one or more histones. In some cases, the histone may be a histone variant or have a histone modification. In some cases, immunodepletion may retain population of interest (e.g., non-host) nucleosomal DNA (730), population of interest non-nucleosomal DNA (740), and background population (e.g., host) non-nucleosomal DNA (720). In some cases, immunodepletion may comprise immunoprecipitation, chromatin immunoprecipitation, bulk binding of the antibody, or affinity chromatography with column immobilized antibody. In some cases, the one or more antibodies are immobilized on a column. In some cases, the one or more antibodies are removed (e.g., using anti-immunoglobulin antibodies conjugated to beads or attached to a column). In some cases, the one or more antibodies are monoclonal. In some cases, the one or more antibodies are target the C-terminal end of one or more histones. In some cases, the one or more antibodies are target the N-terminal end of one or more histones.

Non-limiting examples of histones, histone variants, and histone modifications include Histone H2A N-terminus, Histone H2A solvent exposed epitope, mono-methylation on Lys9 in Histone H3, di-methylation on Lys9 in Histone H3, trimethylation on Lys56 in Histone H3, phosphorylation on Ser14 in Histone H2B, phosphorylation on Ser139 in Histone H2A.X, H2A-H2B Acidic Patch motif, Histone H1, Histone H1.0, Histone H1.1, Histone H1.2, Histone H1.3, Histone H1.4, Histone H1.5, Histone H1.00, Spermatid-specific linker histone H1-like protein, Histone H1t, Histone H1t2, Histone H1FNT, Histone H2A type 1-B/E (e.g., Histone H2A.2, Histone H2A/a, Histone H2A/m), Histone H2A type 2-A (e.g., Histone H2A.2, Histone H2A/o) Histone H2A type 1-D (e.g., Histone H2A.3, Histone H2A/g), Histone H2A type 1 (e.g., H2A.1, Histone H2A/p), Histone H2A type 2-C (e.g., Histone H2A-GL101, Histone H2A/q), Histone H2A type 1-A (e.g., Histone H2A/r), Histone H2A type 1-C (e.g., Histone H2A/l), Histone H2A type 1-H (e.g., Histone H2A/s), Histone H2A type 1-J (e.g., Histone H2A/e), Histone H2A type 2-B, Histone H2A type 3, Histone H2AX (e.g., H2a/x, Histone H2A.X, Histone H2A.Z, H2A/z, H2A.Z.1, H2A.Z.2), Histone H2A.V (e.g., H2A.F/Z), Histone H2A.J (e.g., H2a/j), mH2A1, mH2A2, Histone H2A-Bbd type 1 (e.g., H2A Barr body-deficient, H2A.Bbd), Histone H2A-Bbd type 2/3 (e.g., H2A Barr body-deficient, H2A.Bbd), Core histone macro-H2A.1 (e.g., Histone macroH2A1, mH2A1, Histone H2A.y, H2A/y, Medulloblastoma antigen MU-MB-50.205, macroH2A), Core histone macroH2A.2, Histone H2A, Histone H2A.J, Histone H2B, Histone H2B type 1-C/E/F/G/I (e.g., Histone H2B.1 A, Histone H2B.a, H2B/a, Histone H2B.g, H2B/g, Histone H2B.h, H2B/h, Histone H2B.k, H2B/k, Histone H2B.1, H2B/l), H2BE, Histone H2B type 1-H, Histone H2B type 1-A (e.g., Histone H2B from testis, TSH2B.1, Testis-specific histone H2B, TSH2B), Histone H2B type 1-B (e.g., Histone H2B.1, Histone H2B.f, H2B/f), Histone H2B type 1-D (e.g., HIRA-interacting protein 2, Histone H2B.1 B, Histone H2B.b, H2B/b), Histone H2B type 1-J (e.g., Histone H2B.1, Histone H2B.r, H2B/r), Histone H2B type 1-O (e.g., Histone H2B.2, Histone H2B.n, H2B/n), Histone H2B type 2-E (e.g., Histone H2B-GL105, Histone H2B.q, H2B/q), Histone H2B type 1-H (e.g., Histone H2B.j, H2B/j), Histone H2B type 1-M (e.g., Histone H2B.e, H2B/e), Histone H2B type 1-L (e.g., Histone H2B.c, H2B/c), Histone H2B type 1-N (e.g., Histone H2B.d, H2B/d), Histone H2B type F-S (e.g., Histone H2B.s, H2B/s), Putative histone H2B type 2-C (e.g., Histone H2B.t, H2B/t), Histone H2B type 1-K (e.g., H2B K, HIRA-interacting protein 1), Histone H2B type 2-F, Histone H2B type 2-E, Histone H2B type 3-B (e.g., H2B type 12), Histone H2B type F-M (e.g., Histone H2B.s, H2B/s), Putative histone H2B type 2-D, Histone H2B type W-T (e.g., H2B histone family member W testis-specific), Histone 1 H2bn isoform CRA_b, Histone H2B type 1-N, H2B histone family member M, Histone H2B type F-M, Histone H2B type 1-J, H2BFWT, Histone H3, Histone H3.1 (e.g., Histone H3/a, Histone H3/b, Histone H3/c, Histone H3/d, Histone H3/f, Histone H3/h, Histone H3/i, Histone H3/j, Histone H3/k, Histone H3/l), Histone H3.2 (e.g., Histone H3/m, Histone H3/o), Histone H3.3C (e.g., Histone H3.5), Histone H3.1t (e.g., H3/t, H3t, H3/g), Histone H3.3, Histone H3-like centromeric protein A (e.g., Centromere autoantigen A, Centromere protein A, CENP-A), Histone H3.3 (cDNA FLJ57905), Histone H3.4, Histone H3.5, Histone H3.X, Histone H3.Y, Histone H4, Histone H4-like protein type G, HIST1H4J protein, Homo sapiens H4 histone family member N, and Histone H5.

A method may deplete background population nucleosome-associated DNA. Background population nucleosome-associated DNA may be depleted by about 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%. Background population nucleosome-associated DNA may be depleted by up to 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%. Background population nucleosome-associated DNA may be depleted by at least 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%.

Enrichment by Removing or Isolating DNA of Specific Length Intervals

In some cases, an enrichment method provided herein involves removing DNA of specific length intervals such as cell-free DNA of specific length intervals and/or isolating DNA of specific length intervals such as cell-free DNA of specific length intervals. In one example, in a cell-free DNA sample, a ratio of host to non-host cell-free DNA can vary significantly with some predictability, such that there may be cell-free DNA length ranges in which the ratio of host to non-host DNA may be at a local minimum. Where one may be interested in analyzing non-host DNA in a cell-free sample, one may enrich for non-host DNA relative to the host DNA by enriching for the DNA length ranges at which the ratio of non-host to host DNA is more favored. By way of example, FIG. 6 illustrates a plot comparing DNA length in a human derived sample, where the upper bars reflect the host or human DNA, while the lower bars represent non-host DNA. In many cases, the association of human DNA with histones results in a first sized fragment that occurs of approximately 175 bases in length as well as fragments that are approximately 147 bases in length (i.e., reflecting DNA lengths wrapped around a single histone core). As shown in FIG. 6, the peaks show size distribution of the human DNA that provides local maxima and local minima at other fragment lengths as well.

By selecting size ranges where the host to non-host DNA ratio is at a low point, e.g., as shown, less than about 120 bp, from about 240 to about 280 bp, or from about 425 to about 475 by in length, one can relatively enrich for the non-host DNA. Thus, in accordance with certain aspects of the disclosure, cell-free nucleic acid samples are enriched for relatively short fragments in order to enrich for non-host nucleic acids over host nucleic acids. In many cases, enrichment processes enrich for fragments of lengths from about 10 bases in length to about 300 bases in length, from about 10 bases in length to about 200 bases in length, from about 10 bases in length to about 175 bases in length, from about 10 bases in length to about 150 bases in length, from about 10 to 120 bases in length, from about 10 to about 60 bases in length, from about 30 bases in length to about 300 bases in length, from about 30 bases in length to about 200 bases in length, from about 30 bases in length to about 175 bases in length, from about 30 bases in length to about 150 bases in length, from about 30 to 120 bases in length, or from about 30 to about 60 bases in length. As will be appreciated, selection of upper and lower limits of the selection process may target any of the above-described lower and upper limits of size selection. As will be appreciated, the above-described size selection is not intended to recite exact sizes, but will focus size selection around the ranges described above with an ordinary size distribution around the described fragment sizes. By way of example, where recited as selecting a given fragment size range, it will be appreciated that a predominant size range within an enriched sample will fall into that range, e.g., at least 50%, at least 60%, at least 70%, at least 80%, or in some cases, at least 90% of the fragments in the enriched sample will reflect the recited size range. In other cases, it will be appreciated that the fragments reflected in an enriched sample will include fragments that are substantially no more than about 30% outside of the recited upper and lower limits of the ranges, no more than 20%, no more than 10%, and in some cases, no more than 5% outside the upper or lower limits of the range.

In such a method, a sample of nucleic acids (e.g., a sample of circulating DNA) is obtained comprising population of interest (e.g., pathogen) DNA and background population (e.g., human) DNA. In some cases, DNA of specific length intervals may be enriched for background population DNA and may be depleted from the sample, thereby preferentially enriching for population-of-interest DNA. In some cases, DNA of specific length intervals may be enriched for population-of-interest DNA and may be isolated from the sample, thereby preferentially enriching for population of interest DNA. In some cases, methods to remove and/or isolate DNA of specific length intervals include electrophoresis (e.g., gel electrophoresis or capillary electrophoresis), chromatography (e.g., liquid chromatography), cell-free nucleic acid purification (e.g., silica membrane column, buffer optimization), and/or mass spectrometry to separate based on mass, size, and/or net charge.

In some cases, cell-free nucleic acid purification can be performed using a silica membrane (e.g., a silica membrane column such as QIAamp Mini column) or a commercial kit (e.g., QIAamp Circulating Nucleic Acid Kit). In general, cell-free nucleic acid purification comprises four steps: lysis, binding, washing, and elution.

The lysis step may release nucleic acids from proteins, lipids, and/or vesicles, may inactivate DNases and/or RNases, and may occur under denaturing conditions, at elevated temperatures, and/or in the presence of proteinase K. The lysis step may use Buffer ACL and/or proteinase K.

The binding step may bind or adsorb the nucleic acids onto the silica membrane. The binding step may use Buffer ACB or a binding buffer comprising about or at least about 35%, 40%, 45%, 50%, 55%, 60%, 65%, 66%, 70%, or 75% alcohol (e.g., isopropanol) by volume, for example a binding buffer comprising about 40% or about 66% isopropanol. In some cases, additional commercial buffer (e.g., Buffer ACB) is used during cell-free nucleic acid purification relative to a manufacturer's recommended protocol. For example, in some cases, the volume of additional commercial buffer added is about or at least about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6.0, 7.0, 8.0, 9.0, or 10.0 times the volume specified in the manufacturer's recommended protocol. In some cases, about or at least about 1.5, 1.8, 2.0, 2.5, 3.0, 3.5, 4.0, 5.0, 5.3, 5.4, 5.5, 6.0, 7.0, 8.0, 9.0, 10.0, 11.0, 12.0, 13.0, 14.0, 15.0, or 16.0 mL of a binding buffer or Buffer ACB is used per silica membrane column or per lysate from 1 mL sample (e.g., serum or plasma).

The washing step may remove residual contaminants and may comprise multiple washing steps. A washing step may use Buffer ACW1, Buffer ACW2, ethanol, and/or a wash buffer comprising about or at least about 50%, 55%, 56.8%, 60%, 65%, 66%, 69.8%, 70%, 75%, 80%, 85%, 86%, 87%, 87.4%, 88%, 89%, 90%, 95%, 96%, 97%, 98%, 99%, or 100% alcohol (e.g., ethanol) by volume, for example a wash buffer comprising about 56.8%, about 69.8%, about 87.4%, about 89%, or about 100% ethanol. In some cases, ethanol can refer to 96-100% ethanol. In some cases, the ethanol is not denatured alcohol. In some cases, the ethanol does not contain methanol or methylethylketone. In some cases, the washing step may include a first washing step with Buffer ACW1 (e.g., 600 µL per silica membrane column), a second washing step with Buffer ACW2 (e.g., 750 µL per silica membrane column), and a third washing step with ethanol (e.g., 750 µL per silica membrane column). In some cases, additional ethanol (e.g., absolute ethanol) is added to a commercial buffer (e.g., Qiagen ACW1 buffer, ACW2 buffer) during cell-free nucleic acid purification relative to a manufacturer's recommended protocol. For example, in some cases, the volume of additional ethanol added is about or at least about 0.5, 0.6, 0.7, 0.8, 0.9, 1.0, 1.05, 1.1, 1.2, 1.3, 1.4, 1.5, 1.6, 1.7, 1.75, 1.8, 1.9, 2.0, 2.5, 3.0, 3.5, 4.0, 4.5, 5.0, 6.0, 7.0, 8.0, 9.0, or 10.0 mL per 600 µL or 750 µL of commercial buffer. In some cases, the volume of additional ethanol added is up to about 0.5, 0.6, 0.7, 0.8, 0.9, 1.0, 1.05, 1.1, 1.2, 1.3, 1.4, 1.5, 1.6, 1.7, 1.75, 1.8, 1.9, 2.0, 2.5, 3.0, 3.5, 4.0, 4.5, 5.0, 6.0, 7.0, 8.0, 9.0, or 10.0 mL per 600 µL or 750 µL of commercial buffer.

In some cases, additional guanidinium chloride is added to a commercial buffer (e.g., Qiagen ACW1 buffer) during cell-free nucleic acid purification relative to a manufacturer's recommended protocol. For example, in some cases, the amount of additional guanidinium chloride added is about or at least about 0.1, 0.2, 0.3, 0.31, 0.32, 0.33, 0.34, 0.35, 0.36, 0.37, 0.38, 0.39, 0.4, 0.5, 0.6, 0.7, 0.8, 0.9, 1.0, 1.1, 1.2, 1.3, 1.4, 1.5, 1.6, 1.75, 1.8, 1.9, or 2.0 g per 600 µL of commercial buffer. In some cases, the amount of additional guanidinium chloride added is up to about 0.1, 0.2, 0.3, 0.31, 0.32, 0.33, 0.34, 0.35, 0.36, 0.37, 0.38, 0.39, 0.4, 0.5, 0.6, 0.7, 0.8, 0.9, 1.0, 1.1, 1.2, 1.3, 1.4, 1.5, 1.6, 1.75, 1.8, 1.9, or 2.0 g per 600 µL of commercial buffer or wash buffer. In some cases, a wash buffer can comprise about or at least about 0.1, 0.2, 0.3, 0.31, 0.32, 0.33, 0.34, 0.35, 0.36, 0.37, 0.38, 0.39, 0.4, 0.5, 0.6, 0.7, 0.8, 0.9, 1.0, 1.1, 1.2, 1.3, 1.4, 1.5, 1.6, 1.75, 1.8, 1.9, or 2.0 g guanidinium chloride per 600 µL of wash buffer.

In some cases, additional ethanol (e.g., absolute ethanol) and additional guanidinium chloride are added to a commercial buffer (e.g., Qiagen ACW1 buffer) during cell-free nucleic acid purification relative to a manufacturer's recommended protocol. In some cases, the washing step may include a first washing step with a first wash buffer comprising guanidinium chloride and about 89.0% ethanol, a second washing step with a second wash buffer comprising about 87.4% ethanol, and a third washing step with ethanol. In some cases, each wash buffer comprises at least about 60%, 65%, 66%, 69.8%, 70%, 75%, 80%, 85%, 86%, 87%, or 87.4% ethanol.

The elution step may release the nucleic acids from the silica membrane. The elution may use Buffer AVE.

For example, the manufacturer's recommended protocol for Qiagen Circulating Nucleic Acid (CNA) kit can be modified with the following modifications: (a) 3× volume of ACB Buffer is used, (b) ACW1 Buffer is prepared according to the manufacturer's recommendations and supplemented with an extra 1.75 mL of absolute ethanol and 0.36 g guanidinium chloride per 600 µL of ACW1 Buffer, and (c) ACW2 Buffer is prepared according to the manufacturer's recommendations and supplemented with 1.05 mL of absolute ethanol per 750 µL of ACW2 Buffer.

In addition to other nucleosome targeted depletion methods, as described elsewhere herein, methods of size selection/isolation of nucleic acids are well known in the art. For example, chromatographic methods, such as gel electrophoresis, gel exclusion chromatography methods, and the like, may be used to selectively isolate nucleic acids of desired lengths. Additionally, bead based charge separation methods may be employed to selectively isolate nucleic acids of a desired size range. For example, SPRI bead systems available from, e.g., Beckman Coulter, and AMPure bead systems available from, e.g., New England Biolabs, may be readily used to perform size selection purifications of cell-free DNA that can enrich for non-host DNA relative to the host DNA, as described above.

In some cases, a size selection enrichment may provide an increase in the ratio of non-host to host DNA of at least about 1.5×, at least about 2×, at least about 3×, at least about 4×, at least about 5×, at least about 6×, at least about 7×, at least about 8×, at least about 9×, at least about 10×, at least about 20×, at least about 30×, at least about 40×, at least about 50×, at least about 100×, and in some cases, as high as about 500×, or greater. Solely for purposes of illustration, if the non-host DNA is present in a cell-free sample at a ratio to host DNA of 1:100, enrichment that yields a 2× increase would yield a ratio of 1:50. In some cases, the increase in the ratio of non-host to host DNA will be between about 1.5×, 2×, 3×, 4×, or 5× and about 10×, 20×, 30×, 40×, 50×, 100×, 500× or more.

DNA of one or more length intervals may be removed. In some cases, the one or more length intervals may be selected from one or more multiples of about 140 base pairs, about 145 base pairs, about 150 base pairs, about 155 base pairs, about 160 base pairs, about 165 base pairs, about 170 base pairs, about 175 base pairs, about 180 base pairs, about 185 base pairs, about 190 base pairs, about 195 base pairs, about 200 base pairs, about 205 base pairs, and about 210 base pairs. In some cases, a multiple is, at each occurrence, independently selected from a multiple of 1, 2, 3, 4, 5, 6, 7, 8, 9, and 10. For example, about 180 base pairs is a multiple of 1 for about 180 base pairs, and about 360 base pairs is a multiple of 2 for about 180 base pairs. In some cases, the one or more length intervals may be about 180 base pairs, about 360 base pairs, about 540 base pairs, about 720 base pairs, or about 900 base pairs.

DNA of one or more length intervals may be isolated. In some cases, the one or more length intervals may be selected from about 10 base pairs, about 20 base pairs, about 30 base pairs, about 40 base pairs, about 50 base pairs, about 60 base pairs, about 70 base pairs, about 80 base pairs, about 90 base pairs, about 100 base pairs, about 110 base pairs, about 120 base pairs, about 130 base pairs, about 140 base pairs, about 150 base pairs, about 160 base pairs, about 170 base pairs, up to about 10 base pairs, up to about 20 base pairs, up to about 30 base pairs, up to about 40 base pairs, up to about 50 base pairs, up to about 60 base pairs, up to about 70 base pairs, up to about 80 base pairs, up to about 90 base pairs, up to about 100 base pairs, up to about 110 base pairs, up to about 120 base pairs, up to about 130 base pairs, up to about 140 base pairs, up to about 150 base pairs, up to about 160 base pairs, up to about 170 base pairs, and from one or more multiples of about 70 base pairs, about 75 base pairs, about 80 base pairs, about 85 base pairs, about 90 base pairs, about 95 base pairs, about 100 base pairs, and about 105 base pairs. In some cases, a multiple is, at each occurrence, independently selected from a multiple of 1, 3, 5, 7, 9, 11, 13, 15, 17, and 19. For example, about 90 base pairs is a multiple of 1 for about 90 base pairs, and about 270 base pairs is a multiple of 3 for about 90 base pairs. In some cases, the one or more length intervals may be about 90 base pairs, about 270 base pairs, about 450 base pairs, about 630 base pairs, or about 810 base pairs.

A method may isolate or remove DNA of one or more length intervals. About 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of DNA of a specific length interval may be isolated or removed. Up to 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of DNA of a specific length interval may be isolated or removed. At least 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of DNA of a specific length interval may be isolated or removed.

Exosomes for Background Population Depletion and/or Population of Interest Enrichment Still another example of an enrichment method provided herein involves targeting exosomal nucleic acids within a biological sample obtained from a host in order to either deplete or enrich the sample for population-of-interest (e.g., non-host) nucleic acids. Exosomes and other extracellular vesicles are secreted by cells and are present in biofluids. They may be released by direct budding at the plasma membrane or through the multivesicular body pathway.

In some cases, population of interest (e.g., pathogen, non-human) nucleic acids may be asymmetrically distributed inside or outside of exosomes. In some cases, background population nucleic acids (e.g., human) are asymmetrically distributed inside or outside of exosomes. In cases where population-of-interest (e.g., non-host, pathogen) nucleic acids are present outside of exosomes, the method may involve removing exosomes from a sample in order to enrich for the population of interest nucleic acids external to the exosomes. Similarly, when background population (e.g., host or human) nucleic acids are present within exosomes, the method may comprise removing exosomes in order to enrich for the population-of-interest nucleic acids external to the exosomes. In some cases, exosomes are isolated or removed from a biological sample prior to isolating nucleic acids such as circulating nucleic acids from the sample.

In cases where population-of-interest (e.g., microbial or pathogen) nucleic acids are present within exosomes, the method may comprise capturing exosomes in order to enrich for the population of interest nucleic acids internal to the exosomes. In cases where population of interest nucleic acids are present within, or processed by, white blood cells (e.g., macrophages), the method may comprise preferentially isolating white blood cell-derived exosomes such as by immunoprecipitating the white blood cell-derived exosomes with antibodies. Likewise, in cases where background population (e.g., host or human) nucleic acids are present outside of exosomes, the method may involve capturing exosomes from a sample in order to enrich for the population of interest nucleic acids internal to the exosomes.

In some cases, background population nucleic acids are asymmetrically distributed inside or outside of exosomes. For example, human nucleic acids such as human cell-free nucleic acids may be asymmetrically distributed inside or outside of exosomes. In general, the majority of human cell-free RNA in plasma is found within exosomes, possibly due to an abundance of RNases in plasma. Direct extraction of cell-free RNA using a circulating nucleic acid kit may not yield quality RNA due to degradation of cell-free RNA. Exosome isolation may yield good quality RNA, including intact mRNA, 18S, and 28S ribosomal RNA. The majority of human cell-free mRNA may be within exosomes. Therefore, in some cases, the methods provided herein may comprise depleting exosomes from a sample in order to deplete human cell-free mRNA from the sample. In contrast, generally the majority of human cell-free DNA in plasma may not be in exosomes, possibly because exosomes package cytosol. Therefore, in some cases, the methods provided herein may comprise enriching exosomes in a sample in order to deplete human cell-free DNA from the sample.

In some cases, the method may comprise determining the ratio of population of interest to background population nucleic acid in plasma, isolated exosomes, and/or exosome-depleted plasma. For example, the method may comprise determining the ratio of microbial to human nucleic acid in plasma, isolated exosomes, and/or exosome-depleted plasma. In some cases, the method may comprise determining the ratio of microbial to human DNA in plasma, isolated exosomes, and/or exosome-depleted plasma. In some cases, the method may comprise determining the ratio of microbial to human RNA in plasma, isolated exosomes, and/or exosome-depleted plasma. In some cases, the method may comprise determining the amount, percentage, or concentration of population of interest nucleic acids in plasma, isolated exosomes, and/or exosome-depleted plasma.

In cases where population of interest nucleic acids are present within white blood cells (e.g., macrophages) or processed by white blood cells (e.g., macrophages), the method may comprise preferentially isolating white blood cell-derived exosomes such as by immunoprecipitating the white blood cell-derived exosomes with antibodies. In cases where microbial or pathogen nucleic acids are present within white blood cells or processed by white blood cells, the method may comprise preferentially isolating white blood cell-derived exosomes such as by immunoprecipitating the white blood cell-derived exosomes with antibodies. In some cases, the method may comprise enriching exosomes derived from mammalian white blood cells (e.g., macrophages). In some cases, the method may comprise enriching exosomes derived from human white blood cells (e.g., macrophages). In some cases, the method may comprise enriching exosomes derived from host white blood cell (e.g., macrophages). As exosomes re-enter the blood stream, while most macrophages do not, the method may provide access to information on deep tissue infections.

A method may isolate or remove exosomes. About 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of exosome may be isolated or removed. Up to 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of exosome may be isolated or removed. At least 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of exosome may be isolated or removed. Some non-limiting examples of available kits and protocols for isolating exosomes from plasma include Exo-spin Blood Exosome Purification Kit (Cell Guidance Systems), exoRNeasy Serum/Plasma Kit (Qiagen), Total Exosome Isolation Reagent (Life Technologies), ExoQuick (System Biosciences), Exo-Flow exosome immunopurification (System Biosciences), ME Kit (New England Peptide), Vn96 peptide (New England Peptide), PureExo exosome isolation kit (101 Bio), and Plasma/Serum Circulating and Exosomal RNA Purification Kit (Norgen Biotek Corp).

Targeted Host DNA Depletion

In some cases, depletion of host nucleic acids in a cell-free sample may take advantage of targeting specific sequences, sequence structures, or nucleic acid characteristics or modifications, any one of which may be specific for one of the host or non-host nucleic acids. For example, one may target specific sequence motifs, structures, base modifications, etc. as a mechanism for binding, pulling out, precipitating, digesting, or otherwise removing or selecting for one of the host or non-host nucleic acids. By way of example, in many cases, human nucleic acids may include base modifications that may not be reflected in non-host or pathogen associated nucleic acids. Such modifications include, for example, methylation patterns, such as cytosine methylation. For example, methyl-cytosine may be found in CpG islands in higher organisms. While present in some eukaryotic pathogens, its presence is considerably higher in vertebrates, as compared to any other organisms.

In some cases, one may target these types of modification using endonucleases that are specific for methylated motifs (e.g., McrBC, FspEI, LpnPI, MspJI endonucleases). These endonucleases often require two base modifications in close proximity to perform the digestion. The separation may be any length between 50 by and 3 kbp, for example, at least 50 bp, at least 60 bp, at least 70 bp, at least 80 by at least 90 bp, at least 100 bp, at least 200 bp, at least 300 bp, at least 400 bp, at least 500 bp, at least 600, at least 700 bp, at least 800 bp, at least 900 bp, at least 1 kbp, at least 1.5 kbp, at least 2 kbp, at least 2.5 kbp, or at least 3 kbp. This may result in poor digestion efficiency of the human cfDNA fragments as they are mostly 147-175 by in length. This may be improved by introducing partner base modification in one of the two adapters provided in the ligation step during preparation of the sequencing library. For example, P5 sequence-carrying adapter may include methyl-cytosine in a CpG island to stimulate McrBC digestion post-ligation even, if only one methyl-cytosine is present in the original human cfDNA fragment. Accordingly, in some cases, a "helper" modified base may be artificially introduced into a sequence library, by including a methylated base within an adapter sequence used in preparing a sequence library. Thus, a digestion step could be employed after adapter ligation to sequence fragments, in order to pre-digest the host derived library elements, while allowing the non-host derived library elements to proceed through amplification and sequencing.

In an alternative, or additional approach, one may employ paired recognition sequences that may require spacing distances between two or more of such sites, in order to selectively or preferentially digest sequences longer than such required separation distances. For example, in the case of McrBC endonucleases that may recognize two methylated cytosines that are 50 or more bases apart (e.g., from 50 by to about 3 kbp), one may provide methylated bases upon the adapter sequences attached to either end. As a result, fragments that maintain more than 50 bases between the methylated bases on the opposing adapters will be digested by the McrBC endonuclease, enriching the sample for shorter nucleic acid fragments that result in greater enrichment for non-host fragments, as described elsewhere herein.

Combined Enrichment Approaches

Although the foregoing enrichment schemes are described individually, it will be appreciated that any or all of the aforementioned processes may be used in various combinations in enriching for non-host DNA in samples relative to the host DNA. For example, cell-free samples may initially be subjected to a size selection based DNA purification scheme, e.g., using a SPRI bead system, followed by one or more of a chromatographic size selection scheme, a nucleosome immune-precipitation scheme, or the like.

Again, as noted above, in some cases, single step or multi step enrichment of non-host DNA can result in an increase in the ratio of non-host to host DNA in a sample of from about 2× to about 10,000×. In some cases, the ratio may be increased by at least 2×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 30×, at least 40×, at least 50×, at least 60×, at least 70×, at least 80×, at least 90×, at least 100×, at least 1000×, at least 5000×, or in some cases, at least 10,000×.

Molecular Barcoding of Samples by Nucleic Acid Spike-In

Samples may be barcoded with nucleic acid barcode spike-ins. The nucleic acid barcodes may be one or more lengths. In some cases, the nucleic acid barcodes may be oligonucleotides, duplex longmers, PCR products, and/or plasmids. In some cases, the nucleic acid barcodes may be DNA, RNA, PNA, LNA, BNA, or any combination thereof. In some cases, the nucleic acid barcodes may comprise sequences absent from one or more background populations, e.g., a human genome or pathogen genome. In some cases, the nucleic acid barcodes may comprise sequences absent from one or more populations of interest.

In some cases, barcodes are part of the sample, unlike labels on the outside of a sample tube. In some cases, barcodes can be added at any stage, including prior to addition of a biological sample, and can be read-out at any stage (e.g., by PCR or sequencing). In some cases, barcodes can be used to track samples, detect cross-contamination, and/or track reagents. In some cases, barcodes can be used to reduce sample mix-up. In some cases, nucleic acid barcodes may be used to increase total nucleic acid concentrations to increase recovery of low concentration samples. In some cases, barcodes may be used to compare a known input with a measured output or to infer sample input by providing a reference standard (e.g., normalization oligonucleotides) for comparison or normalization. In some cases, barcodes may be used to improve performance through quality control and development by measuring library complexity, sample loss, sensitivity, and/or size bias.

In some cases, a sample (e.g., a biological sample or sample of nucleic acids) may be spiked with normalization oligonucleotides. In some cases, the normalization oligonucleotides may be used to monitor the efficiency of DNA manipulation, purification, and/or amplification steps. For example, the absolute number of population of interest (e.g., non-host or pathogen) sequencing reads may be compared to the absolute number of recovered normalization oligonucleotide reads to normalize for differences in molecular manipulation efficiencies between samples. In some cases, the normalization oligonucleotides may be used for barcoding purposes or for both normalization and barcoding purposes.

Strategic Capture of Regions of Interest

The collections of oligonucleotides and methods provided herein may further comprise oligonucleotides containing nucleic acids sequences identical to, nearly identical to, complementary to, or nearly complementary to a region of interest. Some non-limiting examples a region of interest include pathogenicity loci (e.g., the pathogenicity locus in Clostridium difficile); antimicrobial resistance markers; antibiotic resistance markers; antiviral resistance markers; antiparasitic resistance markers; informative genotyping regions (e.g., from a host, human, microbe, pathogen, bacteria, virus, fungus, or parasite); sequences common among two or more microbes, pathogens, bacteria, viruses, fungi, and/or parasites; non-host sequences integrated into the host genome; masking non-host sequences; non-host mimicking sequences; masking host sequences; host mimicking sequences; and sequences specific to one or more microbes, pathogens, bacteria, viruses, fungi, or parasites. In some cases, a region of interest may be present in a non-host, bacterial, viral, pathogen, fungal, or microbial genome. In some cases, a region of interest may be present in a host, mammalian, or human genome. The inclusion of nucleic acid sequences identical to, nearly identical to, complementary to, or nearly complementary to a region of interest may enable genotyping, antimicrobial resistance detection, antibiotic resistance detection, antiviral resistance detection, antiparasitic resistance detection, and/or enhanced pathogen detection sensitivity. The nucleic acid sequences identical to, nearly identical to, complementary to, or nearly complementary to a region of interest may be bioinformatically or computationally designed and/or chemically synthesized, e.g., by DNA synthesis. The nucleic acid sequences may be used as primers for nucleic acid amplification or detection, to prime cDNA synthesis from an RNA template, for sequencing, in primer extension reactions, for DNA/RNA hybridization, and/or DNA/RNA pull-down.

An antibiotic resistance marker may include one or more mutations, single nucleotide polymorphisms, genes, or gene products which confer antibiotic resistance. An antibiotic resistance marker may confer antibiotic resistance through one or more mechanisms such as, but not limited to, antibiotic efflux, antibiotic inactivation, antibiotic target alteration, antibiotic target protection, antibiotic target replacement, and/or reduced permeability to antibiotic. In some cases, an antibiotic resistance marker may be found in *Clostridium difficile* (*C. difficile*), carbapenem-resistant *Enterobacteriaceae* (CRE), drug-resistant *Neisseria*, gonorrhoeae (cephalosporin resistance), multidrug-resistant *Acinetobacter*, drug-resistant *Campylobacter*, fluconazole-resistant *Candida* (a fungus), extended spectrum β-lactamase producing *Enterobacteriaceae* (ESBLs), vancomycin-resistant *Enterococcus* (VRE), multidrug-resistant *Pseudomonas aeruginosa*, drug-resistant non-typhoidal *Salmonella*, drug-resistant *Salmonella Typhi*, drug-resistant *Shigella*, methicillin-resistant *Staphylococcus aureus* (MRSA), drug-resistant *Streptococcus pneumonia*, drug-resistant tuberculosis (MDR and XDR), multi-drug resistant *Staphylococcus aureus*, vancomycin-resistant *Staphylococcus aureus* (VRSA), erythromycin-resistant *Streptococcus* Group A, or clindamycin-resistant *Streptococcus* Group B. In some cases, an antibiotic resistance marker may confer antibiotic resistance to an acridine dye, aminocoumarin antibiotic, aminoglycoside, aminonucleoside antibiotic, beta-lactam, di aminopyrimidine, elfamycin, fluoroquinolone, glycopeptide antibiotic, lincosamide, lipopeptide antibiotic, macrocyclic antibiotic, macrolide, nucleoside antibiotic, organoarsenic antibiotic, oxazolidinone antibiotic, peptide antibiotic, phenicol, pleuromutilin antibiotic, polyamine antibiotic, rifamycin antibiotic, streptogramin antibiotic, sulfonamide, sulfone, tetracycline derivative, or any combination thereof. In some cases, an antibiotic resistance marker may confer antibiotic resistance to a β-lactam, penicillin, aminopenicillin, early generation cephalosporin, β-lactamase inhibitor combination, extended-spectrum cephalosporin, carbapenem, fluoroquinolone, aminoglycoside, tetracycline, glycycline, polymyxin, penicillin, methicillin, erythromycin, gentamicin, ceftazidime, vancomycin, levofloxacin, imipenem, linezolid, ceftriaxone, ceftaroline, or any combination thereof.

Non-limiting examples of antibiotic resistance markers include aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_bl2a_kcc, bl2a_nps, bl2a_okp, bl2a_pc, bl2be_ctxm, bl2be_oxy1, bl2be_per, bl2be_shv2, bl2b_rob, bl2b_tem1, bl2b_tem2, bl2b_tem, bl2b_tle, bl2b_ula, bl2c_bro, bl2c_pse1, bl2c_pse3, bl2d_1cr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_sme1, bl2_ges, bl2_kpc, bl2_len, bl2_veb, bl3_ccra, bl3_cit, bl3_cpha, bl3_gim, bl3_imp, bl3_1, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cm1_e1, cm1_e2, cm1e3, cm1_e4, cm1_e5, cm1_e6, cm1_e7, cm1_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdtl, mdtm, mdtn, mdto, mdtp, meca, mecr1, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, tetx, tety, tetz, tlrc, tmrb, tolc, tsnr, vana, vanb, vane, vand, vane, yang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd.

Enrichment

A method described herein may enrich population of interest nucleic acids. In some cases, population of interest nucleic acids may be enriched by about 5%; 10%; 15%; 20%; 25%; 30%; 35%; 40%; 45%; 50%; 55%; 60%; 65%; 70%; 75%; 80%; 85%; 90%; 95%; 100%; 150%; 200%; 250%; 300%; 350%; 400%; 450%; 500%; 550%; 600%; 650%; 700%; 750%; 800%; 850%; 900%; 950%; 1,000%; 2,000%; 3,000%; 4,000%; 5,000%; 6,000%; 7,000%; 8,000%; 9,000%; 10,000%; 20,000%; 30,000%; 40,000%; 50,000%; 60,000%; 70,000%; 80,000%; 90,000%; 100,000%; 200,000%; 300,000%; 400,000%; 500,000%; 600,000%; 700,000%; 800,000%; 900,000%; 1,000,000%; 2,000,000%; 3,000,000%; 4,000,000%; 5,000,000%; 6,000,000%; 7,000,000%; 8,000,000%; 9,000,000%; 10,000,000%; 20,000,000%; 30,000,000%; 40,000,000%; 50,000,000%; 60,000,000%; 70,000,000%; 80,000,000%; 90,000,000%; or 100,000,000%. In some cases, population of interest nucleic acids may be enriched by up to 5%; 10%; 15%; 20%; 25%; 30%; 35%; 40%; 45%; 50%; 55%; 60%; 65%; 70%; 75%; 80%; 85%; 90%; 95%; 100%; 150%; 200%; 250%; 300%; 350%; 400%; 450%; 500%; 550%; 600%; 650%; 700%; 750%; 800%; 850%; 900%; 950%; 1,000%; 2,000%; 3,000%; 4,000%; 5,000%; 6,000%; 7,000%; 8,000%; 9,000%; 10,000%; 20,000%; 30,000%;

40,000%; 50,000%; 60,000%; 70,000%; 80,000%; 90,000%; 100,000%; 200,000%; 300,000%; 400,000%; 500,000%; 600,000%; 700,000%; 800,000%; 900,000%; 1,000,000%; 2,000,000%; 3,000,000%; 4,000,000%; 5,000,000%; 6,000,000%; 7,000,000%; 8,000,000%; 9,000,000%; 10,000,000%; 20,000,000%; 30,000,000%; 40,000,000%; 50,000,000%; 60,000,000%; 70,000,000%; 80,000,000%; 90,000,000%; or 100,000,000%. In some cases, population of interest nucleic acids may be enriched by at least 5%; 10%; 15%; 20%; 25%; 30%; 35%; 40%; 45%; 50%; 55%; 60%; 65%; 70%; 75%; 80%; 85%; 90%; 95%; 100%; 150%; 200%; 250%; 300%; 350%; 400%; 450%; 500%; 550%; 600%; 650%; 700%; 750%; 800%; 850%; 900%; 950%; 1,000%; 2,000%; 3,000%; 4,000%; 5,000%; 6,000%; 7,000%; 8,000%; 9,000%; 10,000%; 20,000%; 30,000%; 40,000%; 50,000%; 60,000%; 70,000%; 80,000%; 90,000%; 100,000%; 200,000%; 300,000%; 400,000%; 500,000%; 600,000%; 700,000%; 800,000%; 900,000%; 1,000,000%; 2,000,000%; 3,000,000%; 4,000,000%; 5,000,000%; 6,000,000%; 7,000,000%; 8,000,000%; 9,000,000%; 10,000,000%; 20,000,000%; 30,000,000%; 40,000,000%; 50,000,000%; 60,000,000%; 70,000,000%; 80,000,000%; 90,000,000%; or 100,000,000%. For example, if a sample contains 5% population of interest nucleic acids out of the total population of nucleic acids and is enriched to contain 10% population of interest nucleic acids out of the total population of nucleic acids, the population of interest nucleic acids are enriched by 100%. In some cases, population of interest nucleic acids may be enriched by about 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold; 75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. In some cases, population of interest nucleic acids may be enriched by up to 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold; 75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. In some cases, population of interest nucleic acids may be enriched by at least 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold; 75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. For example, if a sample contains 5% population of interest nucleic acids out of the total population of nucleic acids and is enriched to contain 10% population of interest nucleic acids out of the total population of nucleic acids, the population of interest nucleic acids are enriched by 2-fold.

A method described herein may deplete background population nucleic acids. In some cases, background population nucleic acids may be depleted by about 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%. In some cases, background population nucleic acids may be depleted by up to 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%. In some cases, background population nucleic acids may be depleted by at least 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100%. For example, if a sample contains 50% background population nucleic acids out of the total population of nucleic acids and is depleted to contain 10% background population nucleic acids out of the total population of nucleic acids, the background population nucleic acids are depleted by 80%. In some cases, background population nucleic acids may be enriched by about 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold; 75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. In some cases, background population nucleic acids may be enriched by up to 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold; 75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. In some cases, background population nucleic acids may be enriched by at least 1.5-fold; 2-fold; 2.5-fold; 3-fold; 3.5-fold; 4-fold; 4.5-fold; 5-fold; 5.5-fold; 6-fold; 6.5-fold; 7-fold; 7.5-fold; 8-fold; 8.5-fold; 9-fold; 9.5-fold; 10-fold; 15-fold; 20-fold; 25-fold; 30-fold; 35-fold; 40-fold; 45-fold; 50-fold; 55-fold; 60-fold; 65-fold; 70-fold;

75-fold; 80-fold; 85-fold; 90-fold; 95-fold; 100-fold; 150-fold; 200-fold; 250-fold; 300-fold; 350-fold; 400-fold; 450-fold; 500-fold; 550-fold; 600-fold; 650-fold; 700-fold; 750-fold; 800-fold; 850-fold; 900-fold; 950-fold; 1,000-fold; 2,000-fold; 3,000-fold; 4,000-fold; 5,000-fold; 6,000-fold; 7,000-fold; 8,000-fold; 9,000-fold; 10,000-fold; 20,000-fold; 30,000-fold; 40,000-fold; 50,000-fold; 60,000-fold; 70,000-fold; 80,000-fold; 90,000-fold; 100,000-fold; 200,000-fold; 300,000-fold; 400,000-fold; 500,000-fold; 600,000-fold; 700,000-fold; 800,000-fold; 900,000-fold; or 1,000,000-fold. For example, if a sample contains 50% background population nucleic acids out of the total population of nucleic acids and is depleted to contain 10% background population nucleic acids out of the total population of nucleic acids, the background population nucleic acids are depleted by 5-fold.

Samples

The methods and compositions provided herein are useful for detecting nucleic acids in a wide variety of samples obtained from a subject (e.g., a human host). Some non-limiting examples of a biological sample include blood, plasma, serum, whole blood, mucus, saliva, cerebrospinal fluid, synovial fluid, lavage, urine, tissue biopsies, cellular samples, skin samples, and stool. The sample may comprise nucleic acids such as circulating nucleic acids including circulating cell-free nucleic acids (e.g., circulating cell-free DNA, circulating cell-free RNA). In some cases, a sample obtained from a subject undergoes further processing. For example, the sample may be processed to extract DNA or RNA, which may be analyzed using a method provided herein.

In some cases, a sample of nucleic acids may be a sample such as a biological sample, an isolated nucleic acid sample, or a purified nucleic acid sample that contains nucleic acids such as circulating nucleic acids. In some cases, a sample of nucleic acids may contain host and non-host sequences, for example, human and non-human sequences. In some cases, nucleic acids in a sample of nucleic acids are amplified (e.g., by a PCR amplification reaction) such as a sequencing-ready library of nucleic acids. In some cases, nucleic acids in a sample of nucleic acids are not artificially fragmented (e.g., by sonication, shearing, enzymatic digestion, or chemical fragmentation). In some cases, nucleic acid fragmentation is unnecessary as the nucleic acids are relatively short in length. In some cases, nucleic acids in a sample of nucleic acids are artificially fragmented. A sample of circulating nucleic acids may be a sample such as a biological sample, an isolated nucleic acid sample, or a purified nucleic acid sample that contains circulating nucleic acids such as circulating cell-free nucleic acids. In some cases, a sample of circulating cell-free nucleic acids may be a sample such as a biological sample, an isolated nucleic acid sample, or a purified nucleic acid sample that contains circulating cell-free nucleic acids such as circulating cell-free DNA or circulating cell-free RNA. In some cases, a sample of single-stranded nucleic acids may be a sample such as a biological sample, an isolated nucleic acid sample, or a purified nucleic acid sample that contains single-stranded nucleic acids such as single-stranded circulating nucleic acids or single-stranded circulating cell-free nucleic acids.

In some cases, nucleic acids may be DNA, RNA, cDNA, mRNA, cRNA, dsDNA, ssDNA, miRNA, circulating nucleic acids, circulating DNA, circulating RNA, cell-free nucleic acids, cell-free DNA, cell-free RNA, circulating cell-free DNA, circulating cell-free RNA, or genomic DNA. In some cases, circulating nucleic acids are circulating DNA, circulating RNA, cell-free nucleic acids, or circulating cell-free nucleic acids. In some cases, cell-free nucleic acids may be cell-free DNA, cell-free RNA, circulating cell-free DNA, or circulating cell-free RNA. In some cases, circulating cell-free nucleic acids may be circulating cell-free DNA or circulating cell-free RNA.

In some cases, nucleic acids within the sample may be unlabeled; in some cases, nucleic acids are labeled, e.g., with a nucleic acid label, a chemical label, or an optical label. In some cases, nucleic acids are conjugated to a solid support. In some cases, a label may be attached at the 5' or 3' end of a nucleic acid or internally within a nucleic acid. In some cases, nucleic acids are labeled with more than one label.

Nucleic acids in a sample may be tagged with a nucleic acid label. In some cases, a nucleic acid label may comprise one or more of the following: barcode (e.g., sample barcode), universal primer sequence, primer binding site (e.g., for sequencing or to read a barcode, including, but not limited to, DNA sequencing primer binding site, sample barcode sequencing primer binding site, and amplification primer binding site compatible with various sequencing platform requirements), sequencer-compatible sequence, sequence to attach to a sequencing platform, sequencing adapter sequence, or adapter. Nucleic acid labels may be attached to the nucleic acid (e.g., by ligation, or by synthetic design).

A nucleic acid label may comprise a chemical label. Some non-limiting examples of a chemical label include biotin, avidin, streptavidin, radiolabel, polypeptide, and polymers. A nucleic acid label may comprise an optical label. Some non-limiting examples of an optical label include a fluorophore, fluorescent protein, dye, and quantum dot. A nucleic acid label may be conjugated to a solid support. Some non-limiting examples of a solid support include a bead, magnetic bead, polymer, slide, chip, surface, plate, channel, cartridge, microfluidic device, and microarray. A nucleic acid may be conjugated to a solid support for affinity chromatography. In some cases, each nucleic acid has a different label. In some cases, each nucleic acid has the same label. In some cases, the nucleic acids in the sample are not conjugated to a solid support.

Sequencing Methods

In some cases, the enriched population of nucleic acids is sequenced. In some cases, a method described herein further comprises performing a sequencing assay. The amplified or captured population of interest nucleic acids may be identified by any method known in the art such as by conducting a sequencing assay, particularly a high-throughput sequencing assay, a Next Generation sequencing platform, a massively parallel sequencing platform, a Nanopore sequencing assay, Sanger sequencing, or another sequencing assay known in the art. Some non-limiting examples of a sequencing assay include a high-throughput sequencing assay, a Next Generation sequencing platform, a massively parallel sequencing platform, Nanopore sequencing, and Sanger sequencing. Some non-limiting examples of types of sequencing machines include Illumina, Roche 454, Ion Torrent, and Nanopore.

The process methods described herein may also be used in conjunction with other methods for differentiating between host nucleic acid sequences and non-host nucleic acid sequences, including, for example, informatics data sorting methods applied to resultant sequence data, that may distinguish between host and non-host sequences. Examples of such processes include, e.g., those described in published U.S. Patent Application No. 2015-0133391, the full disclosure of which is hereby incorporated herein by reference in its entirety for all purposes.

Applications

The methods and compositions are useful for analyzing biological samples from hosts infected with one or more non-host species (e.g., microbes, pathogens, bacteria, viruses, fungi, or parasites).The methods and compositions provided herein are particularly useful for detecting, predicting, diagnosing, or monitoring a disease or disorder, particularly a disease or disorder caused by a microbe or pathogen. The methods and compositions provided herein are also useful for detecting a population-of-interest in certain types of samples obtained from an infected host, such as samples comprising circulating cell-free DNA or circulating cell-free RNA.

The methods and compositions may also be used to enable genotyping of pathogens in a sample. The methods and compositions are also particularly useful for detecting alterations in microbial or pathogen genomes. For example, they may be used to detect antibiotic resistant strains of bacteria or to track alterations affecting virulence of pathogens, particularly viruses and bacteria.

In other cases, the methods and compositions may be used to monitor the presence of one or more microbes, e.g., in the microbiome. For example, the methods and compositions may be used to monitor the presence of the microbiome in a healthy or non-infected host. The methods and compositions can be also used to monitor microbial signatures within a sample containing multiple microbes.

The methods and compositions provided herein may also enable hypothesis-free detection of nucleic acids derived from one or more non-host organisms (e.g., microbe, pathogen, bacteria, virus, fungus, or parasite) or hypothesis-free diagnosis or monitoring of a disease, disorder, or infection. As such, the methods provided herein may be unlike other diagnostic methods that screen for specific targets (e.g., one or more specific nucleic acid sequences, proteins, or antibodies) and are limited to testing for the chosen targets. In some cases, the hypothesis-free characteristic of the methods and compositions provided herein may facilitate detecting rare infections, detecting the co-incidence of two or more diseases or disorders, identifying the source of an infection, or distinguishing among multiple diseases or disorders with similar or generic symptoms.

In some specific examples, the method may comprise one or more of the following steps in any order or combination: (a) providing a nucleic acid sample from a subject or patient having or suspected of having a pathogenic infection; (b) contacting the nucleic acid sample with a collection of oligonucleotides provided herein, particularly a collection of oligonucleotides selectively enriched to bind to non-host sequences; (c) subjecting the sample and collection of oligonucleotides to conditions to facilitate hybridization of the collection of oligonucleotides with nucleic acid molecules within the nucleic acid sample; (d) conducting an assay such as an amplification assay, pull-down assay, or a sequencing assay on the nucleic acids hybridized to the collection of oligonucleotides; and (e) analyzing the sequences of the hybridized nucleic acids in order to detect specific pathogens in the sample. Often, the number of specific pathogens detected is quite large, as described further herein, such as on the order of greater than 10, 20, 30, 40, 50 or more different pathogens. Often the detection of the pathogens can enable detection, prognosis, monitoring or diagnosis of an infectious disease, an infectious disorder, an infection, or other disease or disorder (e.g., cancer). In some cases, such detection can facilitate staging of a disease or disorder, or provide an indication of degree of pathogenic infection.

In some cases, a method described herein further comprises detecting at least one population of interest sequence (e.g., pathogenic or other non-host or non-human sequence). In some cases, a method described herein further comprises detecting at least five populations of interest sequences. In some cases, a method described herein further comprises detecting at least five non-mammalian sequences. In some cases, a method described herein further comprises detecting at least one non-mammalian sequence from each of at least five non-mammalian species. In some cases, a method described herein further comprises detecting at least five non-human sequences. In some cases, a method described herein further comprises detecting at least one non-human sequence from each of at least five non-human species. In some cases, a method described herein further comprises detecting at least one bacterial sequence and at least one viral sequence. In some cases, a method described herein further comprises taking more than one time point, e.g., 2, 3, 4, 5, 6, 7, 8, 10, 11, 12, 13, 14, 15, 16, 17, 18, 19, 20, 25, 30, 35, 40, 45, 50, 55, 60, 65, 70, 75, 80, 85, 90, 95, or 100 time points. In some cases, a method described herein further comprises taking time points before and after a treatment, e.g., an antimicrobial drug.

In some cases, a method described herein further comprises detecting at least one nucleic acid derived from about 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, a method described herein further comprises detecting at least one nucleic acid derived from up to 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, a method described herein further comprises detecting at least one nucleic acid derived from at least 1; 2; 3; 4; 5; 6; 7; 8; 9; 10; 15; 20; 25; 30; 35; 40; 45; 50; 60; 70; 80; 90; 100; 200; 300; 400; 500; 1,000; 5,000; 10,000; 50,000; or 100,000 species. In some cases, the species is a non-host species. In some cases, the species is a non-mammalian species. In some cases, the species is a non-human species. In some cases, the species is a microbe, bacteria, virus, fungus, retrovirus, pathogen, or parasite. In some cases, a method described herein further comprises detecting at least one nucleic acid derived from about 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, a method described herein further comprises detecting at least one nucleic acid derived from up to 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, a method described herein further comprises detecting at least one nucleic acid derived from at least 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial or viral species. In some cases, a method described herein further comprises detecting at least one nucleic acid derived from about 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, a method described herein further comprises detecting at least one nucleic acid derived from up to 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, a method described herein further comprises detecting at least one nucleic acid derived from at least 1, 2, 3, 4, 5, 6, 7, 8, 9, 10, 15, 20, 25, 30, 35, 40, 45, 50, 60, 70, 80, 90, 100, 200, 300, 400, 500, or 1,000 bacterial and viral species. In some cases, a method described herein further comprises detecting at least one nucleic acid derived from about 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species. In some cases, a method described herein further comprises detecting at least one nucleic acid derived from up to 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species. In some cases, a method described herein further comprises detecting at least one nucleic acid derived from at least 1 bacterial and 1 viral species, 2 bacterial and 2 viral species, 3 bacterial and 3 viral species, 4 bacterial and 4 viral species, 5 bacterial and 5 viral species, 6 bacterial and 6 viral species, 7 bacterial and 7 viral species, 8 bacterial and 8 viral species, 9 bacterial and 9 viral species, 10 bacterial and 10 viral species, 15 bacterial and 15 viral species, 20 bacterial and 20 viral species, 25 bacterial and 25 viral species, 30 bacterial and 30 viral species, 35 bacterial and 35 viral species, 40 bacterial and 40 viral species, 45 bacterial and 45 viral species, 50 bacterial and 50 viral species, 60 bacterial and 60 viral species, 70 bacterial and 70 viral species, 80 bacterial and 80 viral species, 90 bacterial and 90 viral species, 100 bacterial and 100 viral species, 200 bacterial and 200 viral species, 300 bacterial and 300 viral species, 400 bacterial and 400 viral species, 500 bacterial and 500 viral species, or 1,000 bacterial and 1,000 viral species.

In some cases, a method described herein comprises determining if an infection is active or latent. In some cases, gene expression quantification may provide a method for detecting, predicting, diagnosing, or monitoring an active infection. In some cases, a method described herein comprises detecting an active infection. In some cases, gene expression may be quantified through detection or sequencing of a population of interest. In some cases, gene expression quantification may provide a method for detecting, predicting, diagnosing, or monitoring a latent infection. In some cases, a method described herein comprises detecting a latent infection.

Exemplary diseases and disorders include any disease or disorder associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *Staphylococcus aureus* infection, or influenza. The methods provided herein are particularly useful for detecting infections by drug-resistant microbes, including multi-drug resistant microbes. Some non-limiting examples of diseases and disorders include Alzheimer's disease, amyotrophic lateral sclerosis, anorexia nervosa, anxiety disorder, asthma, atherosclerosis, attention deficit hyperactivity disorder, autism, autoimmune disease, bipolar disorder, cancer, chronic fatigue syndrome, chronic obstructive pulmonary disease, Crohn's disease, coronary heart disease, dementia, depression, diabetes mellitus type 1, diabetes mellitus type 2, dilated cardiomyopathy, epilepsy, Guillain-Barre syndrome, irritable bowel syndrome, low back pain, lupus, metabolic syndrome, multiple sclerosis, myocardial infarction, obesity, obsessive-compulsive disorder, panic disorder, Parkinson's disease, psoriasis, rheumatoid arthritis, sarcoidosis, schizophrenia, stroke, thromboangiitis obliterans, Tourette syndrome, vasculitis, plague, tuberculosis, anthrax, sleeping sickness, dysentery, toxoplasmosis, ringworm, candidiasis, histoplasmosis, ebola, *Acinetobacter* infections, Actinomycosis, African sleeping sickness (African trypanosomiasis), AIDS (Acquired immunodeficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, *Black piedra*, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (*Norovirus* and *Sapovirus*), Campylobacteriosis, Candidiasis (*Moniliasis*; *Thrush*), Cat-scratch disease, *Cellulitis*, Chagas Disease (*American trypanosomiasis*), Chancroid, Chickenpox, Chikungunya, *Chlamydia*, *Chlamydophila pneumoniae* infection (Taiwan acute respiratory agent or TWAR), *Cholera*, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), *Cryptococcosis*, *Cryptosporidiosis*, Cutaneous larva migrans (CLM), *Cyclosporiasis*, *Cysticercosis*, *Cytomegalovirus* infection, Dengue fever, *Dientamoebiasis*, Diphtheria, Diphyllobothriasis, Dracunculiasis, Ebola hemorrhagic fever, Echinococcosis, Ehrlichiosis, Enterobiasis (Pinworm infection), *Enterococcus* infection, *Enterovirus* infection, Epidemic typhus, Erythema infectiosum (Fifth disease), *Exanthem subitum* (Sixth disease), Fasciolopsiasis, Fasciolosis, Fatal familial insomnia (FFI), Filariasis, Food poisoning by *Clostridium perfringens*, Free-living amebic infection, Fusobacterium infection, *Gas gangrene* (*Clostridial myonecrosis*), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), *Hantavirus Pulmonary Syndrome* (HPS), *Heartland virus disease*, *Helicobacter pylori* infection, Hemolytic-uremic syndrome (HUS), Hemorrhagic fever with renal syndrome (HFRS), *Hepatitis A*, *Hepatitis B*, *Hepatitis C*, *Hepatitis D*, *Hepatitis E*, *Herpes simplex*, Histoplasmosis, Hookworm infection, Human bocavirus infection, Human ewingii ehrlichiosis, Human granulocytic anaplasmosis (HGA), *Human metapneumovirus infection, Human monocytic ehrlichiosis, Human papillomavirus* (HPV) *infection, Human parainfluenza virus infection, Hymenolepiasis, Epstein-Barr Virus Infectious Mononucleosis* (Mono), *Influenza* (flu), *Isosporiasis, Kawasaki disease, Keratitis, Kingella kingae infection, Kuru, Lassa fever, Legionellosis* (Legionnaires' disease), *Legionellosis* (Pontiac fever), *Leishmaniasis, Leprosy, Leptospirosis, Listeriosis, Lyme disease* (Lyme borreliosis), *Lymphatic filariasis* (Elephantiasis), *Lymphocytic choriomeningitis, Malaria, Marburg hemorrhagic fever* (MHF), *Measles,* Middle East respiratory syndrome (MERS), *Melioidosis* (Whitmore's disease), *Meningitis, Meningococcal disease, Metagonimiasis, Microsporidiosis, Molluscum contagiosum* (MC), *Monkeypox, Mumps, Murine typhus* (Endemic typhus), *Mycoplasma pneumonia, Mycetoma, Myiasis, Neonatal conjunctivitis* (Ophthalmia neonatorum), (New) *Variant Creutzfeldt-Jakob disease* (vCJD, nvCJD), *Nocardiosis, Onchocerciasis* (River blindness), *Paracoccidioidomycosis* (South American blastomycosis), *Paragonimiasis, Pasteurellosis, Pediculosis capitis* (Head lice), *Pediculosis corporis* (Body lice), *Pediculosis pubis* (Pubic lice, Crab lice), *Pelvic inflammatory disease* (PID), *Pertussis* (Whooping cough), *Plague, Pneumococcal infection, Pneumocystis pneumonia* (PCP), *Pneumonia, Poliomyelitis, Prevotella infection, Primary amoebic meningoencephalitis* (PAM), *Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever* (RVF), *Rocky Mountain spotted fever* (RMSF), *Rotavirus infection, Rubella, Salmonellosis, SARS* (Severe Acute Respiratory Syndrome), *Scabies, Schistosomiasis, Sepsis, Shigellosis* (Bacillary dysentery), *Shingles* (Herpes zoster), *Smallpox* (Variola), *Sporotrichosis, Staphylococcal food poisoning, Staphylococcal infection, Strongyloidiasis, Subacute sclerosing panencephalitis, Syphilis, Taeniasis, Tetanus* (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (Pityriasis versicolor), *Toxocariasis* (Ocular Larva Migrans (OLM)), *Toxocariasis* (Visceral Larva Migrans (VLM)), *Trachoma, Trinochccliasis, Trichinlosis, Trichomoniasis, Trichuriasis* (Whipworm infection), *Tuberculosis, Tularemia, Typhoid Fever, Ureaplasma urealyticum infection, Valley fever, Venezuelan equine encephalitis, Venezuelan hemorrhagic fever, Viral pneumonia, West Nile Fever, White piedra* (Tinea blanca), *Yersinia pseudotuberculosis infection, Yersiniosis, Yellow fever,* and *Zygomycosis.*

As used herein, the term "or" is used to refer to a nonexclusive or, such as "A or B" includes "A but not B," "B but not A," and "A and B," unless otherwise indicated.

As used herein, the term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

EXAMPLES

Example 1

Preparation of Cell-Free RNA from Patient Whole Blood Sample

Whole blood is drawn from a patient suspected of having an infectious disease and placed in an acid citrate dextrose (ACD) blood collection tube. A portion (1.5 mL) of the blood in the ACD collection tube is removed and placed into a 1.5 mL microfuge tube. The blood is spiked with 10 µL of normalization oligonucleotides and mixed well. The mixture is centrifuged at 1,600 g for 10 min at 4° C., and 550 µL of supernatant ("normalized plasma") is removed and placed into a fresh microfuge tube. The normalized plasma is centrifuged at 16,000 g for 10 min at 4° C. The supernatant ("normalized cell-free plasma") is removed and placed into a fresh tube and stored at −80° C.

The normalized cell-free plasma is thawed at room temperature for 10 min. The normalized cell-free plasma is centrifuged at 16,000 g for 10 min at 4° C. to remove debris. Cell-free RNA is isolated using the Plasma/Serum Circulating and Exosomal RNA Purification Kit (Slurry Format) (Norgen Biotek Corp.) according to the manufacturer's instructions. Cell-free RNA is stored at −80° C.

Example 2

Preparation of a Non-Human Collection of Oligonucleotides by Computational Design and Synthesis Approximately $6.7 \times 10^6$ possible different domains of nucleotides have a length of 13 nucleotides. From this theoretical pool of sequences, any 13 nucleotide sequence found in human DNA is discarded, leaving approximately $2.3 \times 10^6$ unique 13 nucleotide sequences, or 3.5% of the total. From these $2.3 \times 10^6$ non-human 13 nucleotide sequences, approximately $1 \times 10^6$ are selected for inclusion in the non-human sequence pool on the basis of the following criteria, 1) melting temperature uniformity, 2) sufficient sequence complexity, 3) abundance of binding sites in known pathogens, 4) and binding site distribution among known pathogens. To this set of approximately $1 \times 10^6$ non-human 13 nucleotide sequences, additional non-human sequences of 14-20 nucleotides in length are added to enhance the coverage of regions of interest such as strategic pathogen sequences, and these primers are designed on the basis of 1) melting temperature, 2) sequence complexity, 3) abundance of binding sites in known pathogens, and 4) binding site distribution among known pathogens. The total pool of domains of nucleotides of 13-20 nucleotides in length is referred to as the full non-human sequence pool. To each 13-20 nucleotide sequence in the non-human sequence pool, an additional 5' sequence of approximately 15-25 nucleotides in length containing one or more of the following nucleic acid labels is added: 1) DNA sequencing primer binding site, 2) Sample barcode, 3) Sample barcode sequencing primer binding site, and 4) Amplification primer binding site compatible with various sequencing platform requirements. This collection of oligonucleotides is referred to as the non-human primer pool. The non-human primer pool is chemically synthesized. Alternatively, the full non-human sequence pool is chemically synthesized and the one or more nucleic acid labels are added (e.g., by ligation) to form the non-human primer pool.

Example 3

Preparation of Non-Human Collection of Oligonucleotides Using a Hybridization-Based Method The approximately 67 million different 13 nucleotide sequences (e.g., 5'-NNNNNNNNNNNNN-3', where N is A, C, G, or T) are chemically synthesized with an attached 15-25 nucleotide overhang containing one or more of the following nucleic acid labels: 1) DNA sequencing primer binding site, 2) sample barcode, 3) sample barcode sequencing primer binding site, and 4) amplification primer binding site compatible with various sequencing platform requirements. This heterogeneous collection of oligonucleotides is hybridized to 1,000-fold by mass excess biotinylated human single-stranded genomic DNA (gDNA) fragments in Hybridization buffer (0.5×PBS, 24 µM blocker oligonucleotide, RNase inhibitor) at 95° C. for 10 seconds, at 65° C. for 3 min, and at 36° C. for a defined amount of time on the order of hours to several weeks. At the end of the incubation period, human gDNA fragments, along with probes that have hybridized to the fragments, are removed by streptavidin beads. The remaining pool of probes that did not bind human gDNA under these conditions is supplemented with additional non-human sequences of 14-20 nucleotides in length to enhance the coverage of regions of interest such as strategic pathogen sequences, and these primers are designed on the basis of 1) melting temperature, 2) sequence complexity, 3) abundance of binding sites in known pathogens, and 4) binding site distribution among known pathogens. The collection of oligonucleotides is referred to as the non-human primer pool.

Example 4

Preparation of Non-Human Collection of Oligonucleotides with High Degeneracy in High Yields Non-human 13-mers are computationally determined by generating all possible 13-mer sequences and removing those that appear in a reference human genome. The non-human 13-mers are then grouped by degree of degeneracy. The histogram in FIG. 11B shows bucketing of non-human 13-mers based on degree of degeneracy.

Next, variable oligonucleotide sequence units of non-human 13-mers of the same degree of degeneracy are grouped into an ultramer oligonucleotide. The number of degenerate oligonucleotide sequence units included in an ultramer can be based on the length of each unit and the ultramer length that can be reliably synthesized. FIG. 9 shows the general design of several such ultramer oligonucleotides. Individual degenerate 13-mers may be separated by a deoxyuracil nucleotide (U). The designed ultramer oligonucleotide may then be synthesized by conventional nucleic acid synthesis processes and service providers, e.g., IDT.

The ultramer oligonucleotides may then be digested by Uracil-DNA Glycosylase (UDG) and endonucleases with specificity at abasic sites (e.g., apurinic/apyrimidinic site or AP site), into individual degenerate non-human 13-mer oligonucleotides. This digestion may be carried out in the same tube for all ultramer oligonucleotides carrying the degenerate 13-mers with the same degree of degeneracy. An exemplary reaction is described in FIG. 10.

Individual degenerate 13-mers may then be biotinylated, e.g., using T4 Polynucleotide Kinase (T4 PNK) or chemically as shown in FIG. 12. This step is optional, for example, if surface immobilization or magnetic bead purification is required. Other probes than biotin can be applied here (e.g., digoxigenin, fluorescent probes, etc.).

Example 5

Preparation of an Enriched Sequencing Library Using a Non-Human Collection of Oligonucleotides Cell-free RNA from Example 1 is hybridized with non-human primer pool (prepared as described in Example 2 or 3) in Hybridization buffer (0.5×PBS, 24 µM blocker oligonucleotide, RNase inhibitor) at 95° C. for 10 seconds, at 65° C. for 3 min, and at 36° C. overnight. First strand cDNA synthesis master mix (reverse transcriptase enzyme, blocked $2^{nd}$ strand synthesis oligonucleotide, dNTPs, RNase inhibitor, and appropriate buffers) is added at 36° C., after which the temperature is increased to 42° C. for 90 minutes to allow $1^{st}$ strand cDNA synthesis. The mixture is then incubated at 70° C. for 10 minutes to inactivate the reverse transcriptase, and held at 4° C.

The first strand cDNA product is purified using a commercial kit. Second-strand cDNA is generated by PCR using primers that hybridize to fixed sequences added to the 5' and 3' ends of the $1^{st}$ strand cDNA during the previous step. Following the second strand synthesis by PCR, one or more of the following nucleic acid labels may be added by an additional round of PCR: 1) DNA sequencing primer binding site, 2) sample barcode, 3) sample barcode sequencing primer binding site, and 4) amplification primer binding site compatible with various sequencing platform requirements. The final cDNA library is purified with a commercially available kit according to the manufacturer's instructions.

Example 6

Preparation of a Sequencing Library Enriched for Non-Human Sequences from a DNA or cDNA Library Using a Non-Human Collection of Oligonucleotides A sequencing-ready library is prepared. A non-human primer pool is prepared as described in Example 2 or 3 and subjected to conditions to promote 5' biotinylation of the individual oligonucleotides in the pool. Then, 1 pmol of 5'-biotinylated non-human primer pool is added to 500 ng of sequencing-ready library in hybridization/polymerization buffer (buffers, nucleotides, blocker oligonucleotide). In some cases, pre incubation of the oligonucleotides with molecules that enhance the speed or specificity of DNA hybridization reactions may improve the capture of non-host nucleic acid fragments, such as RecA or MutS. DNA is denatured at 95° C. for 10 min. Non-human primers are hybridized to the sequencing library at 50° C. for 4 hours. A strand-displacing DNA polymerase that lacks a 5' exonuclease is added to the mixture. The mixture is incubated at 55° C. for 15 minutes to extend the non-human primer to at least 25 bases or a length sufficient for stable double-stranded DNA hybridization during subsequent steps. Streptavidin beads are added to the mixture to bind the DNA fragments. The captured DNA fragments on the beads are washed. The captured library DNA fragments are amplified using standard PCR amplification methods by using primers specific for the adapters at the ends of the DNA sequencing library fragments and the DNA fragments captured on the beads as the template. The enriched library is purified using standard DNA purification methods. The library is quantified with a KAPA DNA library quantification kit (KAPA Biosystems) and prepared for sequencing on the NextSeq 500 (Illumina) according to the manufacturer's instructions. Sequencing consists of single end reads of 150 cycles plus barcode reads of 8 cycles. Sequence reads are computationally mapped to genomes of pathogens to identify one or more sources of one or more nucleic acids.

Example 7

Human Nucleosome-Associated DNA Depletion Using Anti-Human Histone Antibodies and Anti-Immunoglobulin Antibodies Cell-free DNA is prepared by either a centrifugation-based method or by an albumin and immunoglobulin removal method. In either method, 1 mL of human plasma is first centrifuged at 1,600 g for 10 min at 4° C. For the centrifugation-based method, the supernatant (950 µL) is collected and transferred into a pure test tube and centrifuged again at 16,000 g for 10 min at 4° C. The 900 µL of supernatant, which contains cell-free DNA, is collected and transferred into a fresh test tube. In the albumin and immunoglobulin removal method, the supernatant (950 µL) from the first centrifugation is collected and run through human albumin- and human immunoglobulin-binding columns (e.g., Albumin and IgG Depletion SpinTrap from GE Healthcare, or Albumin/IgG Removal Kit from Life Technologies). The flow through, which contains cell-free DNA, is collected and transferred into a fresh test tube.

The cell-free DNA prepared by centrifugation or by albumin and immunoglobulin removal, as described above, is mixed with 5 µg of one or more anti-human histone antibodies and incubated from 1 hr to overnight at 4° C. with slow rotation. The antibodies bind to nucleosomes to form complexes. A mixture of magnetic beads conjugated to anti-immunoglobulin antibodies is added to the reaction to sequester the human nucleosome-antibody complexes from the plasma sample. The anti-immunoglobulin antibodies include a combination of antibodies necessary to bind the isotopes of the anti-human histone antibodies added in the previous step. The mixture is incubated for 1 hr at room temperature or 5 hr to overnight at 4° C. The magnetic beads with bound human nucleosome-antibody complexes are pelleted on a magnetic stand. The supernatant is collected carefully to not collect any remnants of the magnetic bead fraction. The obtained supernatant is purified using a commercially available kit (e.g., QIAamp Circulating Nucleic Acid Kit, Qiagen) to enrich the pathogen cell-free DNA.

Example 8

Human Nucleosome-Associated DNA Depletion Using Anti-Human Histone Antibodies and Magnetic Beads Conjugated to Protein a and/or G The flow through containing cell-free DNA prepared using the albumin and immunoglobulin removal method in Example 6 is mixed with 5 µg of one or more anti-human histone antibodies and incubated from 1 hr to overnight at 4° C. with slow rotation. The human nucleosome-antibody complexes are sequestered from the solution by adding magnetic beads conjugated to Protein A and/or G. The mixture is incubated for 1 hr at room temperature or 5 hr to overnight at 4° C. The magnetic beads with bound human nucleosome-antibody complexes are pelleted on a magnetic stand. The supernatant is collected carefully to not collect any remnants of the magnetic bead fraction. The obtained supernatant is purified using a commercially available kit (e.g., QIAamp Circulating Nucleic Acid Kit, Qiagen) to enrich the pathogen cell-free DNA.

Example 9

Human Nucleosome-Associated DNA Depletion Using Anti-Human Histone Antibodies and a Spin Column The flow through containing cell-free DNA prepared using the anti-albumin-immunoglobulin method in Example 6 is mixed with 5 µg of one or more anti-human histone antibodies and incubated from 1 hr to overnight at 4° C. with slow rotation. The nucleosome-antibody complexes are purified away by running the solution through a spin column functionalized with Protein A/G or anti-immunoglobulin antibodies. The flow through is collected and is purified using a commercially available kit (e.g., QIAamp Circulating Nucleic Acid Kit, Qiagen) to enrich the pathogen cell-free DNA.

Example 10

Human Nucleosome-Associated DNA Depletion by DNA Precipitation

Nucleosome-free cell-free DNA and nucleosome-bound cell-free DNA are precipitated after plasma centrifugation using DNA condensing agents (e.g., spermine). The precipitate is collected by centrifugation, and the supernatant is discarded. The pellet is dissolved in a buffer optimized for anti-human histone antibody binding to human nucleosome. The resulting antigen-antibody complex is sequestered by binding it to magnetic beads conjugated to either Protein A/G or anti-immunoglobulin antibodies, pelleting the magnetic beads on a magnet stand, and collecting the supernatant. The obtained supernatant is purified using a commercially available kit (e.g., QIAamp Circulating Nucleic Acid Kit, Qiagen) to enrich pathogen cell-free DNA.

Example 11

Optimization of Nucleotide Length for a Domain of Nucleotides in a Non-Human Collection of Oligonucleotides Several parameters are optimized when choosing the length of the domain of nucleotides in the non-human primer pool. The goal is to produce a pool with the smallest number of different sequences that provide the maximum sensitivity to detect non-human nucleic acids. As the length of the domain of nucleotides increases, a greater number of different probes is required to cover the sequence space, since a domain of nucleotides with length of k has $4^k$ permutations. The number of probes in the pool is kept as small as possible so that each individual sequence is present at a higher concentration, facilitating faster hybridization kinetics. This consideration favors shorter primers. At the same time, as the length of the primer increases, a smaller fraction of the total possible sequences of that length will bind human sequences. That means a higher fraction of the total genomic space will be left in the pool of non-human primers, which results in higher coverage of the non-human sequences and provides greater sensitivity. For example, only 3.5% (2.3 million) of the possible sequences 13 nucleotides in length are not found in the human reference genome, which means the pool of non-human sequences 13 nucleotides in length will bind to only 3.5% of all possible 13 nucleotide stretches in non-human nucleic acid. In contrast, 15.2% (40.7 million) of the possible sequences 14 nucleotides in length are not found in the human reference genome. 15.2% of all possible 14 nucleotide stretches in non-human nucleic acid could be theoretically detected. 40.7 million probes may be too many to reasonably synthesize using certain existing vendors. If each probe is present at 1/40.7 millionth of the total probe concentration, the concentration of any individual probe may be too low to favorably bind its complementary sequence at equilibrium unless other measures to facilitate hybridization are taken. That observation may rule out a probe set longer than 13 nucleotides in length. Alternatively, sequences shorter than 13 nucleotides in length are found so frequently in the human reference genome that nearly all primers are removed from the non-human pool. For example, at 12 nucleotides in length, 99.74% of the possible sequences are found in the human reference genome. That means the pool of non-human primers would only bind 0.26% or so of the possible 12 nucleotide sequences in pathogens and would provide limited sensitivity. A domain of nucleotides with 13 nucleotides in length provides adequate sensitivity (approximately 1 binding site every 30 nucleotides in non-human genomes), with few enough probes to have reasonable kinetics in hybridization reactions (less than 10 million different probes).

Example 12

Selective Enrichment of Short Fragments in Cell-Free DNA

Size enrichment protocols were optimized for the selection of cell-free DNA having relatively short fragment lengths. Cell-free DNA was extracted from human cell-free plasma using Qiagen CNA kit with the following modifications: (a) 3× volume of ACB Buffer was used, (b) ACW1 Buffer was prepared according to the manufacturer's recommendations and supplemented with an extra 1.75 mL of absolute ethanol and 0.36 g guanidinium chloride per 600 µL of ACW1 Buffer, and (c) ACW2 Buffer was prepared according to the manufacturer's recommendations and supplemented with 1.05 mL of absolute ethanol per 750 µL of ACW2 Buffer. Thus isolated cell-free DNA was used in the NuGen's Ovation Ultralow V2 Library kit with 1.8× Ampure purification steps after adapter ligation and library amplification. The library was then sequenced and the reads mapped to human and pathogen databases. The mapped reads were then investigated.

Figure 8B:
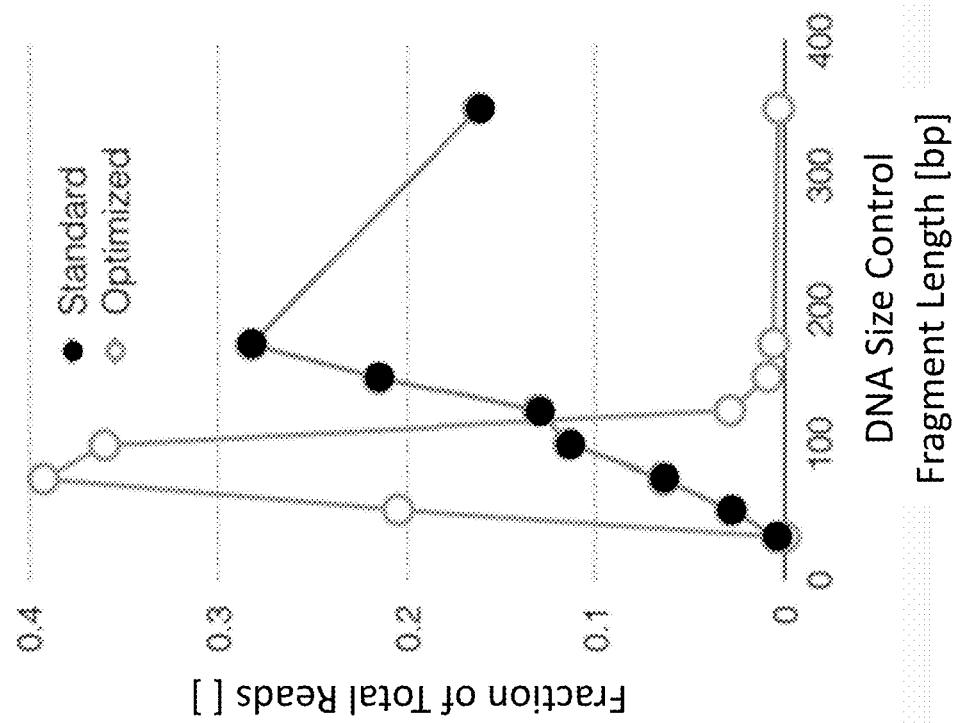
FIG. 8B shows results of a selective enrichment process for short fragment cell-free DNA.
Figure 8A:
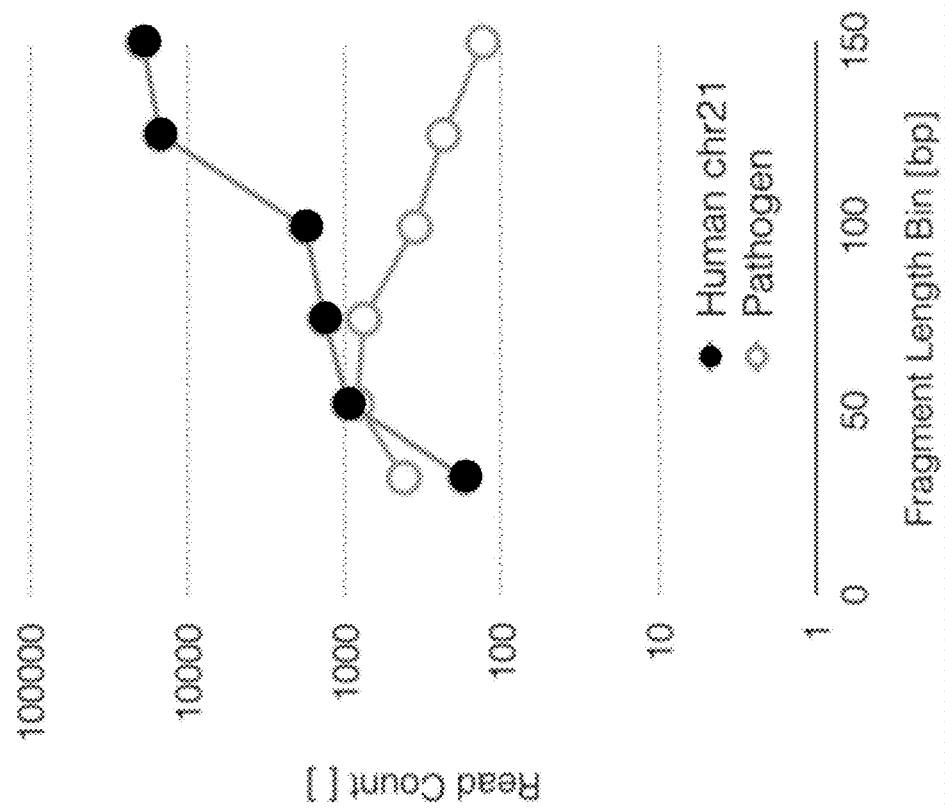
FIG. 8A illustrates a plot of the quantity of cell-free DNA vs. DNA fragment length for both host and non-host cell-free DNA.

In particular, FIG. 8A illustrates a plot of the quantity of cell-free DNA (measured as a function of the number of sequence reads) vs. the fragment length from which the DNA sequence was derived, for both host or human DNA (chr21) and non-host or pathogen DNA. As shown, the non-host DNA enjoys a far more favorable ratio to the host DNA at fragment lengths between about 30 and about 100 bases in length. Accordingly, enrichment of fragments in this size range would be expected to enrich for non-host relative to host DNA.

Enrichment of fragments of the desired size range was tested using a modified Qiagen CNA purification kit on DNA samples that included equimolar cell-free synthetic DNA size controls that are configured to not map to known human or pathogen sequences (e.g., fragments of 32, 52, 75, 100, 125, 150, 175, and 350 bp).

FIG. 8B illustrates the fragment size profile of the sample when processed using a normal CNA kit protocol which selected for larger fragments (e.g., from 100 to 200 bases in length with a peak enrichment at 175 by among the eight DNA size control fragment lengths), while the modified protocol selectively enriched for fragments between 30 bases and about 120 bases, with a peak enrichment at 75 by among the eight DNA size control fragment lengths.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of enriching microbial cell-free nucleic acids, the method comprising:
    (a) identifying nucleic acid length ranges at which a ratio of microbial cell-free nucleic acid to host cell-free nucleic acid is favored;
    (b) providing a host sample wherein the sample is selected from the group consisting of blood, plasma, serum, saliva, cerebrospinal fluid, synovial fluid, and lavage wherein the host sample comprises host cell-free nucleic acids and the microbial cell-free nucleic acids; and
    (c) enriching the microbial cell-free nucleic acids relative to the host cell-free nucleic acids by enriching for nucleic acid length ranges at which a ratio of microbial cell-free nucleic acid to host cell-free nucleic acid is favored.

2. The method of claim 1, comprising removing host cell-free DNA of one or more length intervals from the host sample.

3. The method of claim 1, comprising isolating host cell-free DNA of one or more length intervals from the host sample.

4. The method of claim 2, wherein the length intervals are selected from the group consisting of about 180 bases, about 360 bases, about 540 bases, about 720 bases, about 900 bases, and about 1000 bases.

5. The method of claim 2, wherein the length ranges are length intervals selected from the group consisting of about 150 bases or multiples thereof, about 160 bases or multiples thereof, about 170 bases or multiples thereof, about 190 bases or multiples thereof, and any combination thereof.

6. The method of claim 1, comprising isolating microbial cell-free nucleic acids that are up to about 150 bases in length from the host sample.

7. The method of claim 1, further comprising performing a sequencing assay on the host cell-free nucleic acids and microbial cell-free nucleic acids from the host sample.

8. The method of claim 1, wherein the host sample comprises at least five microbial cell-free nucleic acids and the method further comprises detecting the at least five microbial cell-free nucleic acids.

9. The method of claim 1, wherein the host is human.

10. A method of identifying microbes in a host, the method comprising:
   (a) providing a sample selected from the group consisting of blood, plasma, serum, saliva, cerebrospinal fluid, synovial fluid, and lavage from the host;
   (b) enriching the sample for microbial cell-free nucleic acids relative to host cell-free nucleic acids, wherein the enriching comprises enriching the sample for cell-free nucleic acids with length ranges that are not nucleosomal length ranges;
   (c) analyzing the microbial cell-free nucleic acids; and
   (d) identifying microbes in the host based on the microbial cell-free nucleic acids analyzed in (c).

11. The method of claim 10, wherein the enriching the sample for cell-free nucleic acids with length ranges that are not nucleosomal length ranges comprises preferentially removing nucleic acids from the sample that are above about 150 bases in length.

12. The method of claim 10, wherein the enriching the sample for cell-free nucleic acids with length ranges that are not nucleosomal length ranges comprises preferentially removing nucleic acids with lengths that are above about 300 bases in length from the sample.

13. The method of claim 10, wherein the enriching the sample for cell-free nucleic acids with length ranges that are not nucleosomal length ranges comprises preferentially removing all nucleic acids from the sample that are above about 120 bases in length.

14. The method of claim 10, wherein the enriching the sample for cell-free nucleic acids with length ranges that are not nucleosomal length ranges comprises preferentially enriching cell-free nucleic acids from the sample that are between about 10 bases and about 120 bases in length.

15. The method of claim 10, wherein the enriching the sample for cell-free nucleic acids with length ranges that are not nucleosomal length ranges comprises preferentially digesting host derived nucleic acids.

16. The method of claim 10, wherein the enriching the sample for cell-free nucleic acids with length ranges that are not nucleosomal length ranges comprises preferentially replicating the microbial cell-free nucleic acids.

17. The method of claim 10, wherein the host is human.

18. The method of claim 1, wherein the microbial cell-free nucleic acids are derived from pathogens.

19. The method of claim 18, further comprising performing high throughput sequencing on the sample from the host.

20. The method of claim 18, further comprising performing massively parallel sequencing on the host sample.

21. The method of claim 18, wherein the microbial cell-free nucleic acids comprise DNA.

22. The method of claim 21, wherein the microbial cell-free nucleic acids comprise bacterial, viral, fungal, or parasitic DNA, or a combination thereof.

23. The method of claim 18, wherein the microbial cell-free nucleic acids comprise RNA.

24. The method of claim 23, wherein the microbial cell-free nucleic acids comprise viral RNA.

25. The method of claim 1, wherein the host cell-free nucleic acids or the microbial cell-free nucleic acids are not artificially fragmented.

26. The method of claim 25, wherein the host cell-free nucleic acids or the microbial cell-free nucleic acids are not artificially enzymatically fragmented.

27. The method of claim 2, wherein the one or more length intervals comprises between 110 and 1000 bases.

28. The method of claim 1, wherein the cell-free nucleic acids comprise circulating cell-free nucleic acids.

29. The method of claim 1, wherein the host sample is plasma.

30. The method of claim 10, wherein the sample comprises circulating cell-free nucleic acids.

31. The method of claim 10, wherein the sample is plasma.

32. The method of claim 1, comprising removing host nucleic acids that are above about 150 bases in length from the host sample.

33. The method of claim 32, comprising removing host cell-free DNA that is above about 150 bases in length from the host sample.

34. The method of claim 33, wherein the host cell-free DNA that is above about 150 bases in length is above about 150 base pairs in length.

35. The method of claim 10, wherein the enriching the sample for cell-free nucleic acids with length ranges that are not nucleosomal length ranges comprises preferentially enriching for nucleic acids with lengths that are below about 150 bases in length.

36. The method of claim 1, comprising isolating microbial cell-free nucleic acids that are up to about 110 bases in length from the host sample.

37. The method of claim 10, wherein the enriching the sample for cell-free nucleic acids with length ranges that are not nucleosomal length ranges comprises preferentially enriching cell-free nucleic acids from the sample that are between about 10 bases and about 110 bases in length.

38. The method of claim 1, comprising isolating microbial cell-free nucleic acids that are up to about 70 bases in length from the host sample.

39. The method of claim 10, wherein the enriching the sample for cell-free nucleic acids with length ranges that are not nucleosomal length ranges comprises preferentially enriching cell-free nucleic acids from the sample that are between about 10 bases and about 70 bases in length.

40. The method of claim 1, comprising removing nucleosomal DNA length ranges or nucleosome-associated DNA length ranges.

41. The method of claim 1, wherein the microbial cell-free nucleic acids are enriched at least 2-fold.

42. The method of claim 10, wherein the microbial cell-free nucleic acids are enriched at least 2-fold.

43. The method of claim 1, comprising removing nucleosomal DNA length ranges or nucleosome-associated DNA length ranges, wherein the microbial cell-free nucleic acids are enriched at least 2-fold.

44. The method of claim 40, wherein removing nucleosomal DNA length ranges or nucleosomal-associated DNA length ranges comprises removing at least 50% of the first nucleosomal sized fragments.

45. The method of claim 40, wherein the enriching comprises preferentially removing nucleic acids from the sample that are above about 150 bases in length.

46. The method of claim 10, wherein enriching the sample for cell-free nucleic acids with length ranges that are not nucleosomal length ranges comprises removing at least 50% of the first nucleosomal sized fragments.

47. The method of claim 10, wherein the enriching the sample for cell-free nucleic acids with length ranges that are not nucleosomal length ranges comprises enriching for cell free nucleic acids based on DNA length ranges associated with nucleosomes.

48. The method of claim 10, wherein the method further comprises extracting cell-free nucleic acids from the sample prior to the enriching in (b).

49. The method of claim 10, wherein the enriching the sample for cell-free nucleic acids with length ranges that are not nucleosomal length ranges comprises using one or more antibodies specific to one or more histones.

\* \* \* \* \*